US008784775B2

(12) United States Patent
Lehmann et al.

(10) Patent No.: US 8,784,775 B2
(45) Date of Patent: Jul. 22, 2014

(54) COMPOUNDS FOR USE IN IMAGING, DIAGNOSING AND/OR TREATMENT OF DISEASES OF THE CENTRAL NERVOUS SYSTEM OR OF TUMORS

(75) Inventors: Lutz Lehmann, Berlin (DE); Andrea Thiele, Berlin (DE); Tobias Heinrich, Berlin (DE); Thomas Brumby, Berlin (DE); Christer Halldin, Stockholm (SE); Balazs Gulyas, Solna (SE); Sangram Nag, Huddinge (SE)

(73) Assignee: Piramal Imaging SA, Matran (CH)

( * ) Notice: Subject to any disclaimer, the term of this patent is extended or adjusted under 35 U.S.C. 154(b) by 751 days.

(21) Appl. No.: 12/256,957

(22) Filed: Oct. 23, 2008

(65) Prior Publication Data

US 2009/0191129 A1   Jul. 30, 2009

(30) Foreign Application Priority Data

Oct. 26, 2007  (EP) ..................... 07021042

(51) Int. Cl.
*A61K 49/04* (2006.01)
*A61K 49/00* (2006.01)

(52) U.S. Cl.
USPC ........................................... 424/9.1; 424/9.4

(58) Field of Classification Search
USPC ......................................................... 424/9.4
See application file for complete search history.

(56) References Cited

U.S. PATENT DOCUMENTS

| 3,160,664 A | 12/1964 | Dawson |
| 2001/0021722 A1 | 9/2001 | Brewer |
| 2004/0091525 A1 | 5/2004 | Brewer |
| 2008/0187573 A1 | 8/2008 | Brewer |

FOREIGN PATENT DOCUMENTS

| CN | 1178461 | 4/1998 |
| WO | 9626720 | 9/1996 |

OTHER PUBLICATIONS

Mukherjee et al. (Nucl. Med. Biol. 1999, 26, 619-625).*
Gerig (Fluorine NMR, 2001, p. 1-35, copyright by the author).*
International Search Report of PCT/EP2008/008668 (Jan. 30, 2009).
Written Opinion of the International Searching Authority of PCT/EP2008/008668.
F. Couty et al., "Expeditive Synthesis of Homochiral Fused Tri- and Tetrazoles-Piperazines From β-Amino Alcohols", Tetrahedron Letters, vol. 45 (2004) pp. 3725-3728.
J. Mukherjee et al., "N-(6-$^{18}$F-Fluorohexyl)-N-Methylpropargylamine : A Fluorine-18-Labeled Monoamine Oxidase B Inhibitor for Potential Use in PET Studies", Nuclear Medicine & Biology, vol. 26 (1999) pp. 111-116.
Office Action in parallel Chinese Patent Application No. 200880113171.8, dated Jan. 26, 2014. (6 pages).
English Translation of Office Action in parallel Chinese Patent Application No. 200880113171.8, dated Jan. 26, 2014. (3 pages).
Office Action 2 Notification of the substantive examination results in corresponding Mexican Patent Application No: MX/A/2010/004568. Dated: Mar. 6, 2014. (7 pages).

* cited by examiner

*Primary Examiner* — Michael G Hartley
*Assistant Examiner* — Melissa Perreira
(74) *Attorney, Agent, or Firm* — Millen, White, Zelano & Branigan, P.C.

(57) ABSTRACT

This invention relates to novel compounds suitable for labeling or already labeled by $^{18}$F, methods of preparing such a compound, compositions comprising such compounds, kits comprising such compounds or compositions and uses of such compounds, compositions or kits for diagnostic imaging by positron emission tomography (PET).

44 Claims, 14 Drawing Sheets

Fig.10, cont.
a
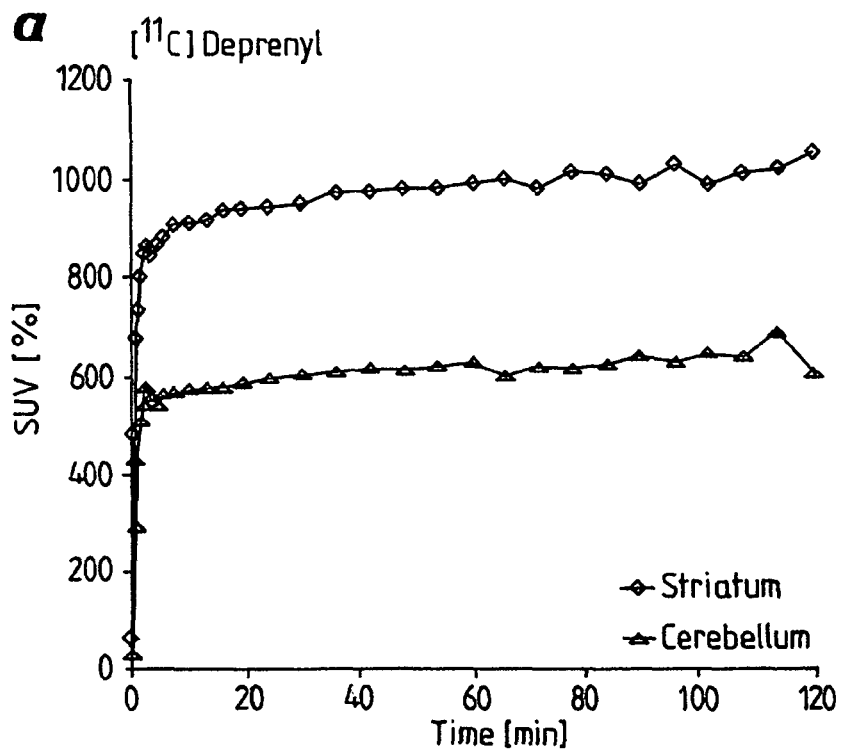
Fig.10, cont.
b
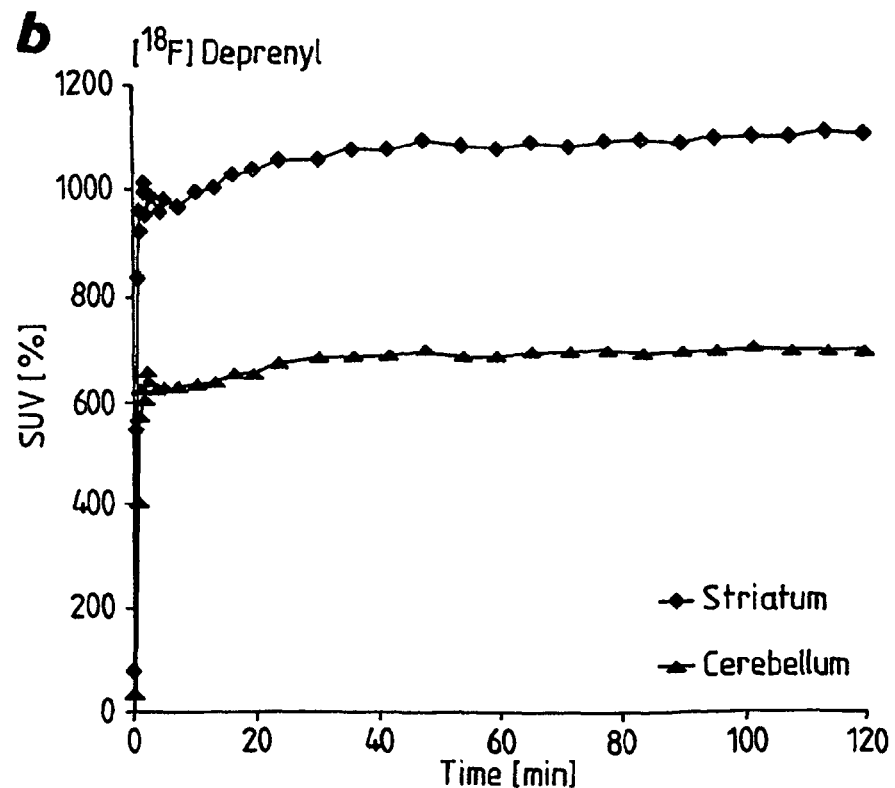

Fig.12 UV & Radio Overlay Chromatograms

Fig. 14
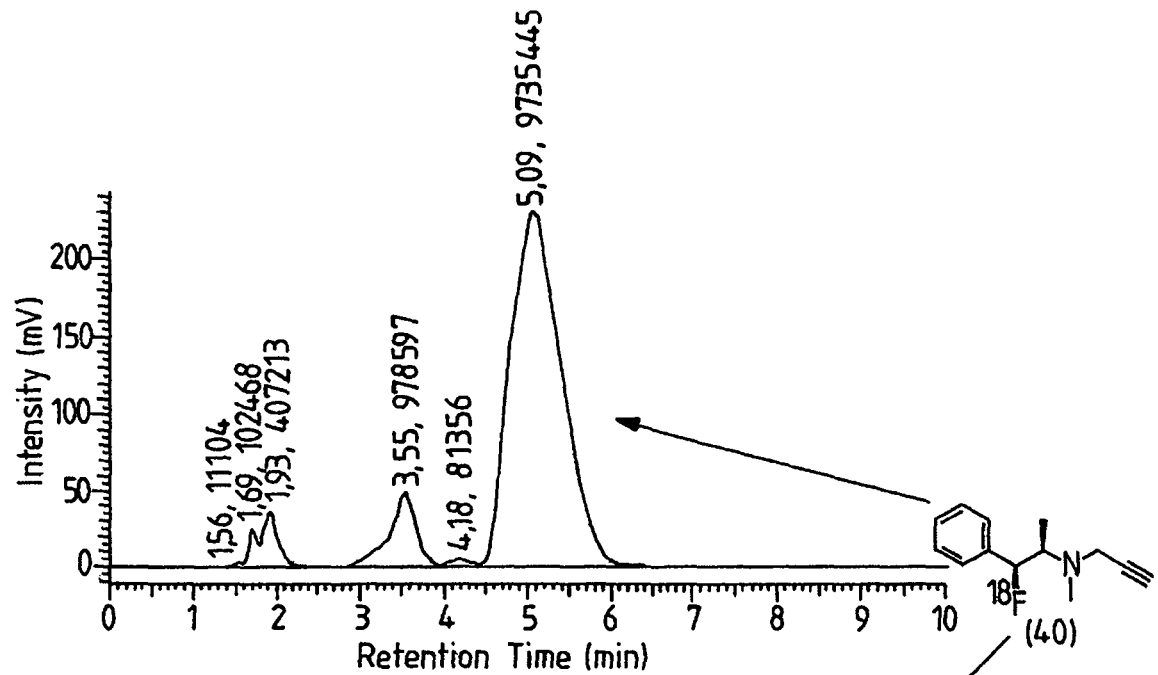
UV HPLC Channel : 1
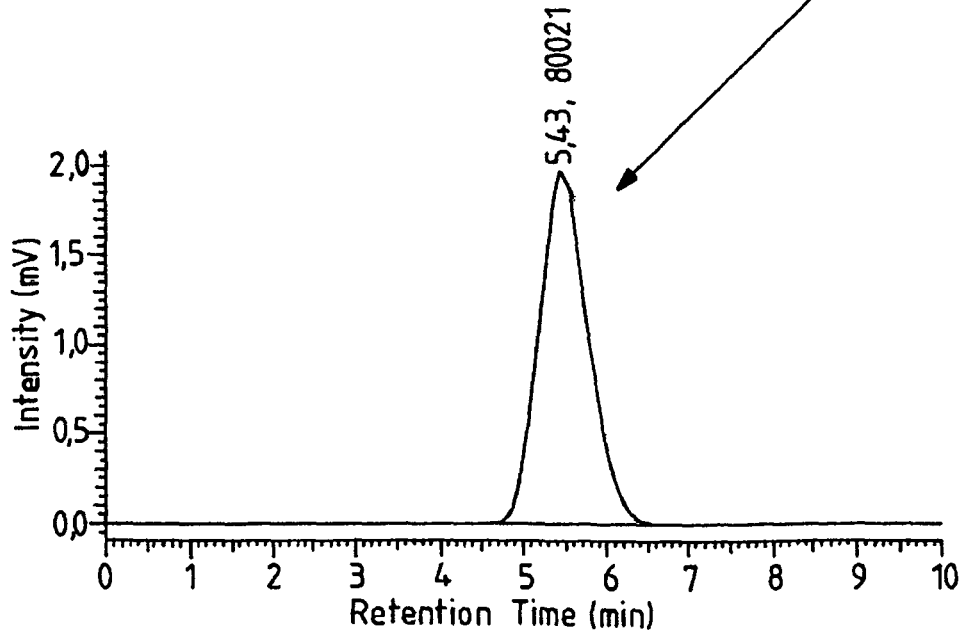
Radio HPLC Channel : 2

COMPOUNDS FOR USE IN IMAGING, DIAGNOSING AND/OR TREATMENT OF DISEASES OF THE CENTRAL NERVOUS SYSTEM OR OF TUMORS

FIELD OF INVENTION

This invention relates to novel compounds suitable for labelling or already labelled by $^{18}$F, methods of preparing such a compound, compositions comprising such compounds, kits comprising such compounds or compositions and uses of such compounds, compositions or kits for diagnostic imaging by positron emission tomography (PET).

BACKGROUND ART

Molecular imaging has the potential to detect disease progression or therapeutic effectiveness earlier than most conventional methods in the fields of oncology, neurology and cardiology. Of the several promising molecular imaging technologies having been developed such as optical imaging, MRI, SPECT and PET, PET is of particular interest for drug development because of its high sensitivity and ability to provide quantitative and kinetic data.

For example positron emitting isotopes include carbon, iodine, nitrogen, and oxygen. These isotopes can replace their non-radioactive counterparts in target compounds to produce tracers that function biologically and are chemically identical to the original molecules for PET imaging. Among these isotopes $^{18}$F is the most convenient labelling isotope due to its relatively long half life (110 min) which permits the preparation of diagnostic tracers and subsequent study of biochemical processes. In addition, its low β+ energy (634 keV) is also advantageous.

The nucleophilic aromatic and aliphatic [$^{18}$F]-fluoro-fluorination reaction is of great importance for [$^{18}$F]-fluoro-labelled radiopharmaceuticals which are used as in vivo imaging agents targeting and visualizing diseases, e.g. solid tumours or diseases of brain. A very important technical goal in using [$^{18}$F]-fluoro-labelled radiopharmaceuticals is the quick preparation and administration of the radioactive compound due to the fact that the $^{18}$F isotopes have a short half-life of about only 110 minutes.

Monoamine Oxidases (MAO, EC, 1.4.3.4) is a distinct class of amine oxidases. MAO is present in two forms: MAO A and MAO B (Med. Res. Rev. 1984, 4, 323-358). Crystal structures of MAO A and MAO B complexed by ligands have been reported (J. Med. Chem. 2004, 47, 1767-1774 and Proc. Nat. Acad. Sci. USA, 2005, 102, 12684-12689).

Search of inhibitors that are selective for both isozyme have been actively performed (e.g. J. Med. Chem. 2004, 47, 1767-1774 and Proc. Nat. Acad. Sci. USA, 2005, 102, 12684-12689). Deprenyl (1) (Biochem Pharmacol. 1972, 5, 393-408) and clorgyline (2) are potent inhibitor of mono amine oxidase inducing irreversible inhibition of the enzymes. The L-isomer of deprenyl (3) is a more potent inhibitor than the D-isomer.

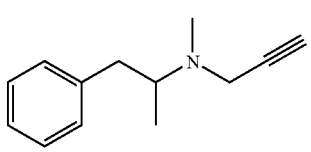

(1)

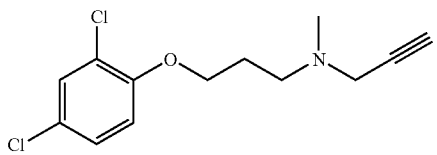

(2)

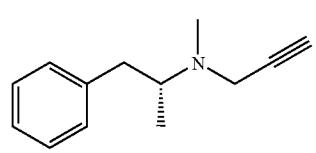

(3)

Neuroprotective and other pharmaceutical effects have also been described for inhibitors (Nature Reviews Neuroscience, 2006, 295, 295-309, Br. J. Pharmacol., 2006, 147, 5287-5296). MAO B inhibitors are for example used to increase DOPA levels in CNS (Progr. Drug Res. 1992, 38, 171-297) and they have been used in clinical trials for the treatment of Alzheimer's disease based on the fact that an increased level of MAO B is involved in astrocytes accociated with Alzheimer plaques (Neuroscience, 1994, 62, 15-30).

Fluorinated MAO inhibitors have been synthesized and biochemically evaluated (review: Kirk et al. in press). F-18 and C-11 labeled MAO inhibitors have been studied in vivo (Journal of the Neurological Science, (2007), 255, 17-22; review: Methods 2002, 27, 263-277). F-18 labeled deprenyl and deprenyl analogues 4-5 have also been reported (int. J. Radiat. Appl. instrument. Part A, Applied Radiat isotopes, 1991, 42, 121, J. Med. Chem. 1990, 33, 2015-2019 and Nucl. Med. Biol. 1990, 26, 111-116, respectively).

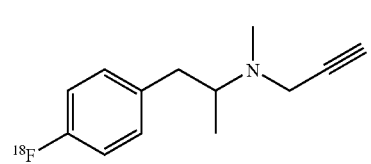

(4)

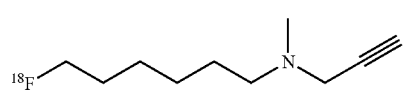

(5)

It would be desirable to have new F-18 labeled compounds and methods available to image diseases which go along with increased level of MAO receptor, especially to have imaging agents and methods available which are easy to realize and which are able to image certain levels of astrocyte activation. This task is solved with the following invention:

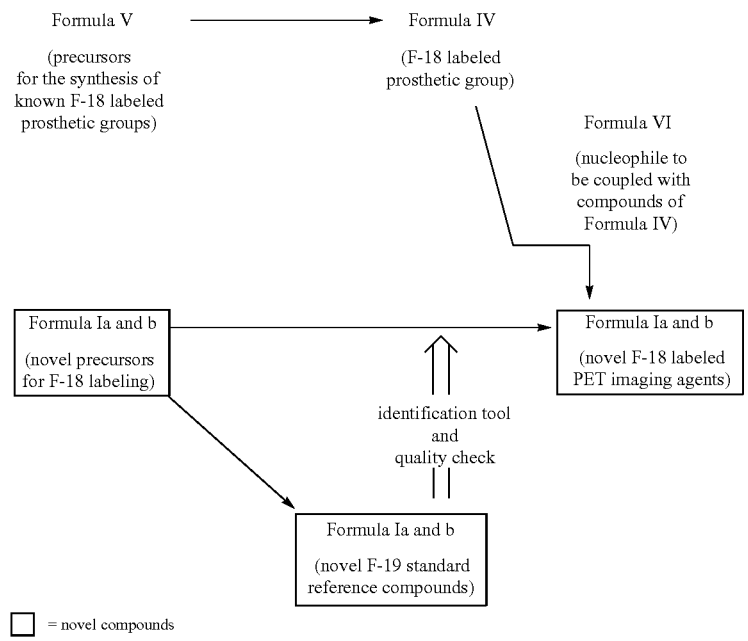

The present invention provides novel compounds of Formulae Ia and Ib. If these compounds of formulae Ia and Ib are not $^{18}$F-labelled or $^{19}$F-labelled, but instead contain an appropriate leaving group, they are starting materials for the synthesis of $^{18}$F-labelled or $^{19}$F-labelled compounds of formulae Ia and Ib. $^{19}$F-labelled compounds of formulae Ia and Ib are standard reference compounds (as identification tool and for quality check) of the synthesis towards $^{18}$F-labelled compounds of formulae Ia and Ib. In the following compounds of formulae Ia and Ib which contain an appropriate leaving group and do not contain $^{18}$F or $^{19}$F, are also referred to as "precursor compounds having formula Ia or Ib". Moreover, those compounds of formula Ia and Ib that contain $^{19}$F instead of an appropriate leaving group are also referred to as "$^{19}$F standard reference compounds having formula Ia or Ib". Moreover, those compounds of formulae Ia and Ib which contain $^{18}$F and which do not contain an appropriate leaving group are also referred to as "$^{18}$F-labelled compounds of formulae Ia or Ib".

The invention further provides a method of imaging diseases, the method comprising introducing into a patient a detectable quantity of a $^{18}$F-labeled compound of Formulae Ia or Ib or a pharmaceutically acceptable salt, ester, amide or prodrug thereof.

The invention provides also $^{18}$F-labelled or $^{19}$F-labelled compounds of Formula Ia and Ib for use as medicament.

The present invention also provides diagnostic compositions comprising a radiolabeled compounds preferably $^{18}$F-labelled compounds of formulae Ia and Ib, and a pharmaceutically acceptable carrier or diluent.

Another aspect of the invention is directed to the use of compounds of formulae Ia and Ib for the manufacture of a medicament, in particular of $^{18}$F- or $^{19}$-F-labelled compounds of formulae Ia or Ib.

The invention also provides a process to synthesize $^{18}$F-labelled compounds of formulae Ia and Ib from precursor compounds having formulae Ia or Ib.

The invention also provides a process to synthesize $^{19}$F-labelled compounds of formulae Ia and Ib from precursor compounds having formulae Ia or Ib.

The invention also provides a process to synthesize $^{18}$F-labelled compounds of formulae Ia or Ib by reacting compounds of Formula IV with compounds of Formula VI. Compounds of formulae IV can be generated by $^{18}$F- or $^{19}$F-fluorinating a compound of formula V.

The invention also provides a kit for preparing a radiopharmaceutical preparation, said kit comprising a sealed vial containing a predetermined quantity of
a precursor compound having formula Ia or Ib, or
compounds of Formula V and VI.

The present invention also provides a kit for imaging diseases. More specifically the compounds of this invention are useful for the imaging of CNS diseases including but not limited to inflammatory and autoimmune, allergic, infectious and toxin-triggered and ischemia-triggered diseases, pharmacologically triggered inflammation with pathophysiological relevance, neuroinflammatory, neurodegenerative diseases. In another embodiment the compounds of this invention are useful for the imaging of tissue, in particular tumors. Examples of inflammatory and autoimmune diseases are chronic inflammatory intestinal diseases (inflammatory bowel diseases, Crohn's disease, ulcerative colitis), arthritis, atheroma, atherosclerosis, inflammatory cardiomyopathy, pemphigus, asthma, multiple sclerosis, diabetes, type I insulin-dependent diabetes mellitus, rheumatoid arthritis, lupus diseases and other collagenoses, Graves' disease, Hashimoto's disease, "graft-versus-host disease" and transplant rejections. Examples of allergic, infectious and toxin-triggered and ischemia-triggered diseases are: sarcoidosis, asthma, hypersensitive pneumonitis, sepsis, septic shock, endotoxin shock, toxic shock syndrome, toxic liver failure, ARDS (acute respiratory distress syndrome), eclampsia, cachexia, acute viral infections (e.g., mononucleosis, fulminant hepatitis), and post-reperfusion organ damage. An example of a pharmacologically triggered inflammation with pathophysiological relevance is the "first dose response" after administration of anti-T-cell antibodies such as OKT3. An example of systemic inflammation reactions of an origin that is as yet unclear is eclampsia. Examples of neurodegenerative and neuroinflammatory diseases that are associated with a astrocyte activation/MAO regulation are dementia, AIDS dementia, amyotrophic lateral sclerosis, encephalitis, neuropathic pain, Creutzfeldt-Jakob disease, Down's syndrome, diffuse Lewy body disease, Huntington's disease, leukoencephalopathy, encephalopathies, septic encephalopathy, hepatic encephalopathy, multiple sclerosis, Parkinson's disease, Pick's disease, Alzheimer's disease, frontotemporal dementia, hippocampal sclerosis, neurocysticercosis, epilepsy, stroke, ischemia, brain tumors, depression, schizophrenia, drug abuse. The invention, therefore, also relates to the use of imaging compounds for diagnosing these diseases as well as for stratification of therapy and therapy monitoring.

In a preferred embodiment compounds of this invention are useful for the imaging of multiple sclerosis, Alzheimer's disease, frontotemporal dementia, dementia with Levy bodies, leukoencephalopathy, epilepsy, neuropathic pain, amyotrophic lateral sclerosis, Parkinson's Disease, encephalopathies, brain tumors, depression, drug abuse, chronic inflammatory intestinal diseases, atheroma, atherosclerosis, arthritis, rheumatoid arthritis, pharmacologically triggered inflammation, systemic inflammation of unclear origin.

In a more preferred embodiment compounds of this invention are useful for the imaging of multiple sclerosis, Alzheimer's disease, amyotrophic lateral sclerosis, Parkinson's Disease, leukoencephalopathy, encephalopathies, epilepsy, brain tumors, drug abuse, chronic inflammatory intestinal diseases, atheroma, rheumatoid arthritis, pharmacologically triggered inflammation and systemic inflammation of unclear origin.

DETAILED DESCRIPTION OF THE INVENTION

In a first aspect the present invention is directed to compounds of formula Ia

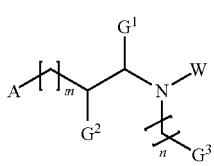

formula Ia or formula Ib

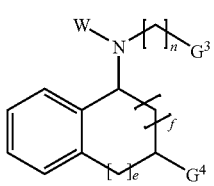

formula Ib wherein
W is selected from the group comprising
—C($U^1$)($U^2$)—C≡CH and cyclopropyl, $U^1$ and $U^2$ being independently selected from hydrogen and deuterium;
A is selected from the group comprising substituted or unsubstituted aryl, substituted or unsubstituted heteroaryl, such as furanyl, ($C_1$-$C_{10}$)alkyl, $G^4$-($C_2$-$C_4$)alkynyl, $G^4$-($C_1$-$C_4$)alkoxy, ($G^4$-($C_1$-$C_4$)alkyl)aryl, ($G^4$-($C_1$-$C_4$)alkoxy)aryl, ($G^4$-($C_1$-$C_4$)alkyl)aryl, and ($G^4$-($C_1$-$C_4$)alkoxy)aryl, heteroaryl is preferably furanyl,
$G^1$, $G^2$, $G^3$ and $G^4$ in formula Ia and formula Ib are independently and individually, at each occurrence, selected from the group comprising hydrogen, ($C_1$-$C_4$)alkyl, preferably methyl, L, and —($C_1$-$C_6$)alkyl-L,
with the proviso that exactly one of $G^1$-$G^4$ in formula Ia are selected from L and —($C_1$-$C_6$)alkyl-L, and
with the proviso that exactly one of $G^3$ and $G^4$ in formula Ib are selected from L and —($C_1$-$C_6$)alkyl-L,
L being a leaving group, or L being F, preferably $^{18}$F or $^{19}$F, wherein, preferably, if L is $^{19}$F, said compound contains exactly one $^{19}$F-atom being attached to an $sp^3$-hybridized carbon atom,
in one embodiment L being $^{18}$F;
in another embodiment L being $^{19}$F;
wherein n is an integer from 0 to 6, preferably 1-3, more preferably 1-2,
and wherein m is an integer from 0 to 4, preferably 0 to 2, more preferably 0-1,
and wherein e and f are integer from 0 to 1, with the proviso that at least one of e and f is 1,
including all isomeric forms of said compound, including but not limited to enantiomers and diastereoisomers as well as racemic mixtures,
and any pharmaceutically acceptable salt, ester, amide, complex or prodrug thereof.

In one embodiment W is —$CH_2$—C≡CH.

In one embodiment A is selected from the group comprising substituted or unsubstituted phenyl, substituted or unsubstituted furanyl, ($C_1$-$C_4$)alkyl, $G^4$-($C_3$-$C_4$), alkynyl, $G^4$-($C_1$-$C_3$)alkoxy, ($G^4$-($C_1$-$C_3$)alkyl)phenyl, ($G^4$-($C_1$-$C_3$)alkoxy)phenyl, wherein, preferably, A is selected from the group comprising phenyl, furanyl, ($G^4$-($C_1$-$C_3$)alkyl)phenyl, ($G^4$-($C_1$-$C_3$)alkoxy)phenyl, preferably, substituted phenyl, hydroxy-phenyl, halo-phenyl, methoxy-phenyl, dimethoxy-phenyl, trifluormethyl-phenyl, and (($C_1$-$C_4$)alkyl)-phenyl, and wherein, more preferably, A is selected from the group comprising phenyl, ($G^4$-($C_1$-$C_3$)alkoxy)phenyl, hydroxyl-phenyl, fluorophenyl, methoxyphenyl, and methylphenyl. More preferably furanyl is furan-2-yl or furan-3-yl.

In one embodiment $G^1$, $G^2$, $G^3$ and $G^4$ in formula Ia, and $G^3$ and $G^4$ in formula Ib are independently and individually, at each occurrence, selected from the group comprising hydrogen, ($C_1$-$C_4$)alkyl, preferably methyl, L, and —($C_1$-$C_4$)alkyl-L,
with the proviso that exactly one of $G^1$-$G^4$ in formula Ia and exactly one of $G^3$-$G^4$ in formula Ib are selected from L and —($C_1$-$C_4$)alkyl-L, wherein, preferably $G^1$, $G^2$, $G^3$ and $G^4$ in formula Ia, and $G^3$ and $G^4$ in formula Ib are independently and individually, at each occurrence, selected from the group comprising hydrogen, methyl, L, and —($C_1$-$C_2$)alkyl-L,
with the proviso that exactly one of $G^1$-$G^4$ in formula Ia and exactly one of $G^3$-$G^4$ in formula Ib are selected from L and —($C_1$-$C_2$)alkyl-L and wherein, more preferably, $G^1$, $G^2$, $G^3$ and $G^4$ in formula Ia, and $G^3$ and $G^4$ in formula Ib are independently and individually, at each occurrence, selected from the group comprising hydrogen, methyl, L, and -methyl-L, with the proviso that exactly one of $G^1$-$G^4$ in formula Ia and exactly one of $G^3$-$G^4$ in formula Ib are selected from L and -methyl-L.

In one embodiment L is a leaving group selected from the group comprising halo, in particular chloro, bromo, iodo, mesyloxy, tosyloxy, trifluormethylsulfonyloxy, nona-fluorobutylsulfonyloxy, (4-bromo-phenyl)sulfonyloxy, (4-nitro-phenyl)sulfonyloxy, (2-nitro-phenyl)sulfonyloxy, (4-isopropyl-phenyl)sulfonyloxy, (2,4,6-tri-isopropyl-phenyl)sulfonyloxy, (2,4,6-trimethyl-phenyl)sulfonyloxy, (4-tertbutyl-phenyl)sulfonyloxy, and (4-methoxy-phenyl)sulfonyloxy.

Preferably, L is selected from the group comprising chloro, bromo, mesyloxy, tosyloxy, trifluormethylsulfonyloxy, (4-bromo-phenyl)sulfonyloxy, (4-nitro-phenyl)sulfonyloxy, (4-isopropyl-phenyl)sulfonyloxy, and (2,4,6-tri-isopropyl-phenyl)sulfonyloxy.

Preferred "precursor compounds having formulae Ia or Ib" are

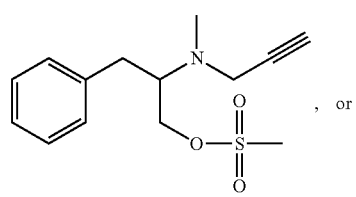

Methanesulfonic acid 2-(methyl-prop-2-ynyl-amino)-3-phenyl-propyl ester

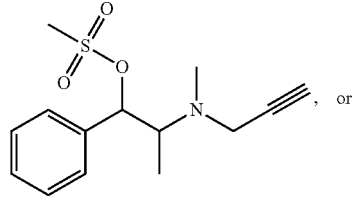

Methanesulfonic acid 2-(methyl-prop-2-ynyl-amino)-1-phenyl-propyl ester

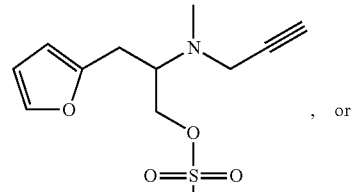

Methanesulfonic acid 3-furan-2-yl-2-(methyl-prop-2-ynyl-amino)-propyl-ester

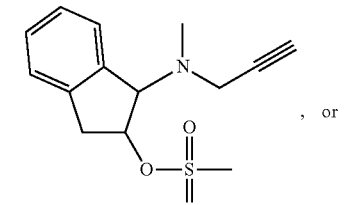

Methanesulfonic acid 1-(methyl-prop-2-ynyl-amino)-indan-2-yl ester

-continued

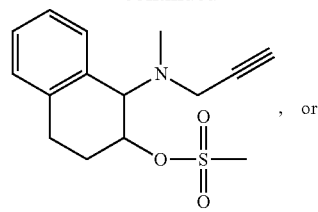

Methanesulfonic acid 1-(methyl-prop-2-ynyl-amino)-1,2,3,4-tetrahydro-naphthalen-2-yl ester

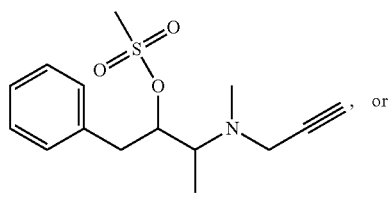

Methanesulfonic acid 1-benzyl-2-(methyl-prop-2-ynyl-amino)-propyl ester

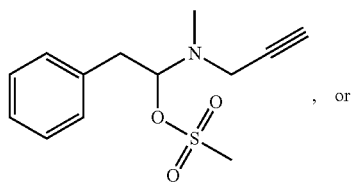

Methanesulfonic acid 1-(methyl-prop-2-ynyl-amino)-2-phenyl-ethyl ester

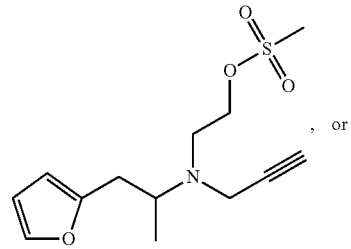

Methanesulfonic acid 2-[(2-furan-2-yl-1-methyl-ethyl)-prop-2-ynyl-amino]-ethyl ester

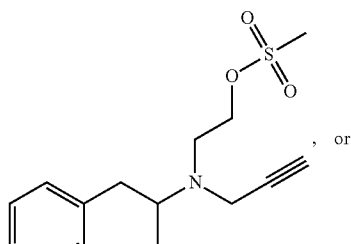

Methanesulfonic acid 2-[(1-methyl-2-phenyl-ethyl)-prop-2-ynyl-amino]-ethyl ester

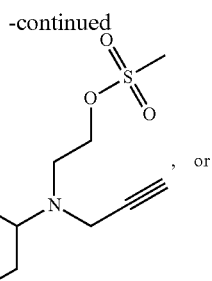

Methanesulfonic acid 2-[prop-2-ynyl-(1,2,3,4-tetrahydro-naphthalen-1-yl)-amino]-ethyl ester

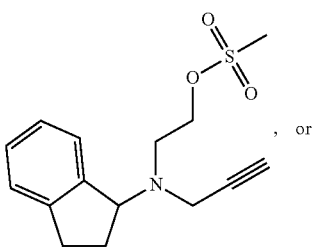

Methanesulfonic acid 2-(indan-1-yl-prop-2-ynyl-amino)-ethyl ester

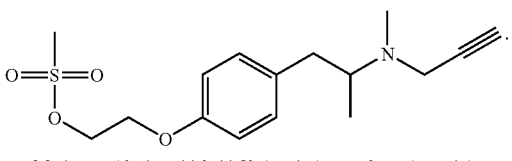

Methanesulfonic acid 2-{4-[2-(methyl-prop-2-ynyl-amnio)-propyl]-phenoxy}-ethyl ester In one embodiment of general formula Ia or Ib, L is not F, in particular not $^{18}$F and not $^{19}$F; these are the aforementioned "precursor compounds".

In another embodiment of general formula Ia or Ib, L is $^{18}$F, or the mesyloxy-group, shown in any of the specific precursor compounds above, is replaced by $^{18}$F. These are the $^{18}$F-labelled compounds having formula Ia or Ib.

In yet another embodiment of general formula Ia or Ib, L is $^{19}$F, or the mesyloxy-group, shown in any of the specific precursor compounds above, is replaced by $^{19}$F. These are the aforementioned "standard reference compounds having formula Ia or Ib".

L is a leaving group which is known or obvious to someone skilled in the art and which is taken from but not limited to those described or named in Synthesis (1982), p. 85-125, table 2 (p. 86; (the last entry of this table 2 needs to be corrected: "n-$C_4F_9$S(O)$_2$—O— nonaflat" instead of "n-$C_4H_9$S(O)$_2$—O— nonaflat"), Carey and Sundberg, Organische Synthese, (1995), page 279-281, table 5.8; or Netscher, Recent Res. Dev. Org. Chem., 2003, 7, 71-83, scheme 1, 2, 10 and 15.

It should be clear that wherever in this description the terms "aryl", "heteroaryl" or any other term referring to an aromatic system is used, this also includes the possibility that such aromatic system is substituted by one or more appropriate substituents, such as OH, halo, alkyl, $NH_2$, $NO_2$, $SO_3$ etc.

The term "aryl" as employed herein by itself or as part of another group refers to monocyclic or bicyclic aromatic groups containing from 6 to 12 carbons in the ring portion, preferably 6-10 carbons in the ring portion, such as phenyl, naphthyl or tetrahydronaphthyl, which themselves can be substituted with one, two or three substituents independently and individually selected from the group comprising halo, nitro, ($C_1$-$C_6$)carbonyl, cyano, nitrile, hydroxyl, trifluormethyl, ($C_1$-$C_6$)sulfonyl, ($C_1$-$C_6$)alkyl, ($C_1$-$C_6$)alkoxy and ($C_1$-$C_6$)sulfanyl. As outlined above such "aryl" may additionally be substituted by one or several substituents.

The term "heteroaryl" as employed herein refers to groups having 5 to 14 ring atoms; 6, 10 or 14 π (pi) electrons shared in a cyclic array; and containing carbon atoms (which can be substituted with halo, nitro, ($C_1$-$C_6$)carbonyl, cyano, nitrile, trifluormethyl, ($C_1$-$C_6$)sulfonyl, ($C_1$-$C_6$)alkyl, ($C_1$-$C_6$)alkoxy or ($C_1$-$C_6$)sulfanyl) and 1, 2, 3 or 4 oxygen, nitrogen or sulfur heteroatoms (where examples of heteroaryl groups are: thienyl, benzo[b]thienyl, naphtho[2,3-b]thienyl, thianthrenyl, furyl, furanyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, carbolinyl, phenanthridinyl, acridinyl, perimidinyl, phenanthrolinyl, phenazinyl, isothiazolyl, phenothiazinyl, isoxazolyl, furazanyl and phenoxazinyl groups).

Heteroaryl can be substituted with one, two or three substituents independently and individually selected from the group comprising halo, nitro, ($C_1$-$C_6$)carbonyl, cyano, nitrile, hydroxyl, trifluormethyl, ($C_1$-$C_6$)sulfonyl, ($C_1$-$C_6$)alkyl, ($C_1$-$C_6$)alkoxy and ($C_1$-$C_6$)sulfanyl. As outlined above such "heteroaryl" may additionally be substituted by one or several substituents.

As used hereinafter in the description of the invention and in the claims, the term "alkyl", by itself or as part of another group, refers to a straight chain or branched chain alkyl group with 1 to 10 carbon atoms such as, for example methyl, ethyl, propyl, isopropyl, butyl, isobutyl, tert-butyl, pentyl, isopentyl, neopentyl, heptyl, hexyl, decyl. Alkyl groups can also be substituted, such as by halogen atoms, hydroxyl groups, $C_1$-$C_4$ alkoxy groups or $C_6$-$C_{12}$ aryl groups (which, intern, can also be substituted, such as by 1 to 3 halogen atoms). More preferably alkyl is $C_1$-$C_{10}$ alkyl, $C_1$-$C_6$ alkyl or $C_1$-$C_4$ alkyl.

As used hereinafter in the description of the invention and in the claims, the term alkynyl is similarly defined as for alkyl, but contain at least one carbon-carbon double or triple bond, respectively, more preferably $C_3$-$C_4$ alkynyl.

As used hereinafter in the description of the invention and in the claims, the term "alkoxy (or alkyloxy)" refer to alkyl groups respectively linked by an oxygen atom, with the alkyl portion being as defined above.

Whenever the term "substituted" is used, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a pharmaceutical composition. The substituent groups may be selected from halogen atoms, hydroxyl groups, nitro, ($C_1$-$C_6$) carbonyl, cyano, nitrile, trifluoromethyl, ($C_1$-$C_6$)sulfonyl, ($C_1$-$C_6$)alkyl, ($C_1$-$C_6$)alkoxy and ($C_1$-$C_6$)sulfanyl.

Preferred examples of $^{18}$F-labelled compounds of formulae Ia or Ib are:

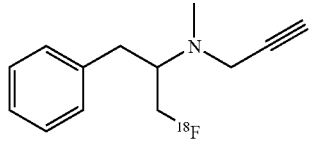
[F-18]-(1-Fluoromethyl-2-phenyl-ethyl)-methyl-prop-2-ynyl-amine

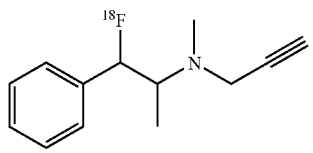
[F-18]-(2-Fluoro-1-methyl-2-phenyl-ethyl)-methyl-prop-2-ynyl-amine

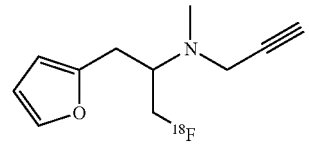
[F-18]-(1-Fluoromethyl-2-furan-2-yl-ethyl)-methyl-prop-2-ynyl-amine

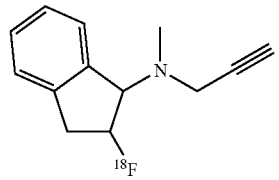
[F-18]-(2-Fluoro-indan-1-yl)-methyl-prop-2-ynyl-amine

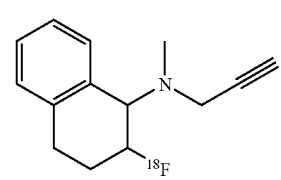
[F-18]-(2-Fluoro-1,2,3,4-tetrahydro-naphthalen-1-yl)-methyl-prop-2-ynyl-amine

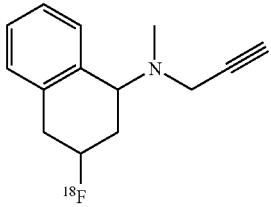
[F-18]-(3-Fluoro-1,2,3,4-tetrahydro-naphthalen-1-yl)-methyl-prop-2-ynyl-amine

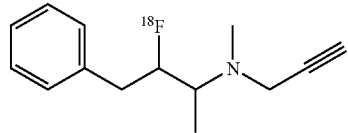
[F-18]-(2-Fluoro-1-methyl-3-phenyl-propyl)-methyl-prop-2-ynyl-amine

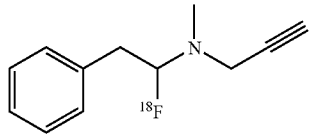
[F-18]-(1-Fluoro-2-phenyl-ethyl)-methyl-prop-2-ynyl-amine

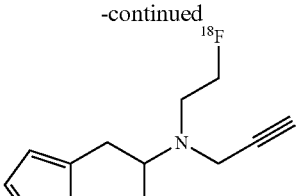
[F-18]-(2-Fluoro-ethyl)-(2-furan-2-yl-1-methyl-ethyl)-prop-2-ynyl-amine

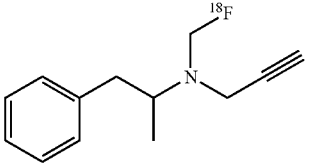
[F-18]-Fluoromethyl-(1-methyl-2-phenyl-ethyl)-prop-2-ynyl-amine

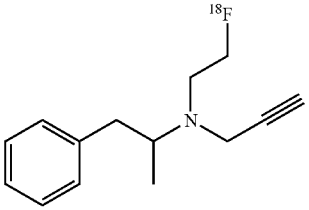
[F-18]-(2-Fluoro-ethyl)-(1-methyl-2-phenyl-ethyl)-prop-2-ynyl-amine

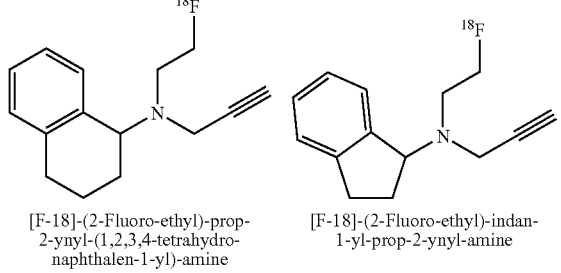
[F-18]-(2-Fluoro-ethyl)-prop-2-ynyl-(1,2,3,4-tetrahydro-naphthalen-1-yl)-amine    [F-18]-(2-Fluoro-ethyl)-indan-1-yl-prop-2-ynyl-amine

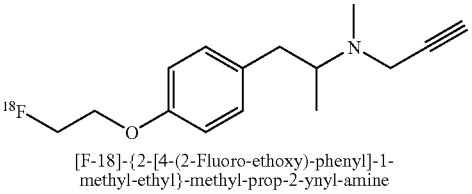
[F-18]-{2-[4-(2-Fluoro-ethoxy)-phenyl]-1-methyl-ethyl}-methyl-prop-2-ynyl-amine In a second aspect of the invention the $^{18}$F-labelled compounds of formula Ia and Ib, and the $^{19}$F standard reference compounds of formulae Ia and Ib are provided as a medicament or pharmaceutical.

The invention relates also to the use of the $^{18}$F-labelled compounds of formula Ia and Ib, and of the $^{19}$F standard reference compounds of formulae Ia and Ib I for the manufacture of a medicament or a pharmaceutical for treatment.

In a more preferred embodiment the use concerns the treatment of a CNS disease. CNS diseases include but are not limited to inflammatory and autoimmune, allergic, infectious and toxin-triggered and ischemia-triggered diseases, pharmacologically triggered inflammation with pathophysiological relevance, neuroinflammatory, and neurodegenerative diseases.

More preferably, the CNS disease is selected from multiple sclerosis, Alzheimer's disease, frontotemporal dementia, dementia with Levy bodies, leukoencephalopathy, epilepsy, neuropathic pain, amyotrophic lateral sclerosis, Parkinson's Disease, encephalopathies, brain tumors, depression, drug abuse, chronic inflammatory intestinal diseases, atheroma, atherosclerosis, arthritis, rheumatoid arthritis, pharmacologically triggered inflammation, systemic inflammation of unclear origin.

The present invention is also directed to a method of treatment of a disease of the central nervous system, as defined above, comprising the step of introducing into a patient a suitable quantity of a compound of formulae Ia or Ib, preferably an $^{18}$F-labelled compound of formulae Ia or Ib, or of a $^{19}$F standard reference compound of formulae Ia or Ib.

In a third aspect of the invention, $^{18}$F-labelled compounds of formulae Ia or Ib are provided as diagnostic imaging agent or imaging agent, preferably as imaging agent for PET applications. The invention relates also to the use of $^{18}$F-labelled compounds of formulae Ia or Ib for the manufacture of an imaging agent.

In a more preferred embodiment the use concerns the imaging of CNS diseases. CNS diseases include but are not limited to inflammatory and autoimmune, allergic, infectious and toxin-triggered and ischemia-triggered diseases, pharmacologically triggered inflammation with pathophysiological relevance, neuroinflammatory, neurodegenerative diseases More preferably, the CNS disease is selected from multiple sclerosis, Alzheimer's disease, frontotemporal dementia, dementia with Levy bodies, leukoencephalopathy, epilepsy, neuropathic pain, amyotrophic lateral sclerosis, Parkinson's Disease, encephalopathies, brain tumors, depression, drug abuse, chronic inflammatory intestinal diseases, atheroma, atherosclerosis, arthritis, rheumatoid arthritis, pharmacologically triggered inflammation, systemic inflammation of unclear origin.

The present invention is also directed to a method of imaging comprising the step of introducing into a patient a detectable quantity of an $^{18}$F-labelled compound of formulae Ia or Ib and imaging said patient.

In a forth aspect of the invention, pharmaceutical compositions are provided comprising a compound according to formulae Ia or Ib, preferably $^{18}$F-labelled compounds of formulae Ia or Ib, or $^{19}$F standard reference compounds of formulae Ia or Ib or a pharmaceutically acceptable salt of an inorganic or organic acid thereof, a hydrate, a complex, an ester, an amide, a solvate or a prodrug thereof. Preferably the pharmaceutical composition comprises a physiologically acceptable carrier, diluent, adjuvant or excipient.

In a preferred embodiment, pharmaceutical compositions according to the present invention comprise a compound of formula Ia or Ib that is a pharmaceutical acceptable hydrate, complex, ester, amide, solvate or a prodrug thereof.

As used hereinafter in the description of the invention and in the claims, the terms "inorganic acid" and "organic acid", refer to mineral acids, including, but not being limited to: acids such as carbonic, nitric, phosphoric, hydrochloric, perchloric or sulphuric acid or the acidic salts thereof such as potassium hydrogen sulphate, or to appropriate organic acids which include, but are not limited to: acids such as aliphatic, cycloaliphatic, aromatic, araliphatic, heterocyclic, carboxylic and sulphonic acids, examples of which are formic, acetic, trifluoracetic, propionic, succinic, glycolic, gluconic, lactic, malic, fumaric, pyruvic, benzoic, anthranilic, mesylic, fumaric, salicylic, phenylacetic, mandelic, embonic, methansulfonic, ethanesulfonic, benzenesulfonic, phantothenic, toluenesulfonic, trifluormethansulfonic and sulfanilic acid, respectively.

In a fifth aspect of the invention, a radiopharmaceutical composition is provided comprising an $^{18}$F-labelled compound of formulae Ia or Ib or a pharmaceutically acceptable salt of an inorganic or organic acid thereof, a hydrate, a complex, an ester, an amide, a solvate or a prodrug thereof.

Preferably the pharmaceutical composition comprises a physiologically acceptable carrier, diluent, adjuvant or excipient.

The compounds according to the present invention, preferably the radioactively labeled compounds according to Formula Ia or Ib provided by the invention may be administered intravenously in any pharmaceutically acceptable carrier, e.g. conventional medium such as an aqueous saline medium, or in blood plasma medium, as a pharmaceutical composition for intravenous injection. Such medium may also contain conventional pharmaceutical materials such as, for example, pharmaceutically acceptable salts to adjust the osmotic pressure, buffers, preservatives and the like. Among the preferred media are normal saline solution and plasma.

Suitable pharmaceutical acceptable carriers are known to someone skilled in the art. In this regard reference can be made to e.g. Remington's Practice of Pharmacy, 13th ed. and in J. of. Pharmaceutical Science & Technology, Vol. 52, No. 5, September-October, p. 238-311, included herein by reference.

The concentration of the compounds of formulae Ia and Ib, preferably of the $^{18}$F-labelled compound according to the present invention and the pharmaceutically acceptable carrier, for example, in an aqueous medium, varies with the particular field of use. A sufficient amount is present in the pharmaceutically acceptable carrier when satisfactory visualization of the imaging target (e.g. a tumor) is achievable.

The compounds according to the present invention, in particular the $^{18}$F-radioactively labeled compounds according to the present invention, i.e. the $^{18}$F-labelled compounds of formulae Ia or Ib, provided by the invention may be administered intravenously in any pharmaceutically acceptable carrier, e.g., conventional medium such as an aqueous saline medium, or in blood plasma medium, as a pharmaceutical composition for intravenous injection. Such medium may also contain conventional pharmaceutical materials such as, for example, pharmaceutically acceptable salts to adjust the osmotic pressure, buffers, preservatives and the like. Among the preferred media are normal saline and plasma. Suitable pharmaceutical acceptable carriers are known to the person skilled in the art. In this regard reference can be made to e.g., Remington's Practice of Pharmacy, 11th ed. and in J. of. Pharmaceutical Science & Technology, Vol. 52, No. 5, September-October, p. 238-311.x In accordance with the invention, the radiolabeled compounds having general chemical Formula II either as a neutral composition or as a salt with a pharmaceutically acceptable counter-ion are administered in a single unit injectable dose. Any of the common carriers known to those with skill in the art, such as sterile saline solution or plasma, can be utilized after radiolabelling for preparing the injectable solution to diagnostically image various organs, tumors and the like in accordance with the invention. Generally, the unit dose to be administered for a diagnostic agent has a radioactivity of about 0.1 mCi to about 100 mCi, preferably 1 mCi to 20 mCi. For a radiotherapeutic agent, the radioactivity of the therapeutic unit dose is about 10 mCi to 700 mCi, preferably 50 mCi to 400 mCi. The solution to be injected at unit dosage is from about 0.01 ml to about 30 ml. For diagnostic purposes after intravenous administration, imaging of the organ or disease in vivo can take place in a matter of a few minutes. However, imaging takes place, if desired, in hours or even longer, after injecting into patients. In most instances, a sufficient amount of the administered dose will accumulate in the area to be imaged within about 0.1 of an hour to permit the taking of scintigraphic images. Any conventional method of scintigraphic imaging for diagnostic purposes can be utilized in accordance with this invention.

As used hereinafter in the description of the invention and in the claims, the term "prodrug" means any covalently bonded compound, which releases the active parent pharmaceutical according to formulae Ia or Ib, preferably the $^{18}$F labelled compound of formulae Ia or Ib. The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmaco-logical Basis of Therapeutics, 8 ed, McGraw-HiM, Int. Ed. 1992, "Biotransformation of Drugs", p 13-15) describing prodrugs generally is hereby incorporated. Prodrugs of a compound of the present invention are prepared by modifying functional groups present in the compound in such a way that the modifications are cleaved, either in routine manipulation or in vivo, to the parent compound. Prodrugs of the compounds of the present invention include those compounds wherein for instance a hydroxy group, such as the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795, WO 99/33815, WO 99/33793 and WO 99/33792 all incorporated herein by reference.

Prodrugs are characterized by excellent aqueous solubility, increased bioavailability and are readily metabolized into the active inhibitors in vivo.

In a sixth aspect the present invention is directed to compounds of Formula Ia or Ib, wherein L is $^{19}$F, with the proviso that such compound contains exactly one $^{19}$F-atom which is attached to an sp$^3$-hybridised carbon atom.

The term "sp$^3$-hybridized carbon atom" refers to a carbon atom which is linked, beside the above mentioned [F-19]-fluoro atom, to three further atoms via a chemical single-bond, so that this carbon atom has got four binding partners in total.

Preferred compounds of Formulae Ia or Ib, with L being $^{19}$F are:

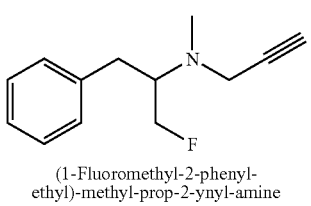

(1-Fluoromethyl-2-phenyl-ethyl)-methyl-prop-2-ynyl-amine

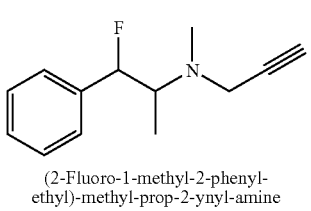

(2-Fluoro-1-methyl-2-phenyl-ethyl)-methyl-prop-2-ynyl-amine

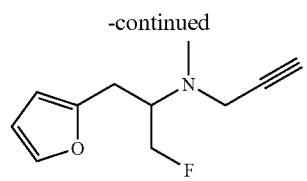

(1-Fluoromethyl-2-furan-2-yl-ethyl)-methyl-prop-2-ynyl-amine

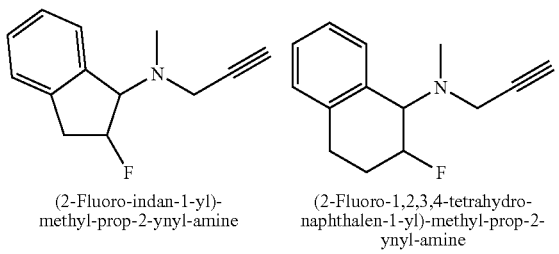

(2-Fluoro-indan-1-yl)-methyl-prop-2-ynyl-amine     (2-Fluoro-1,2,3,4-tetrahydro-naphthalen-1-yl)-methyl-prop-2-ynyl-amine

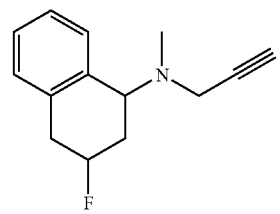

(3-Fluoro-1,2,3,4-tetrahydro-naphthalen-1-yl)-methyl-prop-2-ynyl-amine

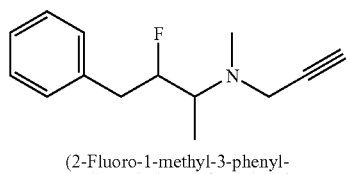

(2-Fluoro-1-methyl-3-phenyl-propyl)-methyl-prop-2-ynyl-amine

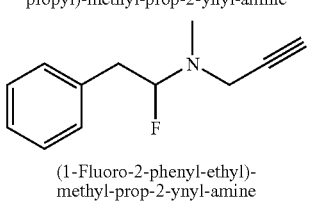

(1-Fluoro-2-phenyl-ethyl)-methyl-prop-2-ynyl-amine

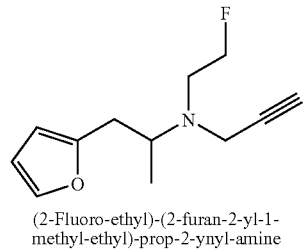

(2-Fluoro-ethyl)-(2-furan-2-yl-1-methyl-ethyl)-prop-2-ynyl-amine

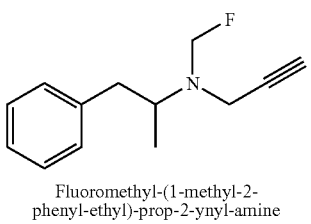

Fluoromethyl-(1-methyl-2-phenyl-ethyl)-prop-2-ynyl-amine

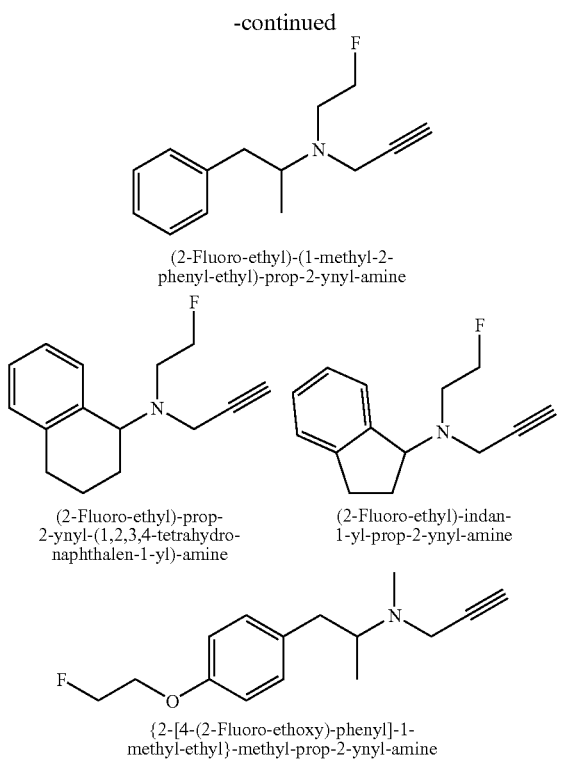

(2-Fluoro-ethyl)-(1-methyl-2-phenyl-ethyl)-prop-2-ynyl-amine (2-Fluoro-ethyl)-prop-2-ynyl-(1,2,3,4-tetrahydro-naphthalen-1-yl)-amine (2-Fluoro-ethyl)-indan-1-yl-prop-2-ynyl-amine {2-[4-(2-Fluoro-ethoxy)-phenyl]-1-methyl-ethyl}-methyl-prop-2-ynyl-amine If a chiral center or another form of an isomeric center is present in a compound according to the present invention, all forms of such isomer, including enantiomers and diastereoisomers, are intended to be covered herein. Compounds containing a chiral center may be used as racemic mixture or as an enantiomerically enriched mixture or the racemic mixture may be separated using well-known techniques and an individual enantiomer maybe used alone. In cases in which compounds have unsaturated carbon-carbon bonds double bonds, both the cis-isomer and trans-isomers are within the scope of this invention. In cases wherein compounds may exist in tautomeric forms, such as keto-enol tautomers, each tautomeric form is contemplated as being included within this invention whether existing in equilibrium or predominantly in one form.

Unless otherwise specified, when referring, to the compounds of formula the present invention per se as well as to any pharmaceutical composition thereof the present invention includes all of the hydrates, solvates, complexes, and prodrugs of the compounds of the invention. Prodrugs are any covalently bonded compounds, which releases the active parent pharmaceutical according to formulae Ia or Ib.

The term "halo" refers to fluorine (F), chlorine (Cl), bromine (Br), and iodine (I).

In a seventh aspect of the invention is directed to a method for obtaining compounds of Formula Ia or Ib, wherein L is $^{18}$F or $^{19}$F.

Surprisingly two methods have been identified for obtaining such compounds.

In a first embodiment, a precursor compound according to formula Ia or Ib, wherein L is a leaving group as defined above, is reacted with an F-fluorinating agent.

Preferably, said F-fluorinating agent is a compound comprising F-anions, preferably a compound selected from the group comprising 4,7,13,16,21,24-hexaoxa-1,10-diazabicyclo[8.8.8]-hexacosane K F, i.e. crownether salt Kryptofix KF, KF, HF, KHF$_2$, CsF, NaF and tetraalkylammonium salts of F, such as [$^{18}$F]-tetrabutylammonium fluoride, and wherein F=$^{18}$F or $^{19}$F.

More specifically, with respect to $^{18}$F-labelled compounds of formulae Ia and Ib, the first embodiment of a radiolabeling method for obtaining an $^{18}$F-labelled compound of formula Ia or Ib comprises the step of $^{18}$F-Radiolabelling a compound of formula Ia or Ib having an appropriate leaving group with a fluorination agent for obtaining an $^{18}$F-labelled compound of formula Ia or Ib, The term "radiolabelling" a molecule, as used herein, usually refers to the introduction of an $^{18}$F-atom into the molecule.

The fluorination agent is defined as above, wherein F=$^{18}$F.

In a second embodiment, a method of synthesis of compounds of Formula Ia and Ib, wherein L is $^{18}$F or $^{19}$F, comprises the steps:

F-fluorinating a compound of formula V formula V

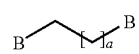

with an F-fluorinating agent to yield a compound of formula IV, formula IV

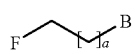

substituting said compound of formula IV with a compound of formula VI formula VI

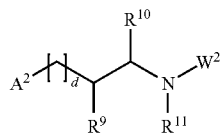

wherein F is $^{18}$F or $^{19}$F, a is an integer from 0 to 4, preferably from 0 to 2, more preferably from 0 to 1, B is a leaving group, preferably halo, in particular chloro, bromo, iodo, mesyloxy, tosyloxy, trifluormethylsulfonyloxy, nona-fluorobutylsulfonyloxy, (4-bromo-phenyl)sulfonyloxy, (4-nitro-phenyl)sulfonyloxy, (2-nitro-phenyl) sulfonyloxy, (4-isopropyl-phenyl)sulfonyloxy, (2,4,6-triisopropyl-phenyl)sulfonyloxy, (2,4,6-trimethyl-phenyl) sulfonyloxy, (4-tertbutyl-phenyl)sulfonyloxy, and (4-methoxy-phenyl)sulfonyloxy, W$^2$ is W as defined in any of claims 1-2, and above, A$^2$ is selected from the group comprising R$^{12}$—O-aryl, R$^2$—O-heteroaryl, aryl, heteroaryl, such as furanyl, (C$_1$-C$_{10}$)alkyl, (C$_2$-C$_4$)alkynyl, (C$_1$-C$_4$)alkoxy, ((C$_1$-C$_4$) alkoxy)aryl, ((C$_1$-C$_4$)alkyl)aryl, wherein R$^9$ and R$^{10}$ are independently and individually, at each occurrence, selected from the group comprising (C$_1$-C$_6$)alkyl and hydrogen, wherein $R^{11}$ is selected from the group comprising ($C_1$-$C_6$) alkyl and $R^{12}$,
wherein $R^{12}$ is hydrogen,
wherein d is an integer from 0 to 4, preferably from 0-2, more preferably from 0-1, and
wherein said F-fluorinating agent is as defined above,
and wherein F=$^{18}$F or $^{19}$F,
with the proviso that compounds of formula VI contain exactly one $R^{12}$.

Preferably, B is selected from the group comprising iodo, bromo, chloro, mesyloxy, tosyloxy, trifluormethylsulfonyloxy, and nona-fluorobutylsulfonyloxy.

Preferably, $A^2$ is selected from the group comprising $R^{12}$—O-phenyl, phenyl, furanyl, ($C_1$-$C_4$)alkyl, ($C_3$-$C_4$)alkynyl, ($C_1$-$C_3$)alkoxy and substituted phenyl, more preferably from the group comprising $R^{12}$—O-phenyl, phenyl, furanyl, (($C_1$-$C_3$)alkoxy)phenyl, hydroxyphenyl, halo-phenyl, methoxy-phenyl, dimethoxy-phenyl, trifluormethyl-phenyl and (($C_1$-$C_4$)alkyl)phenyl, even more preferably from the group comprising $R^{12}$—O-phenyl, phenyl, furanyl, hydroxyphenyl, fluoro-phenyl, methoxy-phenyl, and methyl-phenyl.

Preferably, $R^9$ and $R^{10}$ are independently and individually, at each occurrence, selected from the group comprising ($C_1$-$C_4$)alkyl and hydrogen, preferably from the group comprising methyl and hydrogen.

Preferably, $R^{11}$ is selected from the group comprising ($C_1$-$C_4$)alkyl and $R^{12}$, preferably from the group comprising methyl and $R^{12}$.

More specifically the second embodiment of a radiolabeling method for obtaining an $^{18}$F-labelled compound of formula Ia or Ib comprises the steps of
$^{18}$F radiolabeling a compound of formula V with a fluorination agent to yield a compound of formula IV, and
substituting a compound of formula IV with a compound of Formula VI.

The $^{18}$F-labelled compound of Formula IV is

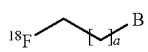

IV or pharmaceutically acceptable salts of an inorganic or organic acid thereof, hydrates, complexes, esters, amides, solvates or prodrugs thereof,
wherein
B is a leaving group;
the leaving group B is known or obvious to someone skilled in the art and which is taken from but not limited to those described or named in Synthesis (1982), p. 85-125, table 2 (p. 86; (the last entry of this table 2 needs to be corrected: "n-$C_4F_9$S(O)$_2$—O— nonaflat" instead of "n-$C_4H_9$S(O)$_2$—O-nonaflat"), Carey and Sundberg, Organische Synthese, (1995), page 279-281, table 5.8; or Netscher, Recent Res. Dev. Org. Chem., 2003, 7, 71-83, scheme 1, 2, 10 and 15;
in a more preferred embodiment B is selected from the group comprising:
a) iodo,
b) bromo,
c) chloro,
d) mesyloxy,
e) tosyloxy,
f) trifluormethylsulfonyloxy and
g) nonafluorobutylsulfonyloxy;
a is an integer from 0 to 4, preferably a is an integer of from 0 to 2 and more preferably a is an integer of from 0 to 1;

The compound of Formula V is

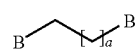

V or pharmaceutically acceptable salts of an inorganic or organic acid thereof, hydrates, complexes, esters, amides, solvates or prodrugs thereof,
wherein
B is defined as above for compounds of Formula IV, and
a is defined as above for compounds of Formula IV,
The fluorination agent is defined as above.
The compound of Formula VI is

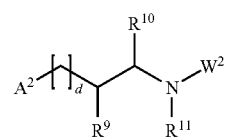

VI or pharmaceutically acceptable salts of an inorganic or organic acid thereof, hydrates, complexes, esters, amides, solvates or prodrugs thereof,
wherein $A^2$ is selected from the group comprising
a) $R^{12}$—O-aryl and
b) $R^{12}$—O-heteroaryl;
c) aryl,
d) heteroaryl,
e) ($C_1$-$C_{10}$)alkyl,
f) ($C_2$-$C_4$)alkynyl,
g) ($C_1$-$C_4$)alkoxy,
h) ($C_1$-$C_4$)alkoxy)aryl,
i) (($C_1$-$C_4$)alkyl)aryl and
j) (($C_1$-$C_4$)alkoxy)aryl;
in a preferred embodiment $A^2$ is selected from the group comprising
a) $R^{12}$—O-phenyl,
b) phenyl,
c) furanyl,
d) ($C_1$-$C_4$)alkyl,
e) ($C_3$-$C_4$)alkynyl,
f) ($C_1$-$C_3$)alkoxy and
g) substituted phenyl;
in a more preferred embodiment $A^2$ is selected from the group comprising
a) $R^{12}$—O-phenyl,
b) phenyl,
c) furanyl,
d) (($C_1$-$C_3$)alkoxy)phenyl,
e) hydroxy-phenyl
f) halo-phenyl,
g) methoxy-phenyl,
h) dimethoxy-phenyl,
i) trifluormethyl-phenyl and
j) (($C_1$-$C_4$)alkyl)-phenyl;
In an even more preferred embodiment $A^2$ is selected from the group comprising
a) $R^{12}$—O-phenyl,
b) phenyl,
c) furanyl,
d) hydroxyl-phenyl,
e) fluoro-phenyl,
f) methoxy-phenyl and
g) methyl-phenyl;

$W^2$ is selected from the group comprising
  a) —C($U^3$)($U^4$)—C≡CH and
  b) cyclopropyl;
in a preferred embodiment $W^2$ is —$CH_2$—C≡CH;
$U^3$ and $U^4$ are independently and individually selected from the group comprising
  a) hydrogen and
  b) deuterium;
in a preferred embodiment $U^3$ and $U^4$ are hydrogen;
$R^9$ and $R^{10}$ are independently selected from the group
  a) ($C_1$-$C_6$)alkyl and
  b) hydrogen;
in a preferred embodiment $R^9$ and $R^{10}$ are independently selected from the group
  a) ($C_1$-$C_4$)alkyl and
  b) hydrogen;
in a more preferred embodiment $R^9$ and $R^{10}$ are independently selected from the group
  a) methyl and
  b) hydrogen;
$R^{11}$ is selected from the group comprising
  a) ($C_1$-$C_6$)alkyl and
  b) $R^{12}$;
in a preferred embodiment $R^{11}$ is selected from the group comprising
  a) ($C_1$-$C_4$)alkyl and
  b) $R^{12}$;
in a preferred embodiment $R^{11}$ is selected from the group comprising
  a) methyl and
  b) $R^{12}$;
d is an integer from 0-4, in a preferred embodiment m is an integer from 0-2, in a more preferred embodiment m is an integer from 0-1;
$R^{12}$ is hydrogen;
with the proviso that compounds of Formula VI contain exactly one $R^{12}$.

In a preferred embodiment, the fluorination agent is a fluorine radioactive isotope derivative. More preferably the fluorine radioactive isotope derivative is a $^{18}F$ derivative. More preferably, the $^{18}F$ derivative is 4,7,13,16,21,24-Hexaoxa-1,10-diazabicyclo[8.8.8]-hexacosane K 8F (crownether salt Kryptofix K$^{18}$F), K$^{18}$F, H$^{18}$F, KH$^{18}F_2$, Cs $^{18}$F, Na$^{18}$F or tetraalkylammonium salt of $^{18}$F (e.g. [F-18] tetrabutylammonium fluoride). More preferably, the fluorination agent is K$^{18}$F, H$^{18}$F, or $_{KH}{}^{18}F_2$ most preferably K$^{18}$F ($^{18}$F fluoride anion).

The radiofluorination reaction can be carried out, for example in a typical reaction vessel (e.g. Wheaton vial) which is known to someone skilled in the art or in a microreactor. The reaction can be heated by typical methods, e.g. oil bath, heating block or microwave. The radiofluorination reactions are carried out in dimethylformamide with potassium carbonate as base and "kryptofix" as crown-ether. But also other solvents can be used which are well known to experts. These possible conditions include, but are not limited to: dimethylsulfoxid and acetonitril as solvent and tetraalkyl ammonium and tertraalkyl phosphonium carbonate as base. Water and/or alcohol can be involved in such a reaction as co-solvent. The radiofluorination reactions are conducted for one to 60 minutes. Preferred reaction times are five to 50 minutes. Further preferred reaction times are 10 to 40 min. This and other conditions for such radiofluorination are known to experts (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50). The radiofluorination can be carried out in a "hotcell" and/or by use of a module (eview: Krasikowa, Synthesis Modules and Automation in F-18 labeling (2006), in: Schubiger P. A., Friebe M., Lehmann L., (eds), PET-Chemistry—The Driving Force in Molecular Imaging. Springer, Berlin Heidelberg, pp. 289-316) which allows an automated or semi-automated synthesis.

Furthermore, the invention provides for a composition comprising a compound according to the present invention and a pharmaceutically acceptable carrier or diluent.

In one embodiment said compound is an $^{18}F$-labelled compound.

In another embodiment said compound is a $^{19}F$-labelled compound.

In yet another embodiment said compound is a precursor compound.

The invention also provides for a compound according to the present invention, preferably an $^{18}$F- or $^{19}$F-labelled compound according the present invention, or a composition according to the present invention for use as a pharmaceutical or diagnostic agent or imaging agent.

The invention also provides for the use of a compound according to the present invention, preferably an $^{18}$F- or $^{19}$F-labelled compound according to the present invention, or a composition according to the present invention for the manufacture of a medicament for the treatment and/or diagnosis and/or imaging of diseases of the central nervous system (CNS).

The invention also provides for an $^{18}F$-labelled compound of formulae Ia or Ib or a composition containing such compound for use as a diagnostic agent or imaging agent, in particular for diseases of the central nervous system.

The invention also provides for a kit comprising a sealed vial containing a predetermined quantity of a compound
a) which is a precursor compound having formula I a or Ib, or
b) a compound of formula V and a compound of formula VI, as defined above.

The invention also provides for a method for detecting the presence of monoamine oxidase in a patient's body, preferably for imaging a disease of the central nervous system in a patient, comprising:
introducing into a patient's body a detectable amount of an $^{18}F$-labelled compound according to the present invention or a composition comprising such compound,
and detecting said compound or said composition by positron emission tomography (PET).

The invention also provides for a method of treatment of a disease of the central nervous system comprising the step of introducing into a patient a suitable quantity of a compound according to the present invention, preferably of an $^{18}$F- or $^{19}$F-labelled compound according to the present invention.

Synthesis of Compounds

Depending on which carbon atom of compounds of formula Ia the fluoro atom (F-19 or F-18) or the leaving group (compare $G^1$ to $G^4$) is attached to different synthesis strategies are possible: (numbered in the following as "1)"-"4)".

1) A fluoro atom (F-19 or F-18) or a leaving group (compare $G^3$) is attached via a linker to the central nitrogen atom:

A series of different suited co-substituted 1-(alkyl)alkyl amines (A1) (see scheme 1) are commercially available. They serve as starting material for the alkylation with e.g. propargyl bromide. Alternatively, ω-substituted 2-bromo-alkanes (A2) can serve as electrophile in a chemical reaction with propargyl amine or cyclobutyl amine.

scheme 1

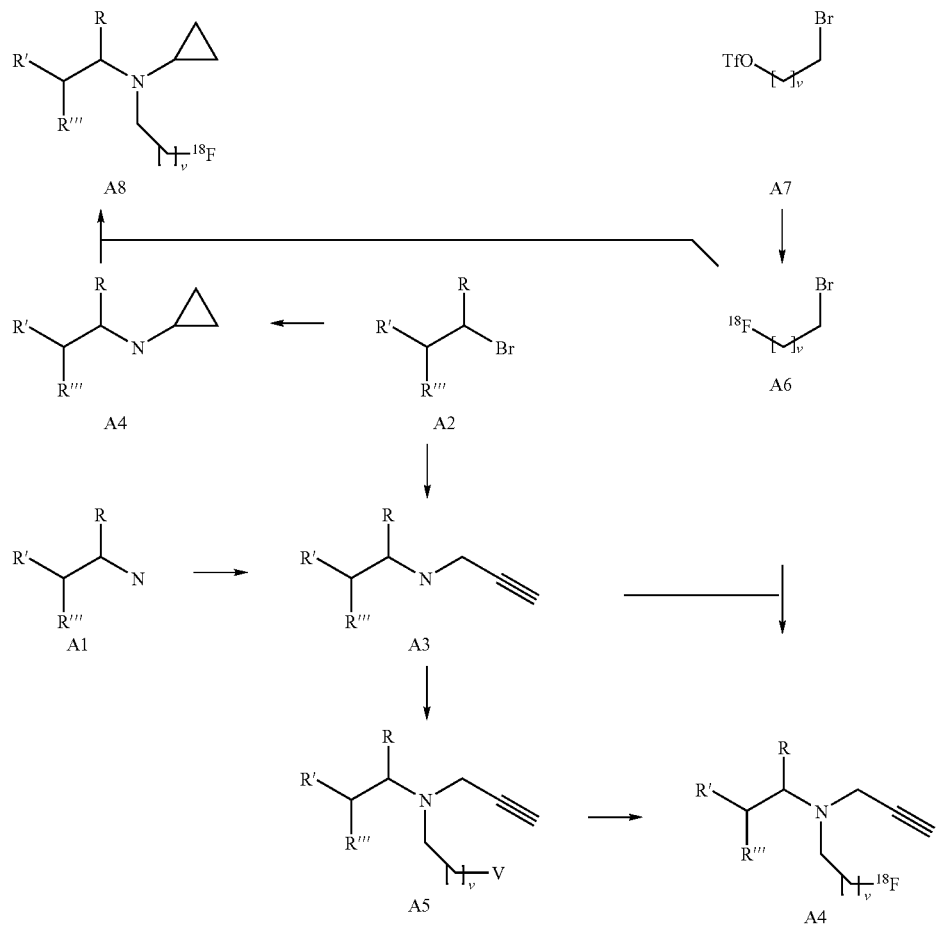

Compound A3 can be alkylated with [F-18]-ω-fluoro-alkyl-bromide (A6), which is generated from the corresponding triflate (A7), towards compound A4. Compound A3 can also be alkylated with a ω-functionalized building block towards A5, so that a later leaving group (V) of A5 is then converted to the [F-18] fluoro atom of compound A4.

A concrete example of this approach in schem 1 is shown in scheme 2: ammonium salt 6 (Sigma) is liberated towards the corresponding free amine (7) by basic aqueous extraction. The compound 7 is then alkylated with [F-18]-2-fluoro-ethyl-bromide (Bioorg. Med. Chem.; 13; 20; 2005; 5779-5786) using base (e.g. sodium hydride) to obtain compound 8.

scheme 2

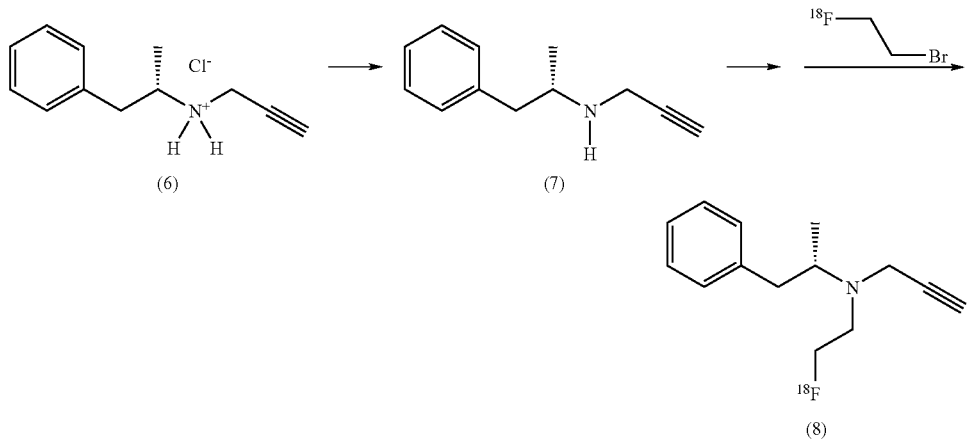

2) A fluoro atom (F-19 or F-18) or a leaving group (compare substituent G¹) is attached in α-position to the central nitrogen atom:

scheme 3

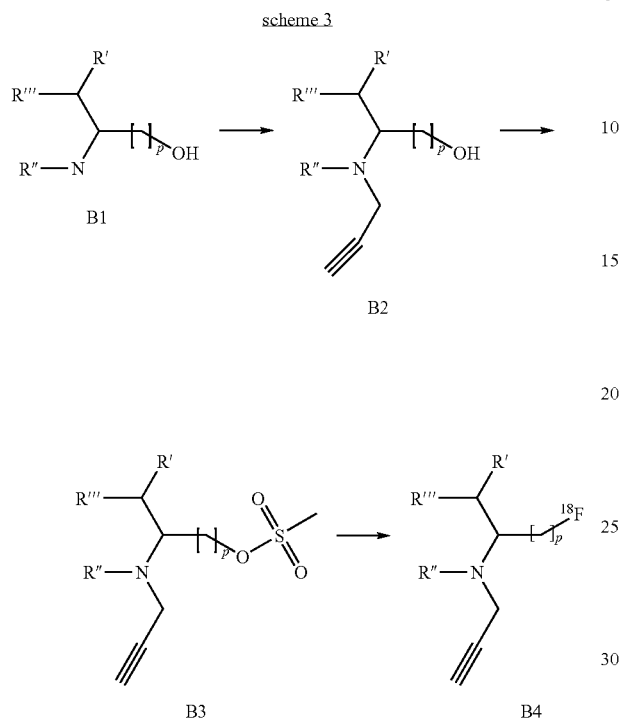

Amino alcohols (see B1, scheme 3) of which many examples are known in literature or which are commercially available can be alkylated with e.g. propargyl bromide towards compound B2. The introduction of a leaving group (mesyloxy shown, but also other leaving groups possible) can be generated by standard methods to obtain compound B3. The leaving group of compound B3 is substituted by using a fluorinating agent to obtain compound B4.

A concrete example of a synthesis according to scheme 3 is shown in scheme 4 scheme 4

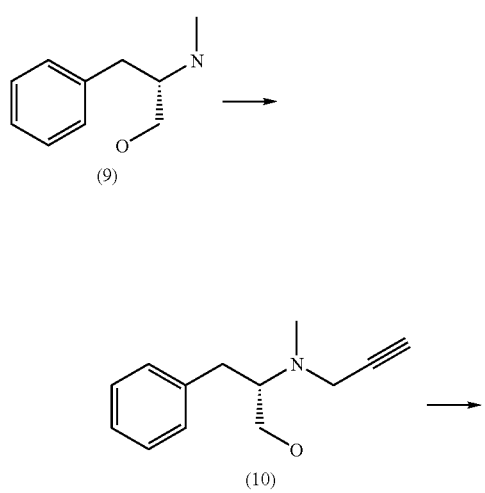

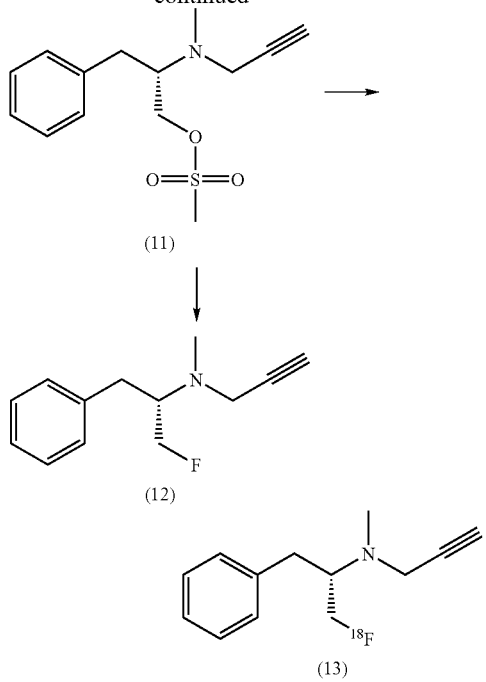

Compound 9 (compare J. Organomet. Chem.; 317; 1986; 93-104) is N-alkylated with propargyl bromide. This reaction can be carried out in dimethylformamide and potassium carbonate (e.g. Org. Lett.; 8; 14; 2006; 2945-2947) in dimethylformamide to obtain alcohol 10. But also other bases, including but not limited to caesium or sodium carbonate, sodium hydroxid, potassium hydroxid, lithium hydroxid, tetra-alkyl ammonium hydroxid, sodium hydrid and other solvents, including but not limited to acetone, tetrahydrofuran, eventually mixed with water, are possible. The resulting alcohol 10 is then converted to compound 11 by use of e.g. mesylchloride, triethylamin and dichloromethane. Other possible solvents and bases including but not limited to, are dichloroethane, ethers, ethyl acetate, diisopropyl ethyl amine, DABCO ect. Under certain circumstances the mesylate 11 serves just as intermediate which forms an corresponding "in-situ" aziridine. This derivative (not shown) is then opened by the chloro-anion-nucleophile which is present in solution leading to a suited chloro-precursor molecules (compare scheme 11, compound 42 and 43). Therefore other mesylation reagents might be also considered, like mesyl anhydride (compare e.g. Tetrahedron; 63; 25; 2007; 5470-5476) to generate the mesylate as stable derivative. Nevertheless the chloro precursor compounds 42 and 43 are also suited to generate F-18 labelled molecules (compare scheme 11 compound 13 and 39. The subsequent radiofluorination reaction of compound 11 towards compound 13 is carried out in dimethylformamide with potassium carbonate as base and "kryptofix" as crown-ether. But also other solvents can be used which are well known to experts. These possible conditions include, but are not limited to: dimethylsulfoxid and acetonitril as solvent and tetraalkyl ammonium, tertraalkyl phosphonium carbonate or caesium carbonate as base. Water and/or alcohol can be involved in such a reaction as co-solvent. The radiofluorination reaction is conducted at 105° C. for ca. 10 min. The mesylate 11 can also be converted to the non-radioactive fluoride 12. Suited reagents for this reaction are potassium fluoride and "kryptofix" in acetonitrile. The reaction mixture is optionally heated by microwave technique. Alternatively, compound 12 can also be obtained from compound 10 by treatment with DAST in dichloromethane. This procedure is known to experts in the field (e.g. J. Med. Chem.; 49; 8; 2006; 2496-2511).

3) A fluoro atom (F-19 or F-18) or a leaving group (compare substituent G²) is attached in β-position to the central nitrogen atom:

This approach is similar to the approach dicribed in 2). One can start from amino alcohols C1 which are known in literature or which are commercially available. The amino and alcohol group can be even protected (not shown in scheme 5, but exaplified in scheme 6). C1 can be alkylated with e.g. propargyl bromide towards compound C2. The introduction of a leaving group (mesyloxy shown, but also other leaving groups possible) can be generated by standard methods to obtain compound C3. The leaving group of compound C3 is substituted by using a fluorinating agent to obtain compound C4.

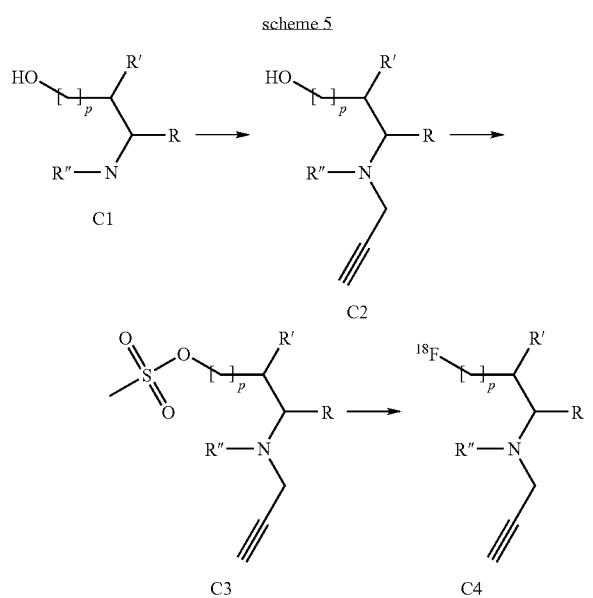

A concrete example of this approach (scheme 5) is shown in scheme 6. Amino alcohol 13 (Aldrich) which is protected as cyclic carbamate is alkylated with propargyl halogenide, for example progargyl bromide (Aldrich), by methods which are known to experts in the field (comp. J. Org. Chem.; 71; 13; (2006); 5023-5026.). This reaction can be carried out for example in DMF or THF using strong bases such as sodium hydride obtaining oxazolidinon 14. Compound 14 can be reduced with lithium alanate towards alcohol 15 (analogues to *J. Carbohydr. Chem.*; 24; 2; (2005); 187-197). Alcohol 15 can be converted to the mesylate 16 by standard methods which comprise e.g. mesylchloride in dichloromethane and triethyl amine as base. Triflate 16 serves as precursor for the radiofluorination. Thus, the conversion towards compound 17 is carried out using potassium fluoride and "kryptofix" in acetonitrile. Compound 18 serves as standard reference compound for the described radiofluorination reaction. The mesylate 16 can also be converted to the non-radioactive fluoride 16. Suited reagents for this reaction are potassium fluoride and "kryptofix" in acetonitrile. The reaction mixture is optionally heated by microwave technique. Alternatively, compound 16 can also be obtained from compound 15 by treatment with DAST in dichloromethane. This procedure is known to experts in the field (e.g. J. Med. Chem.; 49; 8; 2006; 2496-2511).

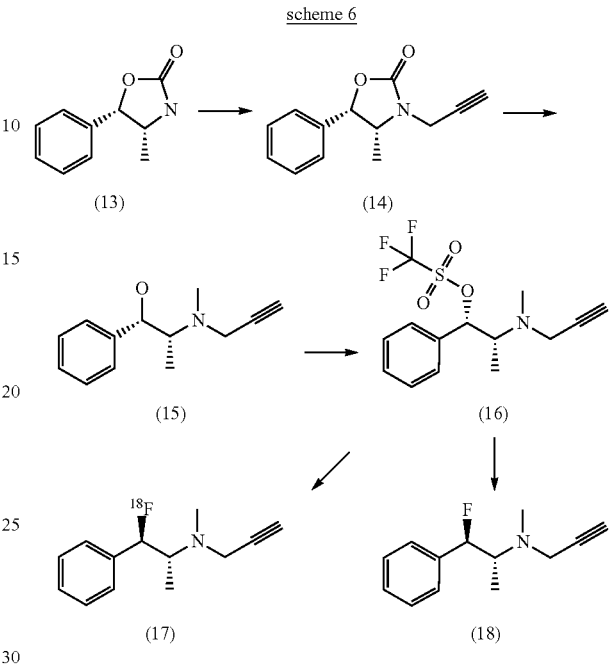

4) A fluoro atom (F-19 or F-18) or a leaving group (compare substituent G⁴) is attached in ω-position to the central nitrogen atom:

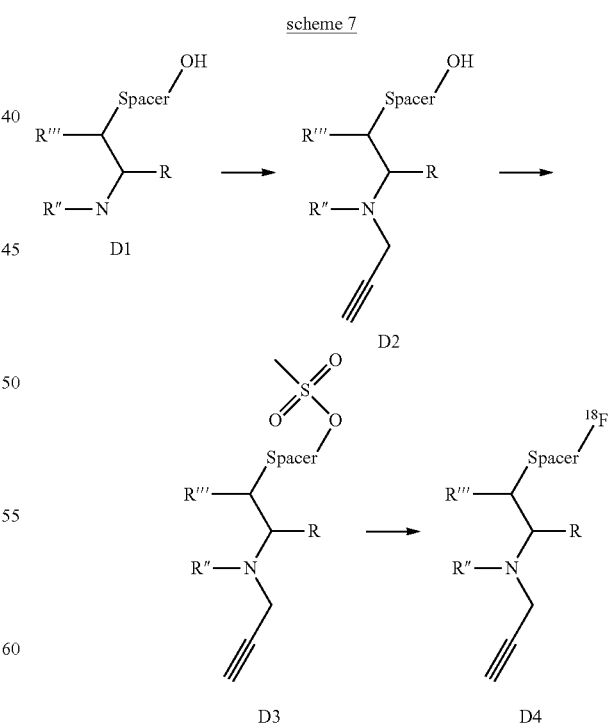

Amino alcohols (see D1, scheme 7 (hydroxyl functionality can optionally be protected; "spacer" according to substituent A in formula Ia) of which many examples are known in literature or which are commercially available can be alkylated with e.g. propargyl bromide towards compound D2. The introduction of a leaving group (mesyloxy shown, but also other leaving groups possible) can be generated by standard methods to obtain compound D3. The leaving group of compound D3 is substituted by using a fluorinating agent to obtain compound D4.

A concrete example of this approach is shown in scheme 8: methyl ester 19 (Pharmazie (1997), 52, 12, 937) is reduced to the corresponding alcohol by use of sodium boro hydride (e.g. Tetrahedron; 63; 9; 2007; 2000-2008). The amino protecting group is subsequently removed by dissolving the intermediate in MeOH(aq) and alkali (sodium or potassium) carbonate (e.g J. Org. Chem., 53, (1988), 3108). The amino group of compound 20 is alkylated with propargyl bromide in DMF and potassium carbonate (e.g. Org. Lett.; 8; 14; 2006; 2945-2947) to obtain compound 21. The alcohol 21 is converted in the corresponding mesylate 22 which is fluorinated towards 23 and 24 by using fluorinating agents.

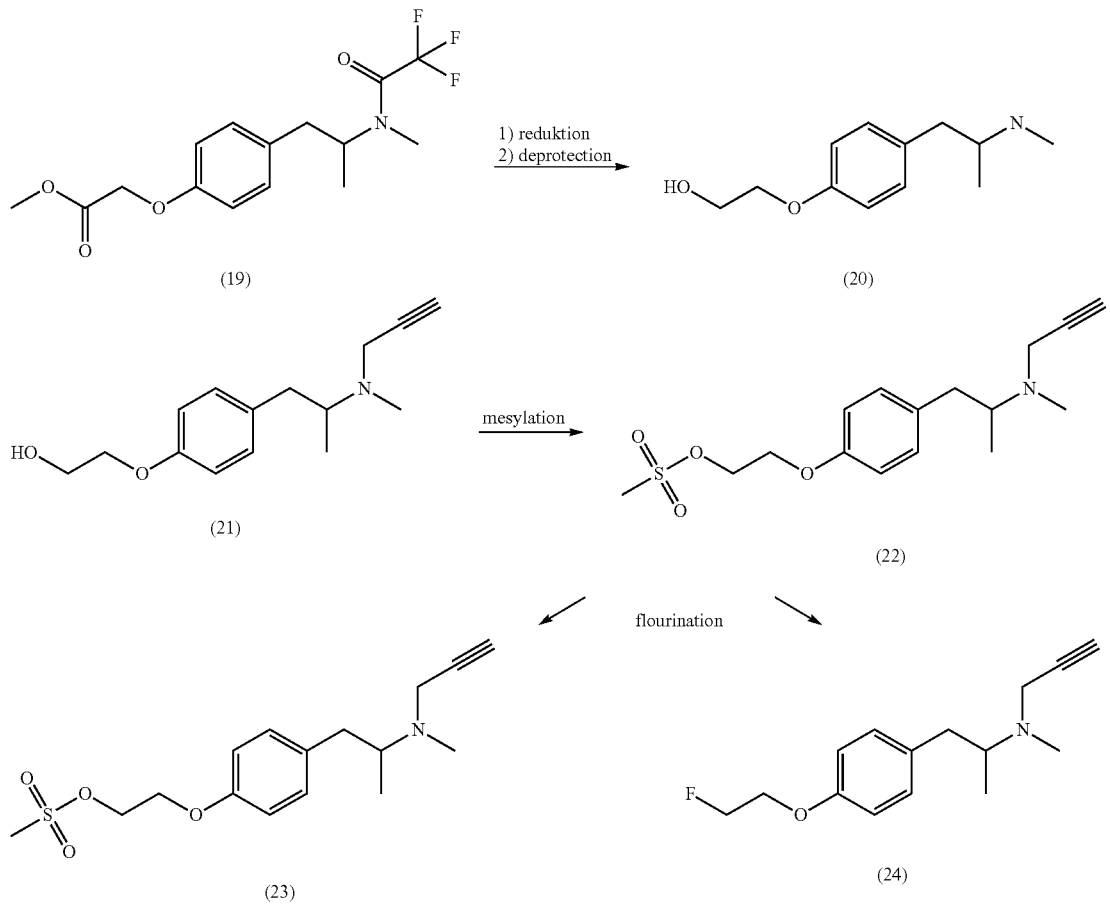

An example for the synthesis of compounds of formula Ib is shown in scheme 10:

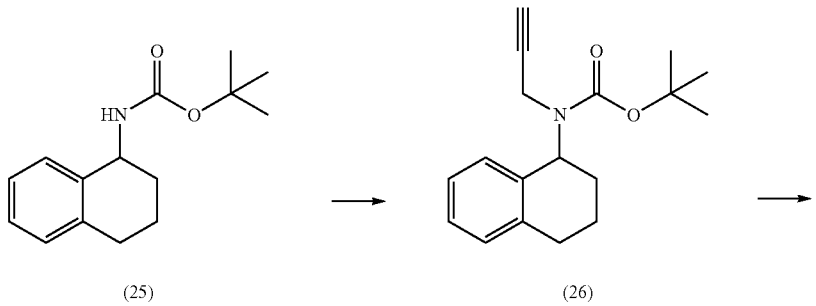

-continued

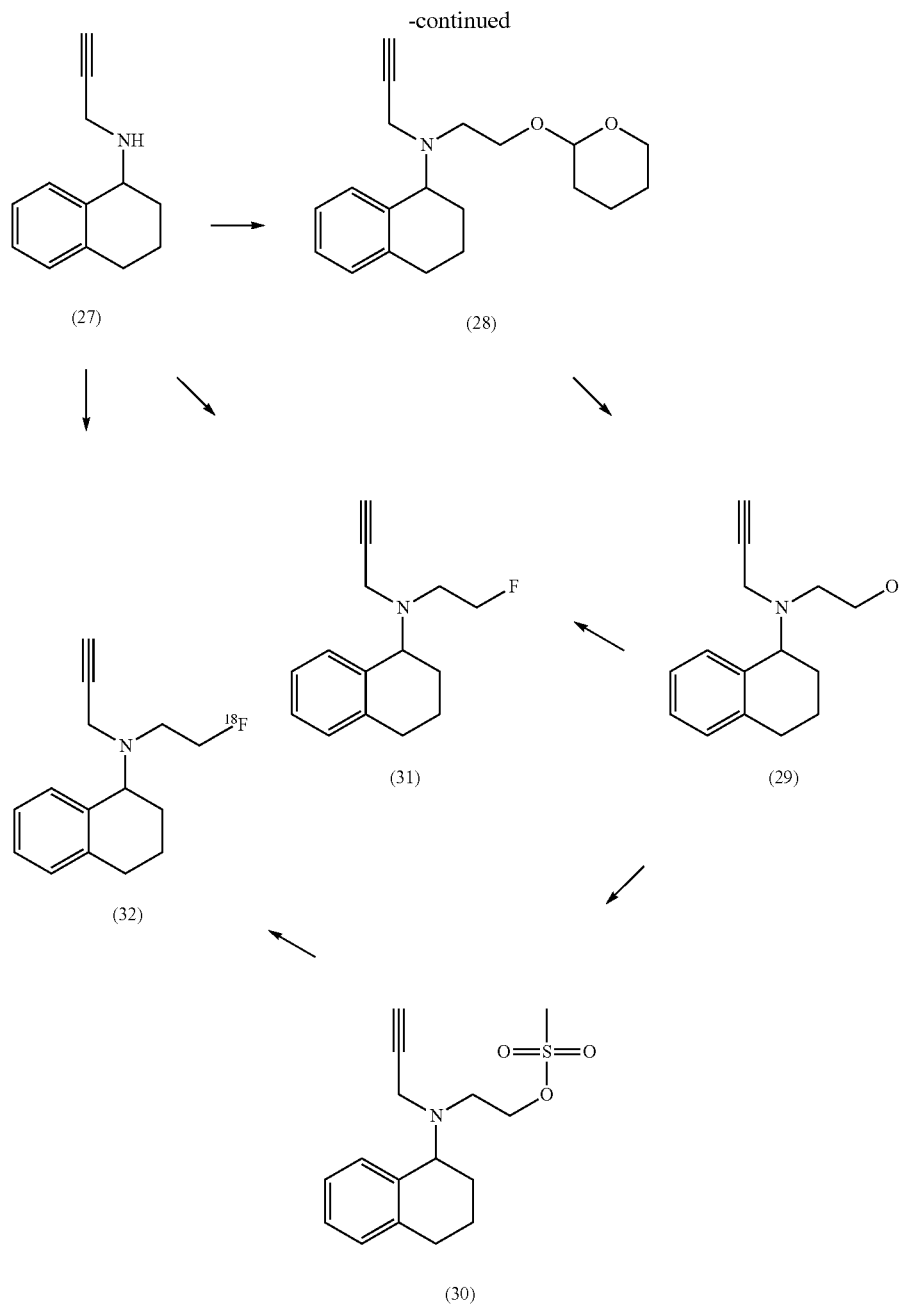

Compound 25 (Chem. Europ. J.; 11; 19; 2005; 5777-5785) is alkylated with sodium hydride as base in DMF by use of propargyl bromide (compare e.g. J. Org. Chem.; 71; 13; (2006); 5023-5026). Boc-protected amine 26 is deprotected with trifluoroacetic acid or other acids to obtain compound 27. This secondary amine (27) is alkylated with [F-18]-fluoro ethyl bromide (compare A6 scheme 1) obtaining compound (32). Compound 27 can also be alkylated by 2-(2-tetrahydropyranyloxy)-ethyl bromide (Aldrich) and potassium carbonate in DMF. The protection group (THP) is removed using acid (e.g. tosyl acid in dichloromethane) and then alcohol (29) is converted to mesylate 30 using mesylchloride and triethylamine in dichloromethane. Compound 30 is either converted in compound 31 or compound 32 by F-19 and F-18 fluorinating reagents. Optionally compound 29 can be converted into compound 31 by using DAST in dichloromethane.

Another example for the synthesis of compounds of Formula Ib is depicted in scheme 10: Compound 32 (J. Am. Chem. Soc.; EN; 129; 3; 2007; 562-568) is alkylated with propargyl bromide and sodium hydride in DMF (compare e.g. J. Org. Chem.; 71; 13; (2006); 5023-5026). The Tces and TBDMS groups are removed using Zn—Cu couple (J. Am. Chem. Soc.; 129; 3; 2007; 562-568) and hydrogen chloride. Secondary amine 34 is alkylated with methyl iodide in acetonitrile and sodium carbonate to obtain compound 35. The alcohol 35 is converted into the corresponding triflate 36 by use of trifluoromethylsulfonylchloride and triethyl amine as base. The triflate 36 is converted into [F-18]-fluoro derivative 37 using typical [F-18] fluorinating agents. Alcohol 35 can also be converted into fluoride 38 using nonafluorobutylsulfonyl fluoride in DBU (Tetrahedron Letters, Vol. 36, No. 15, pp. 2611-2614, 1995).

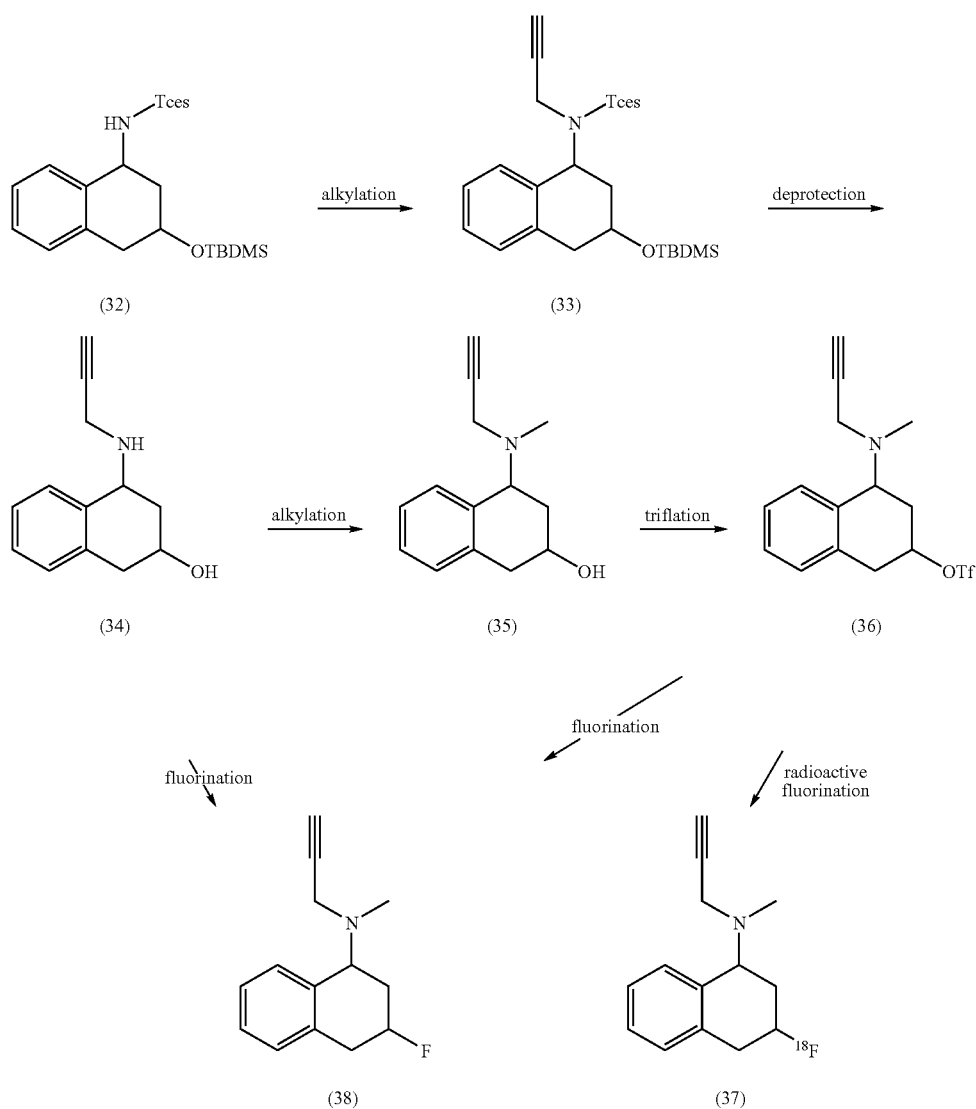

The aim of the present invention was to find an improved F-18 labelled compound in comparison to the current state of the art that can be used to detect reactive astrocytes by means of PET Imaging targeting monoamine oxidase B. As the data of the present invention demonstrate the afore mentioned [$^{18}$F]compound 13 surprisingly showed an improved metabolic stability when compared to [$^{11}$C]Deprenyl (compare compound 3) and compound 5 ([$^{18}$F]FHMP; Nuclear Medicine Biology, Vol. 26, pp 111-116, (1999).

Binding of the [$^{18}$F]compound 13 was investigated on human brain sections from patients with Alzheimer's disease and normal controls using a standard protocol In brief, the tissue was cut at a 18 μm thickness in a Cryostat (Leica, Germany), thaw mounted onto glass slides and kept at −20° C. for at least 48 hours before use. Thereafter, the slides were removed and brought to room temperature. The sections were washed in 25 mM HEPES buffer for 5 min, incubated with 10 Bq/μl [18F]compound 13 in 25 mM HEPES/0.1% BSA for 60 min at room temperature in a humidified chamber and washed again 5 times for 2 min each in 25 mM HEPES/0.1% BSA. The sections were dipped two times into ice cold distilled water, dried at room temperature and exposed to PhosphorI-manger plates (FUJI BAS 5000) over night. For detection of the specificity of the signals an excess (10 μM) of Deprenyl, Pargylin (both for MAO B) and Clorgyline (for MAO A), respectively, was used. After exposure, the sections were immunohistochemically stained using a standard protocol with an anti-GFAP antibody to detect reactive astrocytes. Amyloid 13 plaques were detected with BAY 949172 (Rowe C C et al. Lancet Neutol 2008; 7: 129-135) using the binding protocol as described above. The specificity of [$^{18}$F]compound 13 for MAO B is presented in FIGS. 1 and 2. FIGS. 3 and 4 demonstrate the relation of the radioactive signals to the underlying pathology, i.e. amyloid 13 plaques (FIG. 3) and reactive astrocytes (FIG. 4), respectively.

Biodistribution of [$^{18}$F]compound 13 was investigated in NMRI mice weighting 25-31.5 g at five time points. For each time point 3 mice have been used. The mice were injected each with 0.178 MBq[$^{18}$F]compound 13. After the respective time points the mice were sacrificed, the organs taken out and measured in a gamma counter. The results were decay corrected. The compound showed a high initial brain uptake of radioactivity (7.5±0.04% ID/g at 2 min p.i.) and a high initial elimination of radioactivity from the brain (2.10±0.33% ID/g at 30 min p.i.) with a decrease to 1.34±0.26% ID/g after 4 hours as shown in FIG. 5.

The [$^{18}$F]compound 13 has been tested in a cynomolgus monkey. 155 MBq [$^{11}$C]Deprenyl and 178 MBq [$^{18}$F]compound 13, respectively, have been injected into the same monkey. Time activity curves have been monitored by calculating the standard uptake values (SUV) as [$^{18}$F]compound 13 compared to the [$^{11}$C]compound. Plasma radioactivity profiles have been monitored over time. As can be seen from the comparison of the curves for the mother compound in FIGS. 8 and 9 the plasma radioactivity for [$^{18}$F]compound 13 was about double of that observed for [$^{11}$C]Deprenyl at the 30 and 45 min time points. In addition, metabolites occurring in plasma over time have been monitored (FIGS. 8 and 9) for both ligands. As can be seen from the comparison of FIG. 8 with FIG. 9 the [$^{18}$F]compound 13 is more stable than [$^{11}$C] Deprenyl. The generation of metabolite b levelled around 10% for [$^{18}$F]compound 13 compared to about 25% for [$^{11}$C] Deprenyl. For example, at the 30 min time point metabolite b was only one third as that observed for [$^{11}$C]Deprenyl. It is obvious that compound 13 is also more suited for in vivo imaging than compound 5 which has been reported to be degraded quickly towards a polar [$^{18}$F]-labelled metabolite.

The uptake and enrichment in specific regions, e.g. striatum, was about 10% higher for [$^{18}$F]compound 13 as compared to [$^{11}$C]Deprenyl (FIG. 10).

Further blocking experiments in monkeys show that staining in monkey brain is specific.

Preferred precursor molecules having formulae Ia are

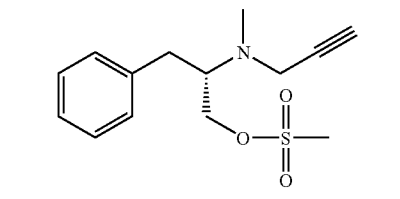

(2S)-2-[methyl(prop-2-yn-1-yl)amino]-
3-phenylpropyl methanesulfonate

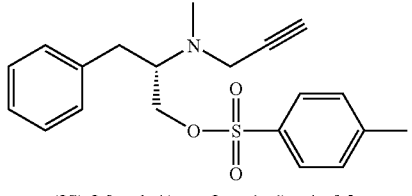

(2S)-2-[methyl(prop-2-yn-1-yl)amino]-3-
phenylpropyl 4-methylbenzenesulfonate

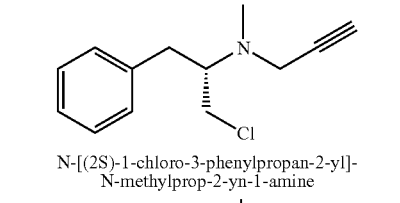

N-[(2S)-1-chloro-3-phenylpropan-2-yl]-
N-methylprop-2-yn-1-amine

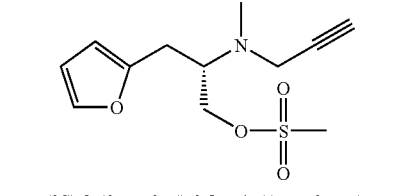

(2S)-3-(furan-2-yl)-2-[methyl(prop-2-yn-1-
yl)amino]propyl methanesulfonate

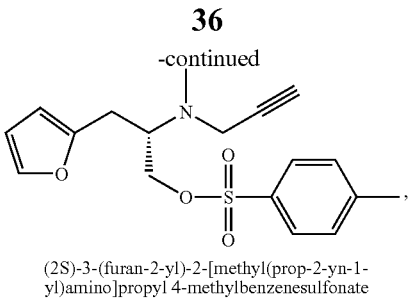

(2S)-3-(furan-2-yl)-2-[methyl(prop-2-yn-1-
yl)amino]propyl 4-methylbenzenesulfonate

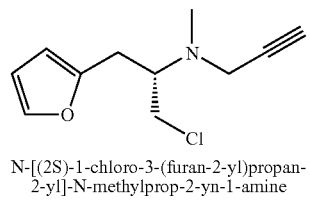

N-[(2S)-1-chloro-3-(furan-2-yl)propan-
2-yl]-N-methylprop-2-yn-1-amine

Preferred precursor molecules which are not covered by Formula Ib are

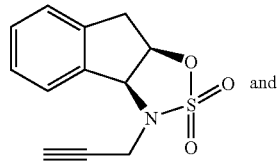

(3aS,8aR)-3-(prop-2-yn-1-yl)-3,3a,8,8a-tetrahydroindeno[1,2-d][1,2,
3]oxathiazole 2,2-dioxide

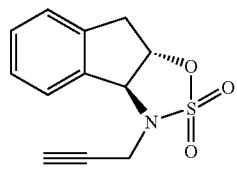

(3aS,8aS)-3-(prop-2-yn-1-yl)-3,3a,8,8a-tetrahydroindeno[1,2-d][1,2,
3]oxathiazole 2,2-dioxide Preferred examples of $^{18}$F-labelled compounds of formulae Ia or Ib are

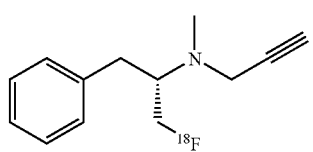

N-[(2S)-1-($^{18}$F)fluoro-3-phenylpropan-2-yl]-N-methylprop-2-yn-1-amine

37

-continued

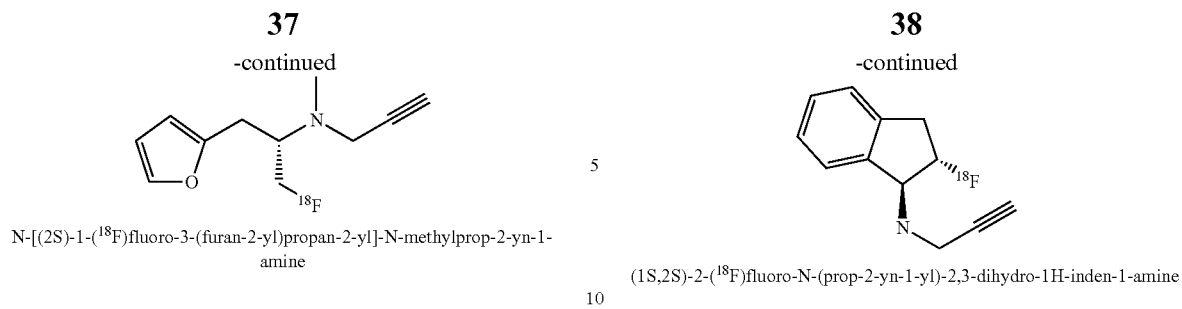

N-[(2S)-1-(¹⁸F)fluoro-3-(furan-2-yl)propan-2-yl]-N-methylprop-2-yn-1-amine

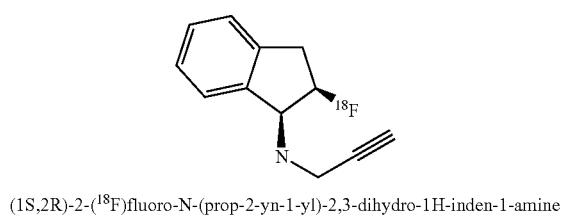

(1S,2R)-2-(¹⁸F)fluoro-N-(prop-2-yn-1-yl)-2,3-dihydro-1H-inden-1-amine

38

-continued (1S,2S)-2-(¹⁸F)fluoro-N-(prop-2-yn-1-yl)-2,3-dihydro-1H-inden-1-amine Compound 10 can be also converted to the mixture of fluorides 12 and 41 whereas compound 41 is a rearranged reaction product (scheme 11). Fluorides 12 and 41 can be separated on a column (compare TLC FIG. 15). The conversion of alcohol 10 with mesylchloride leads under certain circumstances to the mixture of chlorides 42 and 43 which is a suited pair of precursor compounds being radiofluorinated towards F-18 labelled compound 13 and 39. F-18 labelled products 13 and 39 are separable on HPLC column (compare FIG. 11 and FIG. 12) and can be investigated separately.

scheme 11

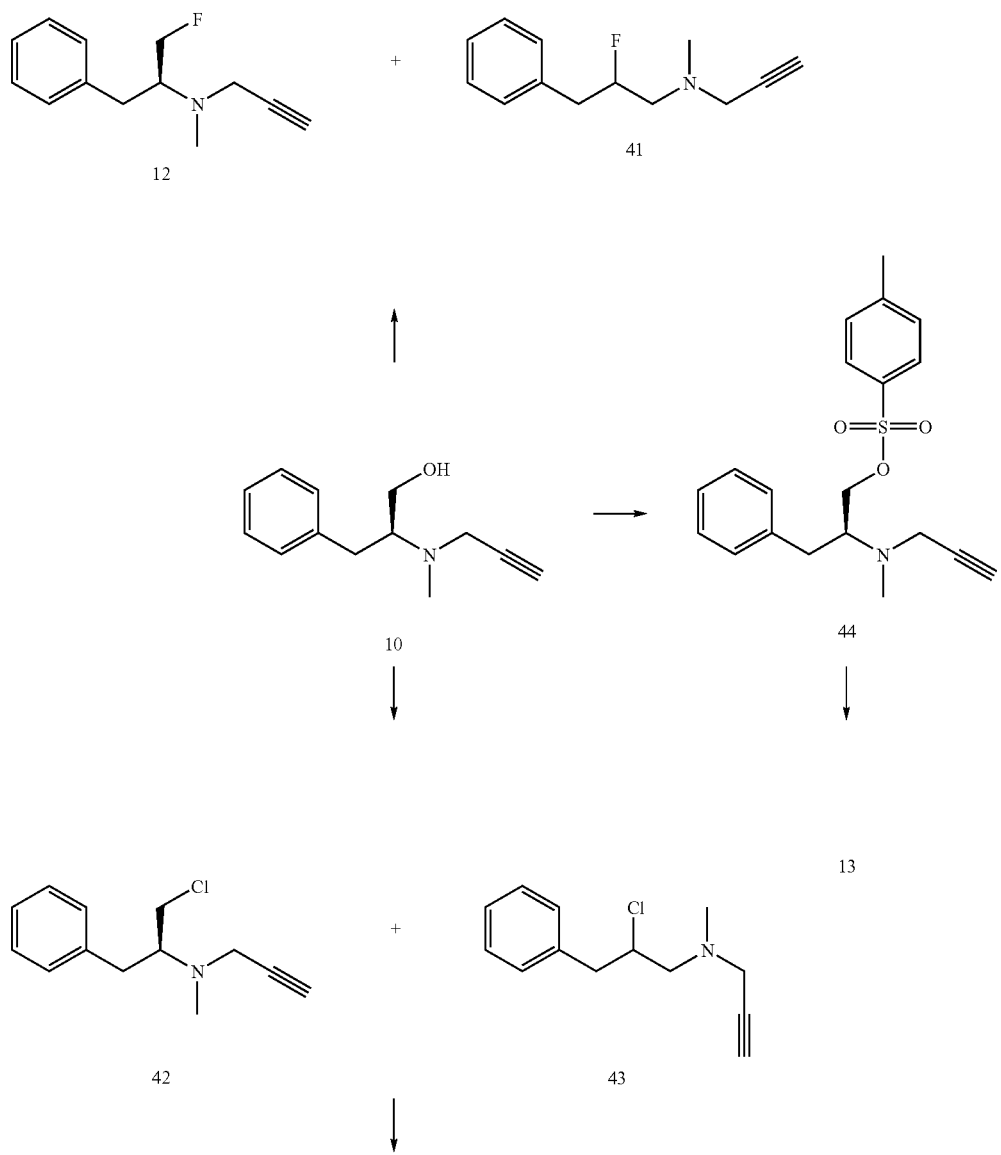

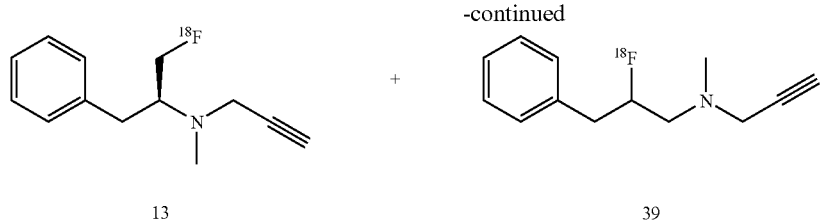

Alcohol 10 can be also converted to tosylate 44 using tosylanhydride. This derivative is also suited precursor for the radiolabeling towards compound 13.

Derivative 15 can be converted by using DAST towards compound 18 (compare scheme 12). The conversion of compound 15 towards chloride 45 is realized using mesylchloride. Chloride 45 is a suited precursor molecule for the radiofluorination towards compound 46 (compare FIG. 14).

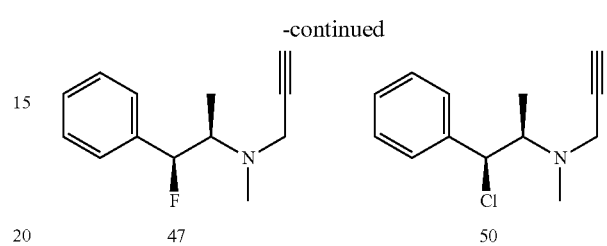

Compound 8 is the product of the radiofluorination of chloride 52. This precursor chloride is derived from alcohol 51 by use of mesylchloride. The cold reference compound (53) of F-18 labelled fluoride 8 is also shown in scheme 14 and can be synthesized from alcohol 51 using DAST.

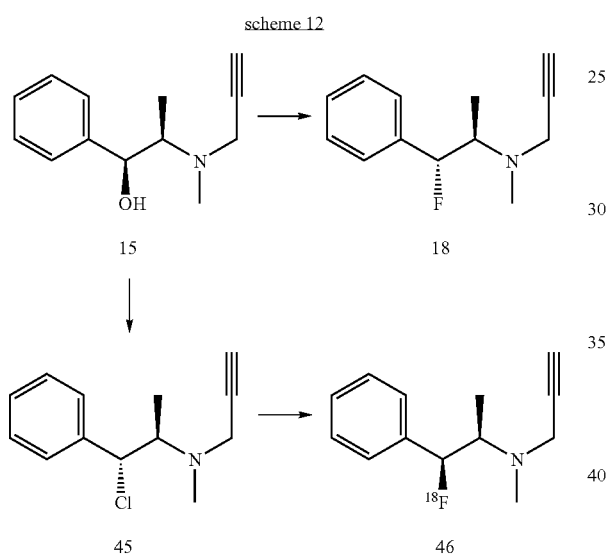

The diastereoisomer of compound 18 is compound 47 which is synthesized from (1R,2R)pseudoehedrine 48 in tow steps via alcohol 49 (see scheme 13). The conversion of alcohol 49 which is synthesized from (1R,2R)pseudoehedrine by alkylation with propargyl bromide towards fluoride 47 is realized by use of DAST. Compound 49 can also be converted to precursor molecule 50 by use of mesylchloride.

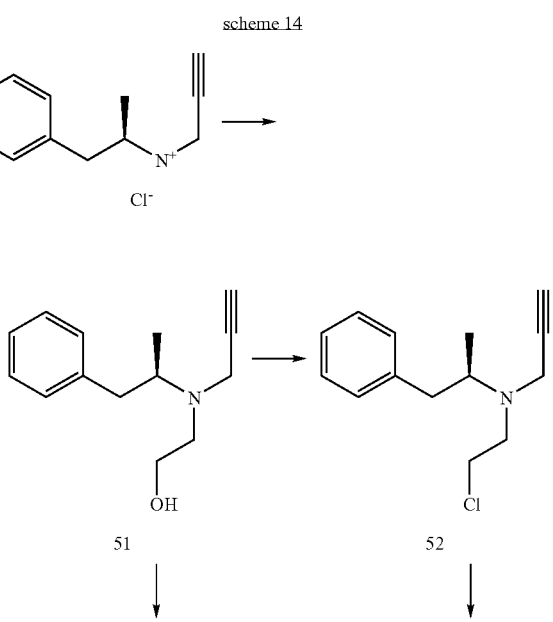

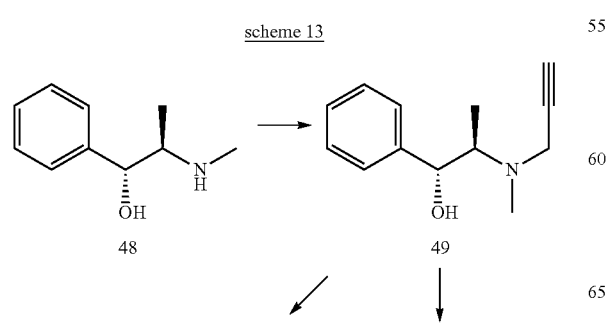

An example for the synthesis of a [F-18] labeled compound of formula Ib is described in scheme 15:

scheme 15

Amino alcohol 54 (commercially available) is converted to the sulfamidate 55 by use of SO$_2$Cl$_2$ (compare Tetrahedron Assymetry (1990), 1, 12, 877-880). The Mitsonobu reaction using prop-2-yn-1-ol, triphenylphosphin and, dipropan-2-yl (E)-diazene-1,2-dicarboxylate leads to the precursor compound 56 which then can be converted by [$^{18}$F]fluorination with tetrabutylammonium hydrodide and subsequent deprotection of the sufate moiety (compare F-19 analogue 57) towards compound 58. A similar approach is possible to obtain the corresponding F-19 derivative 59 (compare: Posakony et al. Synthesis (2002), 6, 766-770).

Further, the invention relates to

1. A compound of formula Ia formula Ia or formula Ib formula Ib wherein
W is selected from the group comprising
—C(U$^1$)(U$^2$)—C≡CH and cyclopropyl, U$^1$ and U$^2$ being independently selected from hydrogen and deuterium;
A is selected from the group comprising substituted or unsubstituted aryl, substituted or unsubstituted heteroaryl, such as furanyl, (C$_1$-C$_{10}$)alkyl, G$^4$-(C$_2$-C$_4$)alkynyl, G$^4$-(C$_1$-C$_4$)alkoxy, (G$^4$-(C$_1$-C$_4$)alkyl)aryl, (G$^4$-(C$_1$-C$_4$)alkoxy)aryl, (G$^4$-(C$_1$-C$_4$)alkyl)aryl, and (G$^4$-(C$_1$-C$_4$)alkoxy)aryl, wherein preferably said heteroaryl is furanyl,
G$^1$, G$^2$, G$^3$ and G$^4$ in formula Ia and formula Ib are independently and individually, at each occurrence, selected from the group comprising hydrogen, (C$_1$-C$_4$)alkyl, preferably methyl, L, and —(C$_1$-C$_6$)alkyl-L,
with the proviso that exactly one of G$^1$-G$^4$ in formula Ia are selected from L and —(C$_1$-C$_6$)alkyl-L, and
with the proviso that exactly one of G$^3$ and G$^4$ in formula Ib are selected from L and —(C$_1$-C$_6$)alkyl-L,
L being a leaving group, or L being F, preferably $^{18}$F or $^{19}$F, wherein, preferably, if L is $^{19}$F, said compound contains exactly one $^{19}$F-atom being attached to an sp$^3$-hybridized carbon atom,
wherein n is an integer from 0 to 6, preferably 1-3, more preferably 1-2,
and wherein m is an integer from 0 to 4, preferably 0 to 2, more preferably 0-1,
and wherein e and f are integer from 0 to 1, with the proviso that at least one of e and f is 1, including all isomeric forms of said compound, including but not limited to enantiomers and diastereoisomers as well as racemic mixtures,
and any pharmaceutically acceptable salt, ester, amide, complex or prodrug thereof.

2. The compound according to count 1, wherein W is —CH$_2$—C≡CH.

3. The compound according to any of counts 1-2, wherein A is selected from the group comprising substituted or unsubstituted phenyl, substituted or unsubstituted furanyl, in particular furan-2-yl, furan-3-yl, (C$_1$-C$_4$)alkyl, G$^4$-(C$_3$-C$_4$), alkynyl, G$^4$-(C$_1$-C$_3$)alkoxy, (G$^4$-(C$_1$-C$_3$)alkyl)phenyl, (G$^4$-(C$_1$-C$_3$)alkoxy)phenyl.

4. The compound according to count 3, wherein A is selected from the group comprising substituted or unsubstituted phenyl, substituted or unsubstituted furanyl, (G$^4$-(C$_1$-C$_3$)alkyl)phenyl, (G$^4$-(C$_1$-C$_3$)alkoxy)phenyl, hydroxy-phenyl, halo-phenyl, methoxy-phenyl, dimethoxy-phenyl, trifluormethyl-phenyl, and ((C$_1$-C$_4$)alkyl)-phenyl.

5. The compound according to count 4, wherein A is selected from the group comprising substituted or unsubstituted phenyl, (G$^4$-(C$_1$-C$_3$)alkoxy)phenyl, hydroxyl-phenyl, fluorophenyl, methoxyphenyl, and methylphenyl.

6. The compound according to any of the foregoing counts, wherein G$^1$, G$^2$, G$^3$ and G$^4$ in formula Ia, and G$^3$ and G$^4$ in formula Ib are independently and individually, at each occurrence, selected from the group comprising hydrogen, $(C_1$-$C_4)$alkyl, preferably methyl, L, and —$(C_1$-$C_4)$alkyl-L, with the proviso that exactly one of $G^1$-$G^4$ in formula Ia and exactly one of $G^3$-$G^4$ in formula Ib are selected from L and —$(C_1$-$C_4)$alkyl-L.

7. The compound according to count 6, wherein $G^1$, $G^2$, $G^3$ and $G^4$ in formula Ia, and $G^3$ and $G^4$ in formula Ib are independently and individually, at each occurrence, selected from the group comprising hydrogen, methyl, L, and —$(C_1$-$C_2)$alkyl-L, with the proviso that exactly one of $G^1$-$G^4$ in formula Ia and exactly one of $G^3$-$G^4$ in formula Ib are selected from L and —$(C_1$-$C_2)$alkyl-L.

8. The compound according to count 7, wherein $G^1$, $G^2$, $G^3$ and $G^4$ in formula Ia, and $G^3$ and $G^4$ in formula Ib are independently and individually, at each occurrence, selected from the group comprising hydrogen, methyl, L, and -methyl-L, with the proviso that exactly one of $G^1$-$G^4$ in formula Ia and exactly one of $G^3$-$G^4$ in formula Ib are selected from L and -methyl-L.

9. The compound according to any of the foregoing counts, wherein L is a leaving group selected from the group comprising halo, in particular chloro, bromo, iodo, mesyloxy, tosyloxy, trifluormethylsulfonyloxy, nona-fluorobutylsulfonyloxy, (4-bromo-phenyl)sulfonyloxy, (4-nitro-phenyl)sulfonyloxy, (2-nitro-phenyl)sulfonyloxy, (4-isopropyl-phenyl)sulfonyloxy, (2,4,6-tri-isopropyl-phenyl)sulfonyloxy, (2,4,6-trimethyl-phenyl)sulfonyloxy, (4-tertbutyl-phenyl)sulfonyloxy, and (4-methoxy-phenyl)sulfonyloxy.

10. The compound according to count 9, wherein L is selected from the group comprising chloro, bromo, mesyloxy, tosyloxy, trifluormethylsulfonyloxy, (4-bromo-phenyl)sulfonyloxy, (4-nitro-phenyl)sulfonyloxy, (4-isopropyl-phenyl)sulfonyloxy, and (2,4,6-tri-isopropyl-phenyl)sulfonyloxy.

11. The compound according to any of the foregoing counts which is

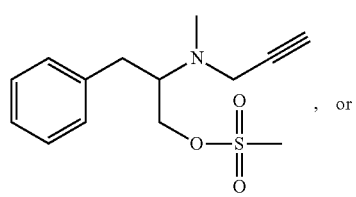

, or

Methanesulfonic acid 2-(methyl-prop-2-ynyl-amino)-3-phenyl-propyl ester

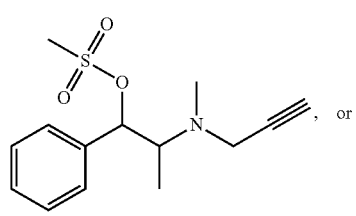

, or

Methanesulfonic acid 2-(methyl-prop-2-ynyl-amino)-1-phenyl-propyl ester

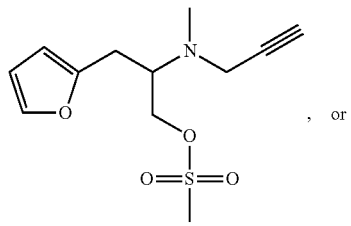

, or

Methanesulfonic acid 3-furan-2-yl-2-(methyl-prop-2-ynyl-amino)-propyl-ester

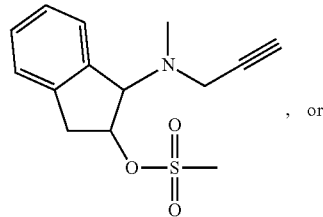

, or

Methanesulfonic acid 1-(methyl-prop-2-ynyl-amino)-indan-2-yl ester

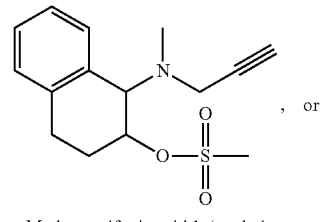

, or

Methanesulfonic acid 1-(methyl-prop-2-ynyl-amino)-1,2,3,4-tetrahydro-naphthalen-2-yl ester

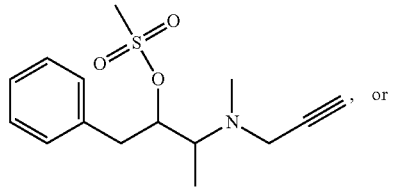

, or

Methanesulfonic acid 1-benzyl-2-(methyl-prop-2-ynyl-amino)-propyl ester

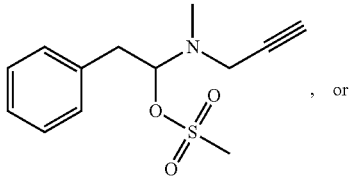

, or

Methanesulfonic acid 1-(methyl-prop-2-ynyl-amino)-2-phenyl-ethyl ester

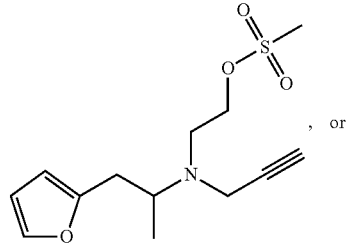

, or

Methanesulfonic acid 2-[(2-furan-2-yl-1-methyl-ethyl)-prop-2-ynyl-amino]-ethyl ester -continued

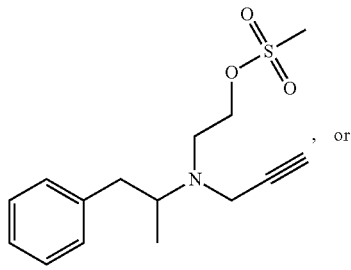

Methanesulfonic acid 2-[(1-methyl-2-phenyl-ethyl)-prop-2-ynyl-amino]-ethyl ester

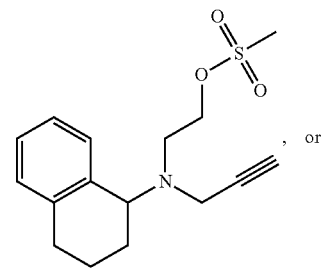

Methanesulfonic acid 2-[prop-2-ynyl-(1,2,3,4-tetrahydro-naphthalen-1-yl)-amino]-ethyl ester

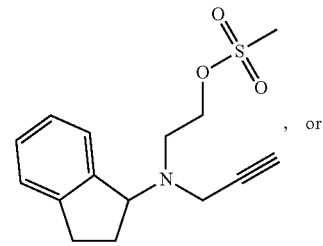

Methanesulfonic acid 2-(indan-1-yl-prop-2-ynyl-amino)-ethyl ester

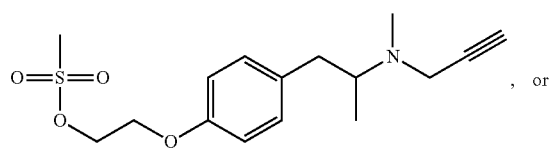

Methanesulfonic acid 2-{4-[2-(methyl-prop-2-ynyl-amnio)-propyl]-phenoxy}-ethyl ester

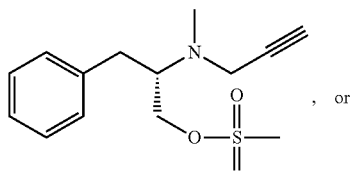

(2S)-2-[methyl(prop-2-yn-1-yl)amino]-3-phenylpropyl methanesulfonate

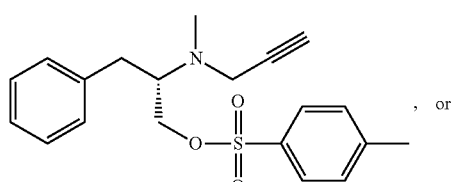

(2S)-2-[methyl(prop-2-yn-1-yl)amino]-3-phenylpropyl 4-methylbenzenesulfonate

-continued

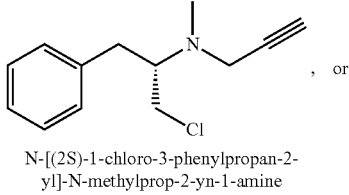

N-[(2S)-1-chloro-3-phenylpropan-2-yl]-N-methylprop-2-yn-1-amine

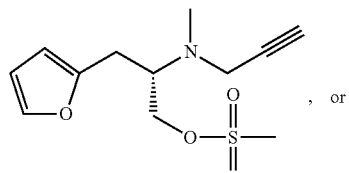

(2S)-3-(furan-2-yl)-2-[methyl(prop-2-yn-1-yl)amino]propyl methanesulfonate

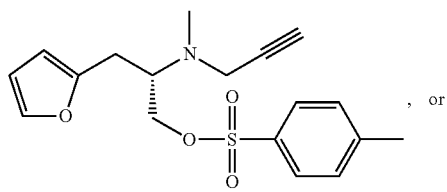

(2S)-3-(furan-2-yl)-2-[methyl(prop-2-yn-1-yl)amino]propyl 4-methylbenzenesulfonate

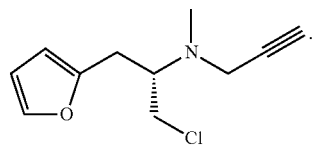

N-[(2S)-1-chloro-3-(furan-2-yl)propan-2-yl]-N-methylprop-2-yn-1-amine

12. The compound according to any of counts 1-10 wherein L is not F, in particular not $^{18}$F and not $^{19}$F.

13. The compound according to any of counts 1-11, wherein L is $^{18}$F, or wherein the mesyloxy-group, chloro-group and tosyloxy-group shown in any of the compounds of count 11, is replaced by $^{18}$F.

14. The compound according to any of counts 1-11, wherein L is $^{19}$F, or wherein the mesyloxy-group, chloro-group and tosyloxy-group shown in any of the compounds of count 11, is replaced by $^{19}$F.

15. A method of synthesis of a compound as defined in count 13 or count 14, in which a compound according to count 9 or 12 is reacted with an F-fluorinating agent, wherein F=$^{18}$F or $^{19}$F.

16. The method according to count 15, wherein said F-fluorinating agent is a compound comprising F-anions, preferably a compound selected from the group comprising 4, 7, 13, 16, 21, 24-hexaoxa-1,10-diazabicyclo[8.8.8]-hexacosane K F, i.e. crownether salt Kryptofix KF, KF, HF, KH F₂, CsF, NaF and tetraalkylammonium salts of F, such as [¹⁸F]tetrabutylammonium fluoride, and wherein F=¹⁸F or ¹⁹F.

17. A method of synthesis of a compound as defined in count 13 or count 14, comprising the steps:
F-fluorinating a compound of formula V formula V

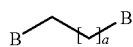

with an F-fluorinating agent to yield a compound of formula IV, formula IV

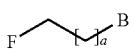

substituting said compound of formula IV with a compound of formula VI formula VI

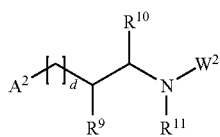

wherein F is ¹⁸F or ¹⁹F,
a is an integer from 0 to 4, preferably from 0 to 2, more preferably from 0 to 1,
B is a leaving group, preferably halo, in particular chloro, bromo, iodo, mesyloxy, tosyloxy, trifluormethylsulfonyloxy, nona-fluorobutylsulfonyloxy, (4-bromo-phenyl)sulfonyloxy, (4-nitro-phenyl)sulfonyloxy, (2-nitro-phenyl)sulfonyloxy, (4-isopropyl-phenyl)sulfonyloxy, (2,4,6-triisopropyl-phenyl)sulfonyloxy, (2,4,6-trimethyl-phenyl)sulfonyloxy, (4-tertbutyl-phenyl)sulfonyloxy, and (4-methoxy-phenyl)sulfonyloxy,
and wherein W² is W as defined in any of counts 1-2,
wherein A² is selected from the group comprising R¹²—O-aryl, R¹²—O-heteroaryl, aryl, heteroaryl, such as furanyl, $(C_1-C_{10})$alkyl, $(C_2-C_4)$alkynyl, $(C_1-C_4)$alkoxy, $((C_1-C_4)$alkoxy)aryl, $((C_1-C_4)$alkyl)aryl,
wherein R⁹ and R¹⁰ are independently and individually, at each occurrence, selected from the group comprising $(C_1-C_6)$alkyl and hydrogen,
wherein R¹¹ is selected from the group comprising $(C_1-C_6)$ alkyl and R¹²,
wherein R¹² is hydrogen,
wherein d is an integer from 0 to 4, preferably from 0-2, more preferably from 0-1, and
wherein said F-fluorinating agent is as defined in count 16, and wherein F=¹⁸F or ¹⁹F,
with the proviso that compounds of formula VI contain exactly one R¹².

18. The method according to count 17, wherein B is selected from the group comprising iodo, bromo, chloro, mesyloxy, tosyloxy, trifluormethylsulfonyloxy, and nona-fluorobutylsulfonyloxy.

19. The method according to any of counts 17-18, wherein A² is selected from the group comprising R¹²—O-phenyl, phenyl, furanyl, $(C_1-C_4)$alkyl, $(C_3-C_4)$alkynyl, $(C_1-C_3)$ alkoxy and substituted phenyl, more preferably from the group comprising R¹²—O-phenyl, phenyl, furanyl, $((C_1-C_3)$alkoxy)phenyl, hydroxyphenyl, halo-phenyl, methoxyphenyl, dimethoxy-phenyl, trifluormethyl-phenyl and $((C_1-C_4)$alkyl)phenyl, even more preferably from the group comprising R¹²—O-phenyl, phenyl, furanyl, hydroxyphenyl, fluoro-phenyl, methoxy-phenyl, and methyl-phenyl.

20. The method according to any of counts 17-19, wherein R⁹ and R¹⁰ are independently and individually, at each occurrence, selected from the group comprising $(C_1-C_4)$alkyl and hydrogen, preferably from the group comprising methyl and hydrogen.

21. The method according to any of counts 17-20, wherein R¹¹ is selected from the group comprising $(C_1-C_4)$alkyl and R¹², preferably from the group comprising methyl and R¹².

22. A composition comprising a compound according to any of counts 1-14 and a pharmaceutically acceptable carrier or diluent.

23. The composition according to count 22, wherein said compound is a compound according to count 13.

24. The composition according to count 22, wherein said compound is a compound according to count 14.

25. The composition according to count 22, wherein said compound is a compound according to count 12.

26. A compound according to any of counts 1-14, preferably a compound according to count 13 or 14, or a composition according to any of counts 22, 23, 24 or 25 for use as a pharmaceutical or diagnostic agent or imaging agent.

27. Use of a compound according to any of counts 1-14, preferably a compound according to count 13 or 14, or a composition according to any of counts 22, 23, 24 or 25 for the manufacture of a medicament for the treatment and/or diagnosis and/or imaging of diseases of the central nervous system (CNS).

28. A compound according to count 13 or a composition according to count 23 for use as a diagnostic agent or imaging agent, in particular for diseases of the central nervous system.

29. A kit comprising a sealed vial containing a predetermined quantity of a compound according to
a) count 12 or
b) formula V and VI, as defined in any of counts 17-21.

30. A method for detecting the presence of monoamine oxidase in a patient's body, preferably for imaging a disease of the central nervous system in a patient, comprising:
introducing into a patient's body a detectable amount of a compound according to count 13 or a composition according to count 23,
and detecting said compound or said composition by positron emission tomography (PET).

31. A method of treatment of a disease of the central nervous system comprising the step of introducing into a patient a suitable quantity of a compound according to any of counts 1-14, preferably of a compound according to count 13 or 14.

DESCRIPTION OF THE FIGURES

FIG. 14: Analytical chromatogram of compound 40 on reverse phase HPLC on a µ-Bondapak C-18 column (300×3.9 mm, 10 µm; waters instruments) and MeCN—H$_3$PO$_4$ (0.01 M) (15:85 v/v) was used as the eluting solvent at a flow rate of 2 mL/min. The eluate was monitored by a UV absorbance detector (λ=214 nm) in series with a radioactivity detector (β-flow; Beckman, Fullerton, Calif.).

EXPERIMENTAL

Figure 1:
FIG. 1: Autoradiography using [¹⁸F]compound 13 on human brain slices from four brains from patients with diagnosis of Alzheimer's disease. (A) Autoradiographic signal after exposure on the PhosphorImager plate. Note the black dots in the tissue slices corresponding to areas with amyloid β plaques (see examples in FIG. 3). (B) and (C) the signals could be blocked with deprenyl and pargylin, respectively, showing the specificity of [$^{18}$F]compound 13 for MAO B.
Figure 2:
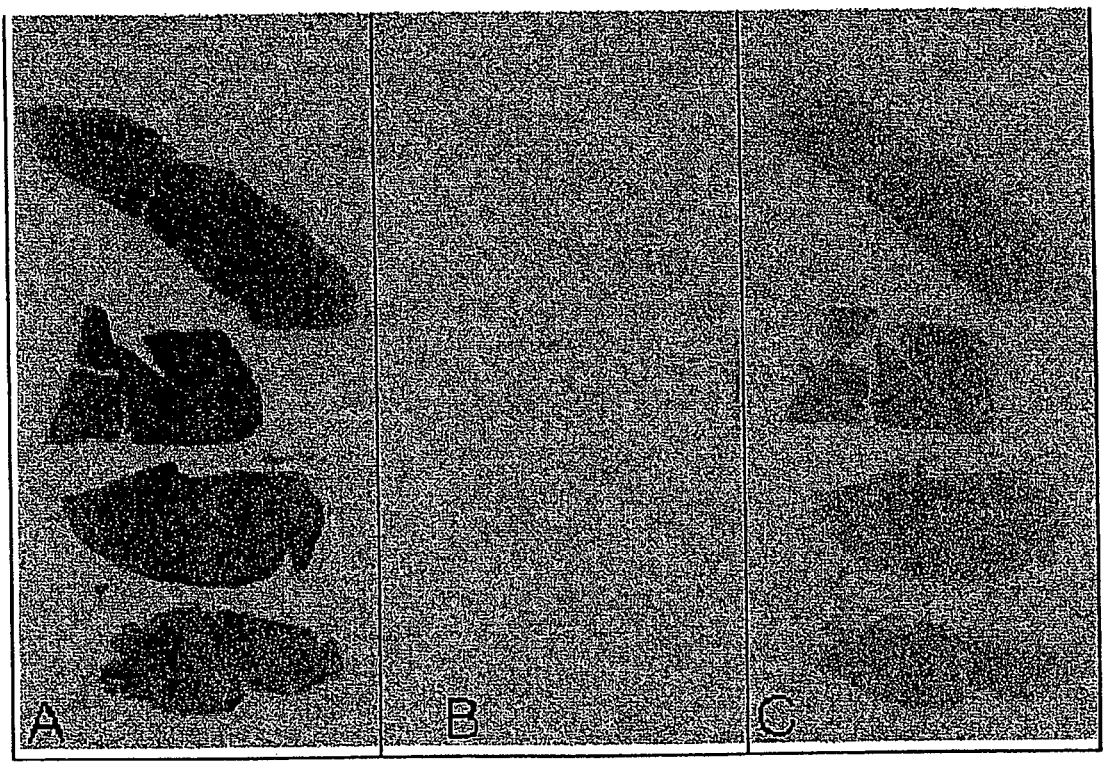
FIG. 2: Autoradiography using [$^{18}$F]compound 13 on human brain slices from four brains from patients with diagnosis of Alzheimer's disease. (A) Autoradiographic signal after exposure on the PhosphorImager plate. Note the black dots in the tissue slices corresponding to areas with amyloid β plaques (see examples in FIG. 3). (B) the signals could be completely blocked with deprenyl but not with clorgyline (MAO A inhibitor) as seen in (C), showing the specificity of [$^{18}$F]compound 13 for MAO B.
Figure 3A:
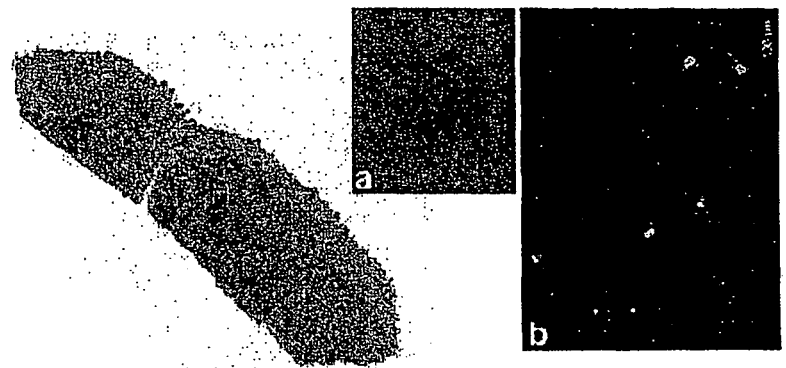
FIG. 3: Tissue samples from three brains from patients with Alzheimer's disease which were processed for [$^{18}$F]compound 13 autoradiography and subsequently for binding with the amyloid detecting substance BAY 949172. (A) and (B) the square marked in the brain slice is shown in higher magnification in (a) and (b) demonstrates the underlying amyloid β pathology. (C) two squares, (a) and (b), are marked in the brain slice and are shown in higher magnification in (a') and (b'). (c) and (d) represent the amyloid β pathology in the regions shown in higher magnification. Note that the signal density and intensity corresponds with the amyloid β plaque load. The square (b) is devoid of specific signals in the autoradiography did also not show BAY 949172 binding (d).
Figure 3B:
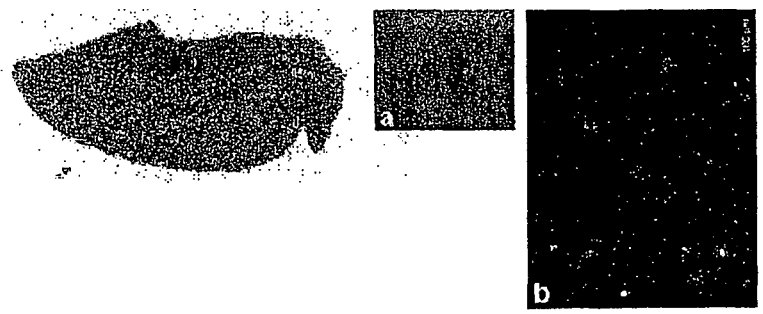
Figure 3C:
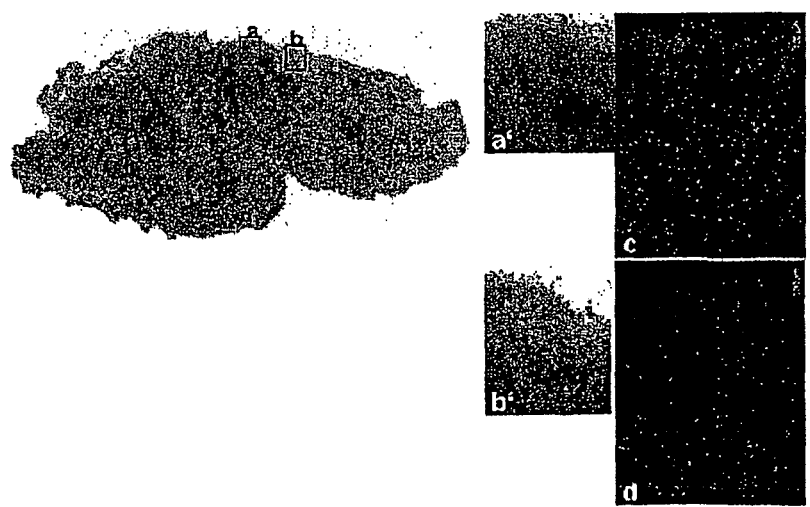
Figure 4:
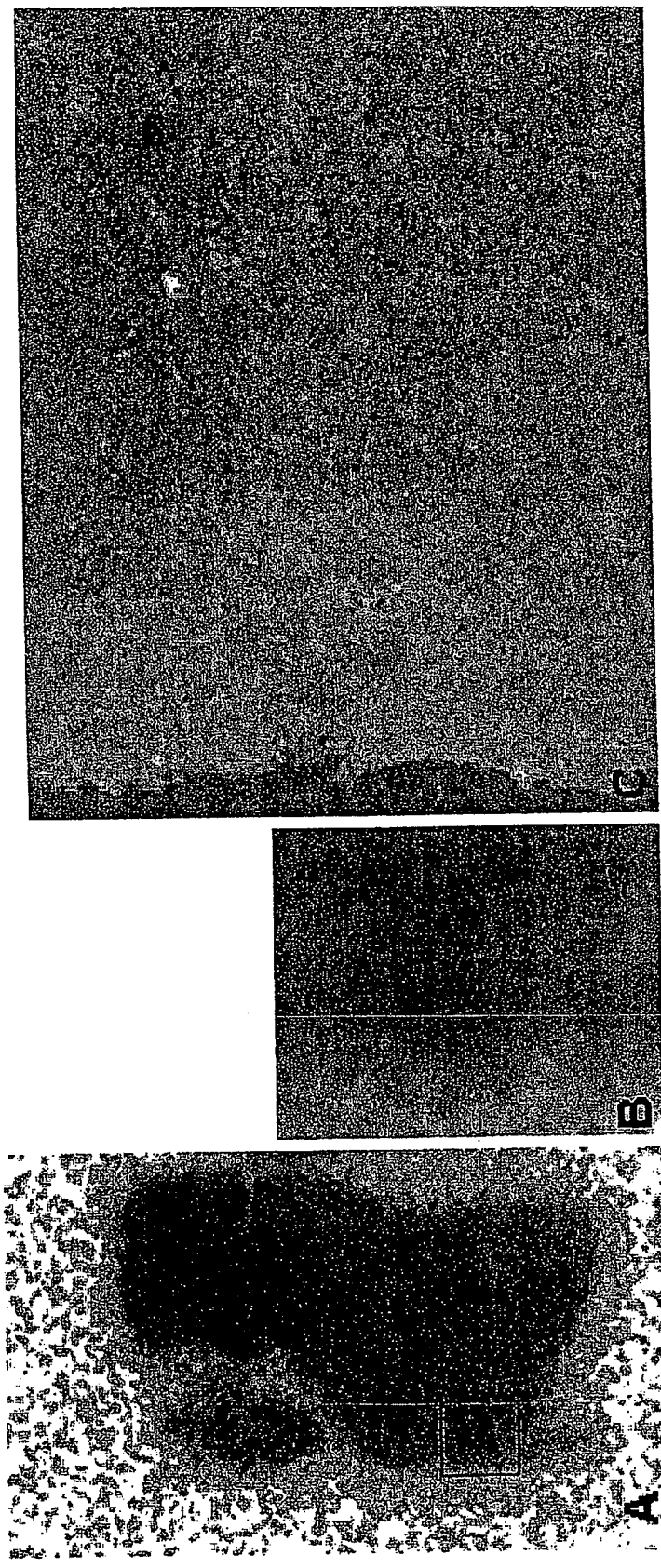
FIG. 4: The correspondence of the autoradiographic signal to reactive astrocytes is demonstrated. (A) On a human brain slice from a patient with AD [$^{18}$F]compound 13 binding is shown. (B) The square marked in A is shown in higher magnification. In this area immunoreactivity for GFAP, showing reactive astrocytes, is demonstrated in (C).
Figure 5:
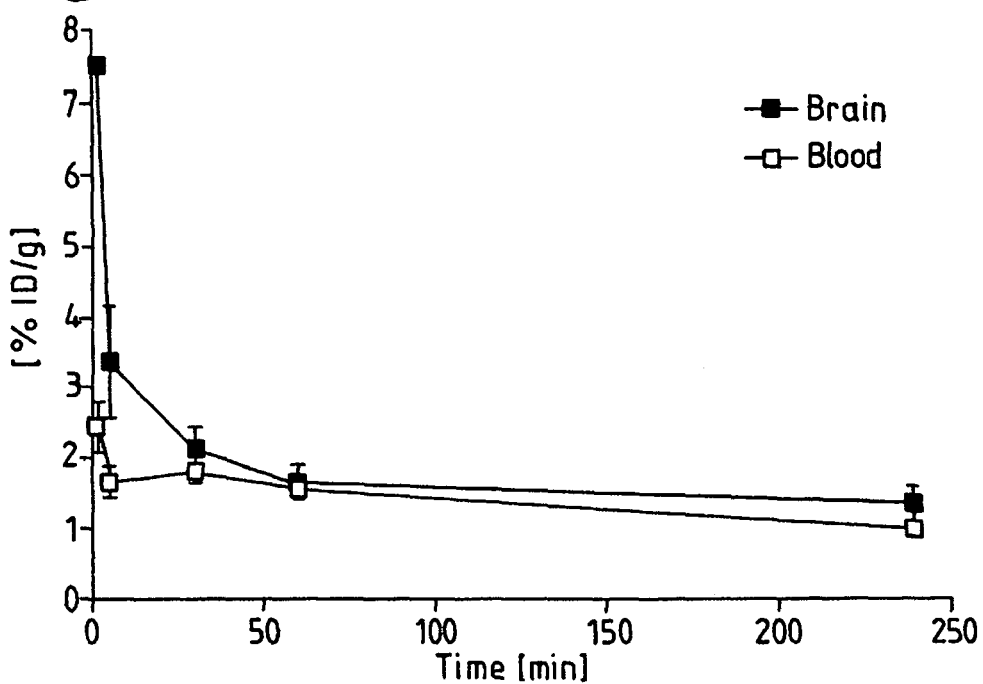
FIG. 5: Distribution of [$^{18}$F]compound 13 detected via a gamma-detector is shown in a time frame of 4 hours for brain and blood.
Figure 6:
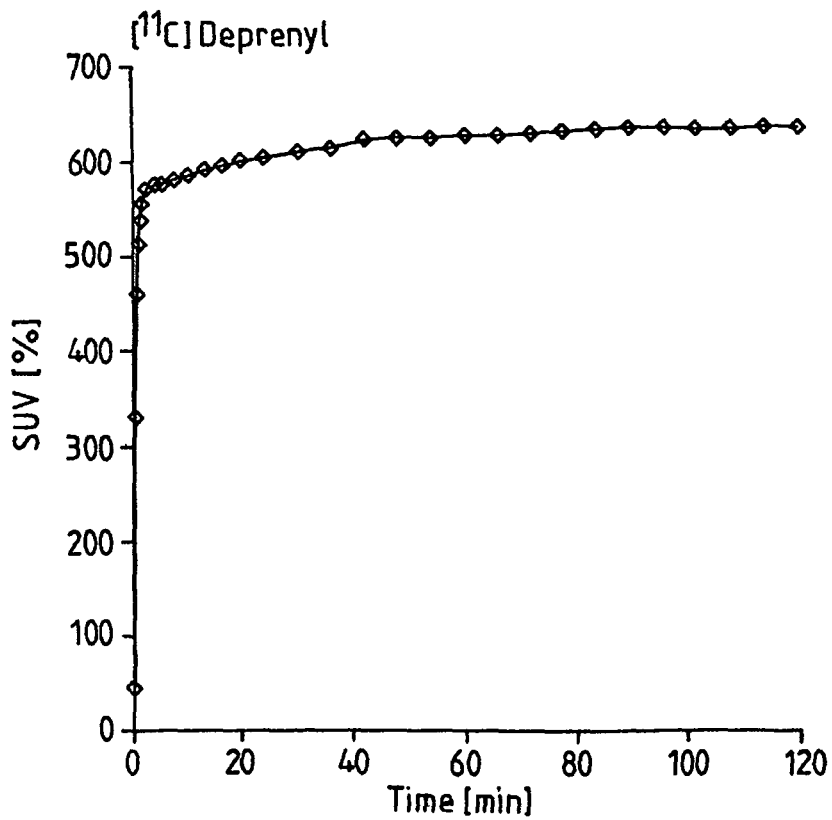
FIG. 6: The time activity curve for [$^{11}$C]Deprenyl (C-11 labelled compound 3) in the btrain of the cynomolgus monkey expressed in standard uptake values (SUV %) over a time of 120 min is shown.
Figure 7:
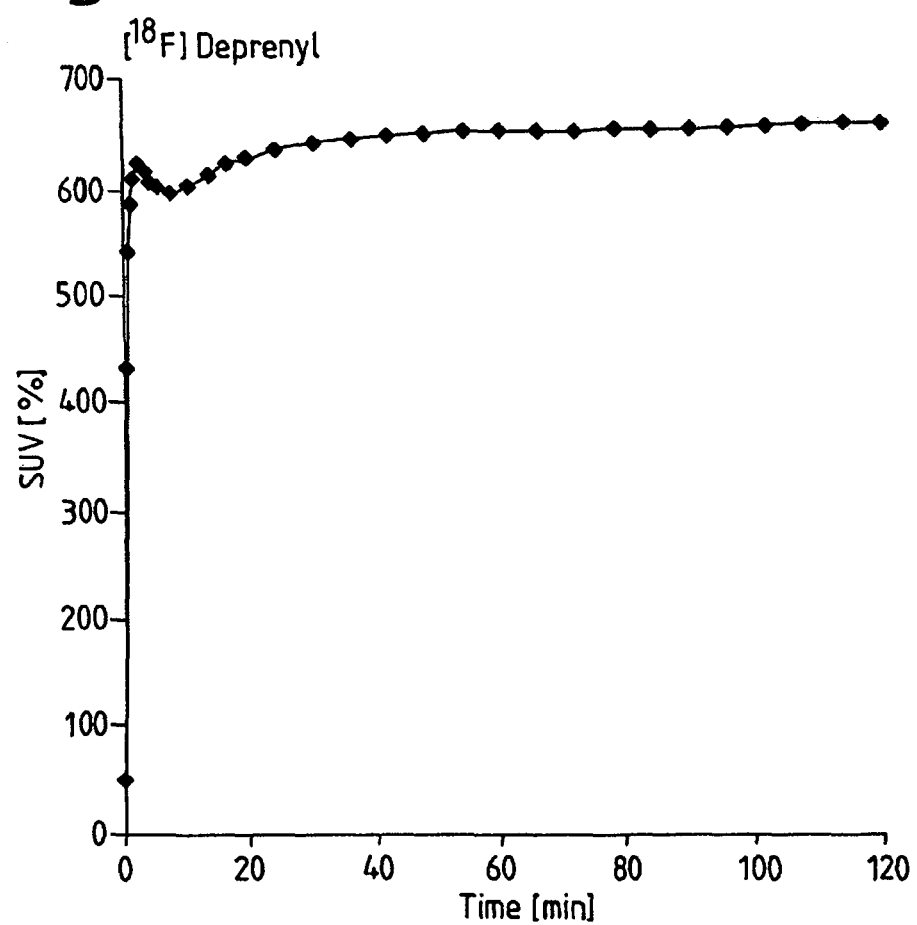
FIG. 7: The time activity curve [$^{18}$F]compound 13 in the btrain of the cynomolgus monkey expressed in standard uptake values (SUV %) over a time of 120 min is shown.
Figure 8:
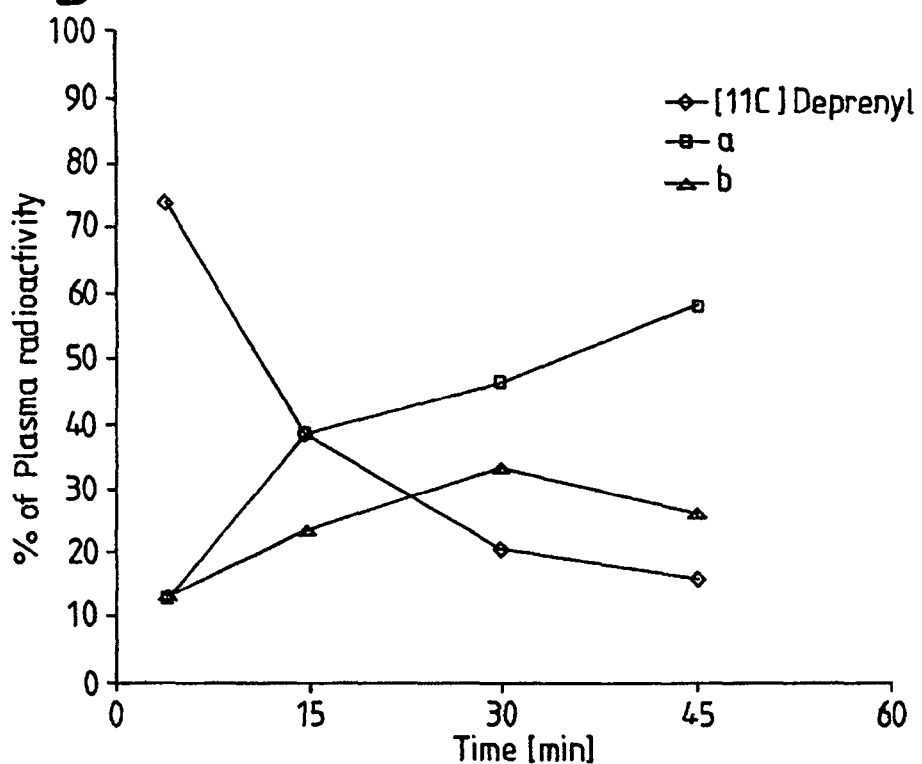
FIG. 8: Demonstration of in vivo metabolism of [$^{11}$C] Deprenyl (C-11 labelled compound 3) in the cynomolgus monkey. The mother compound [$^{11}$C]Deprenyl (C-11 labelled compound 3) as well as metabolites a and b are shown.
Figure 9:
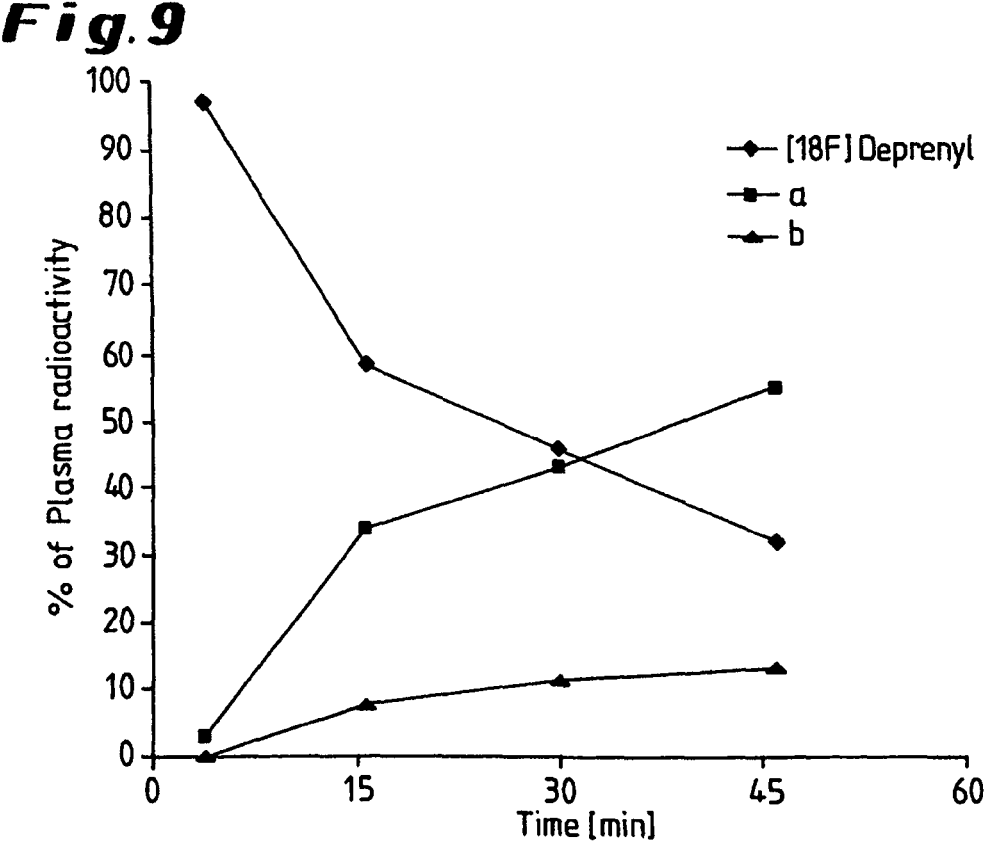
FIG. 9: Demonstration of in vivo metabolism of [$^{18}$F] compound 13 in the cynomolgus monkey. The mother compound (C-11 labelled compound 3) as well as metabolites a and b are shown.
Figure 10:
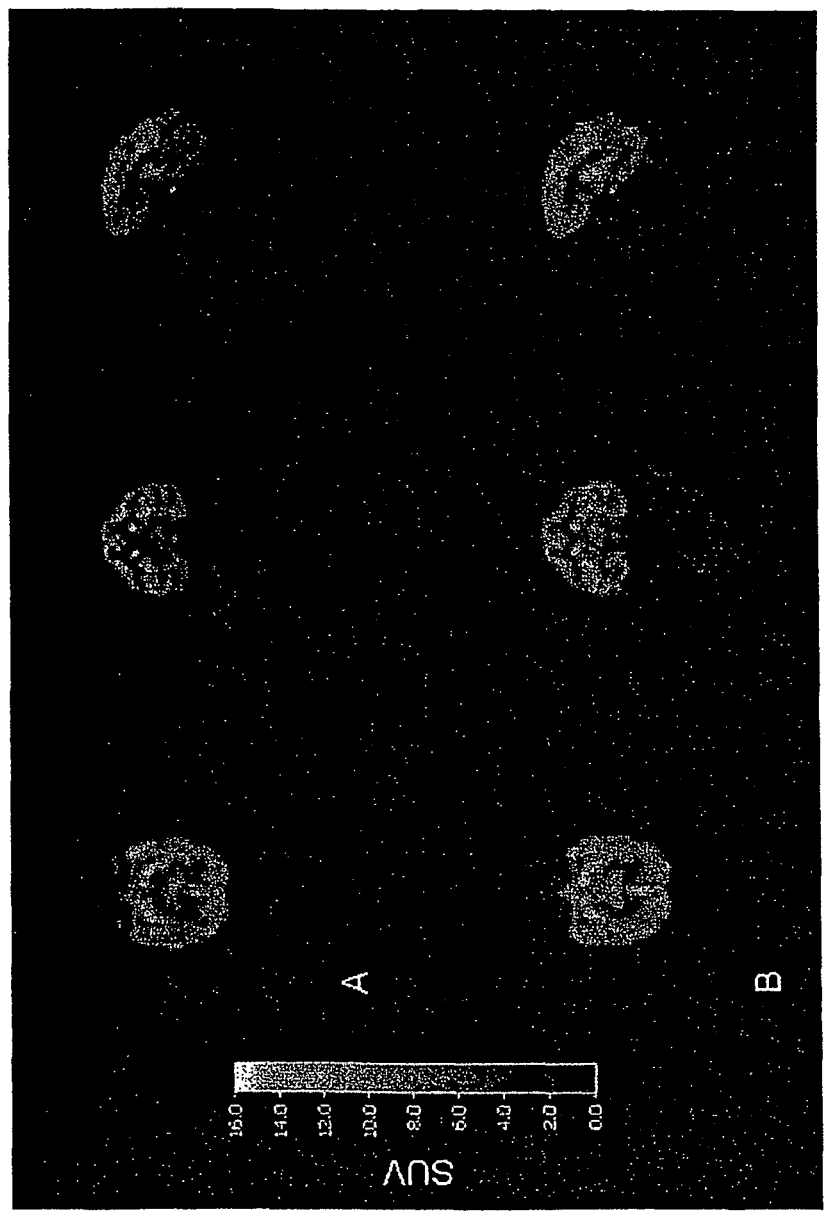
FIG. 10: Images of three planes (transversal, coronal and saggital) of the brain of the same cynomolgus monkey after the injection of (A) [$^{11}$C]Deprenyl (C-11 labelled compound 3) and (B) [$^{18}$F]compound 13. (C) Time activity curves for (a) [$^{11}$C]Deprenyl (C-11 labelled compound 3) and (b) [$^{18}$F] compound 13 in the striatum and cerebellum of the monkey brain.

General Procedures:
A: Fluorination with Non-radioactive [F-19] Fluoride

To a solution of 0.25 mmol starting material in 0.5 ml acetonitril 16 mg (0.27 mmol) potassium fluoride and 104 mg (1.1 eq.) kryptofix are added. The reaction mixture is heated by microwave (130° C., 15 min) and cooled to room temperature again. The reaction mixture is diluted with 10 ml diethyl ether and 10 ml water. The organic phase is separated. The aqueous phase is extracted three times with 10 ml diethyl ether. The combined organic phases are washed with brine and dried with magnesium sulfate. The solvent is evaporated and the residue is purified by column chromatography with ethyl acetate-hexane gradient.

B: Fluorination with Radioactive [F-18] Fluoride

To a Wheaton vial (5 ml) charged with 2.5 mg Kryptofix (2.2.2Kryptand) in 0.75 ml acetonitrile and 0.5 mg potassium carbonate and the fluorine containing water (0.5-2.5 GBq, 200-300 µl) is added. The solvent is removed by heating at 120° C. for 10 mins under a stream of nitrogen. Anhydrous MeCN (1 ml) is added and evaporated as before. This step is repeated again. A solution of starting material (2 mg) in 0.70 ml anhydrous MeCN is added. After heating at 110° C. for 30 min. The crude reaction mixture is analyzed using analytical HPLC: ACE3-C18 50 mm×4.6 mm; solvent gradient: start 5% acetonitril-95% acetonitril in water in 7 min., flow: 2 ml/min. The desired F-18 labeled product is confirmed by co-injection with the corresponding non-radioactive F-19 fluoro-standard on the analytical HPLC. The crude product (50-400 MBq) is purified by preparative HPLC column: The desired product is obtained (15-200 MBq) as reconfirmed by co-injection with the non-radioactive F-19 fluoro standard on the analytical HPLC.

C: Fluorination with [F-18] Fluoride

A solution of [$^{18}$F]fluoride in [$^{18}$O] enriched water was flashed through a Sep-Pak QMA light cartridge (preconditioned with K$_2$CO$_3$ [0.5 M, 10 mL], 18 MΩ H2O, 15 mL) to isolate [$^{18}$F]fluoride which was then eluted from the cartridge with a solution of $K_2CO_3$ (7 µmol), Kryptofix 2.2.2 (130 µmol) in water (18 MΩ, 43 µL) and acetonitrile (2 mL). The solvent was evaporated at 160° C. under continues nitrogen flow and a yellow residue of $[^{18}F]F^-/K_2CO_3/K_{2.2.2}$ was left. The residue was then cooled to 25° C. and the precursor (~0.01 mmol, 2 mg) in DMSO (600 µL) was added. The closed reaction vessel was heated at 120° C. for 20 min and cooled down to room temperature. The reaction mixture was generally diluted with water to a total volume of 5 mL before HPLC purification.

E.g., F-18 labelled compounds 13, 39, 8 and 40 were also purified by reverse phase HPLC on a µ-Bondapak C-18 column (300×7.8 mm, 10 µm; waters instruments) and MeCN—$H_3PO_4$ (0.01 M) (15:85 v/v) was used as the eluting solvent at a flow rate of 4 mL/min (compare FIGS. 11, 12, 13 and 14). The eluate was monitored by a UV absorbance detector (λ=214 nm) in series with a GM tube radioactivity detector. The fraction of the desired compounds were collected and evaporated to dryness. The residue was dissolved in sterile disodiumphosphate phosphate buffered saline (PBS; pH=7.4; 10 mL) and filtered through a sterile filter (0.22 µm; Millipore, Bedford, Mass.), yielding a sterile and pyrogenic solution of $[^{18}F]$radioligand. The radiochemical purity of each radioligand was analyzed by a reverse phase HPLC on a µ-Bondapak C-18 column (300×3.9 mm, 10 µm; waters instruments) and MeCN—$H_3PO_4$ (0.01 M) (15:85 v/v) was used as the eluting solvent at a flow rate of 2 mL/min. The eluate was monitored by a UV absorbance detector (λ=214 nm) in series with a radioactivity detector (β-flow; Beckman, Fullerton, Calif.). The radiochemical purity was >99% for all three compounds. Alternatively the collected HPLC fraction was diluted with 40 ml water and immobilized on a Sep-Pak Plus C18 cartridge (Waters), which was washed with 5 ml water and eluted with 1 ml ethanol to deliver the product in a radiochemical purity>99% as well.

Figure 11:
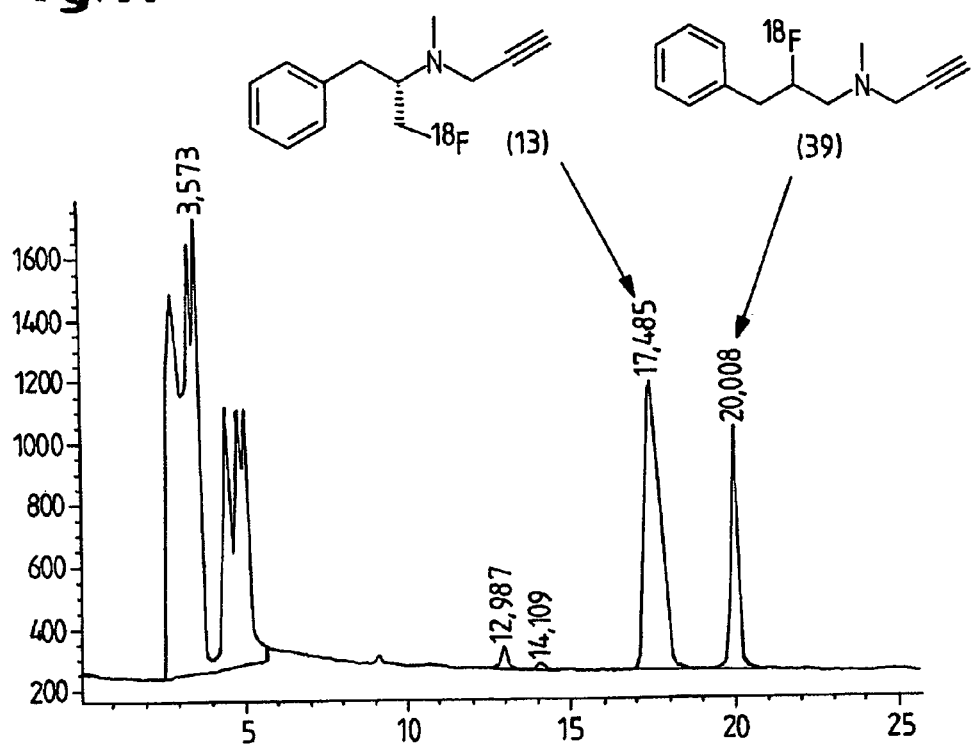
FIG. 11: radio-chromatogram of crude product (starting from 42 and 43 towards compound 13 and 39) on ACE 5-C18-HL 250 mm×10 mm column, Advanced Chromatography Technologies; Cat. No.: ACE 321-2510; isocratic, 35% acetonitrile in 0.1% trifluoroacetic acid, flow: 4 ml/min; $t_R$=17.5 min.
Figure 12:
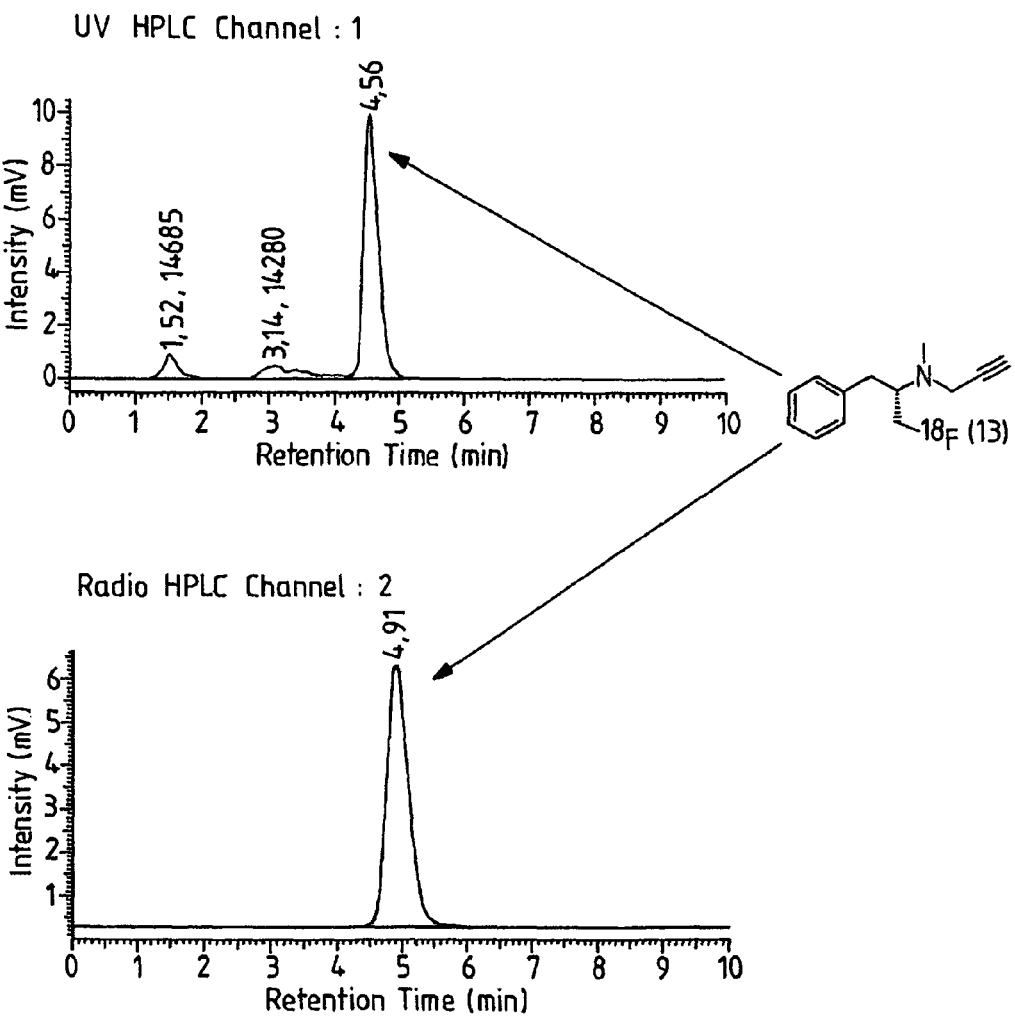
FIG. 12: Analytical chromatogram of compound 13 on reverse phase HPLC on a µ-Bondapak C-18 column (300×3.9 mm, 10 µm; waters instruments) and MeCN—H$_3$PO$_4$ (0.01 M) (15:85 v/v) was used as the eluting solvent at a flow rate of 2 mL/min. The eluate was monitored by a UV absorbance detector (λ=214 nm) in series with a radioactivity detector (β-flow; Beckman, Fullerton, Calif.).
Figure 13:
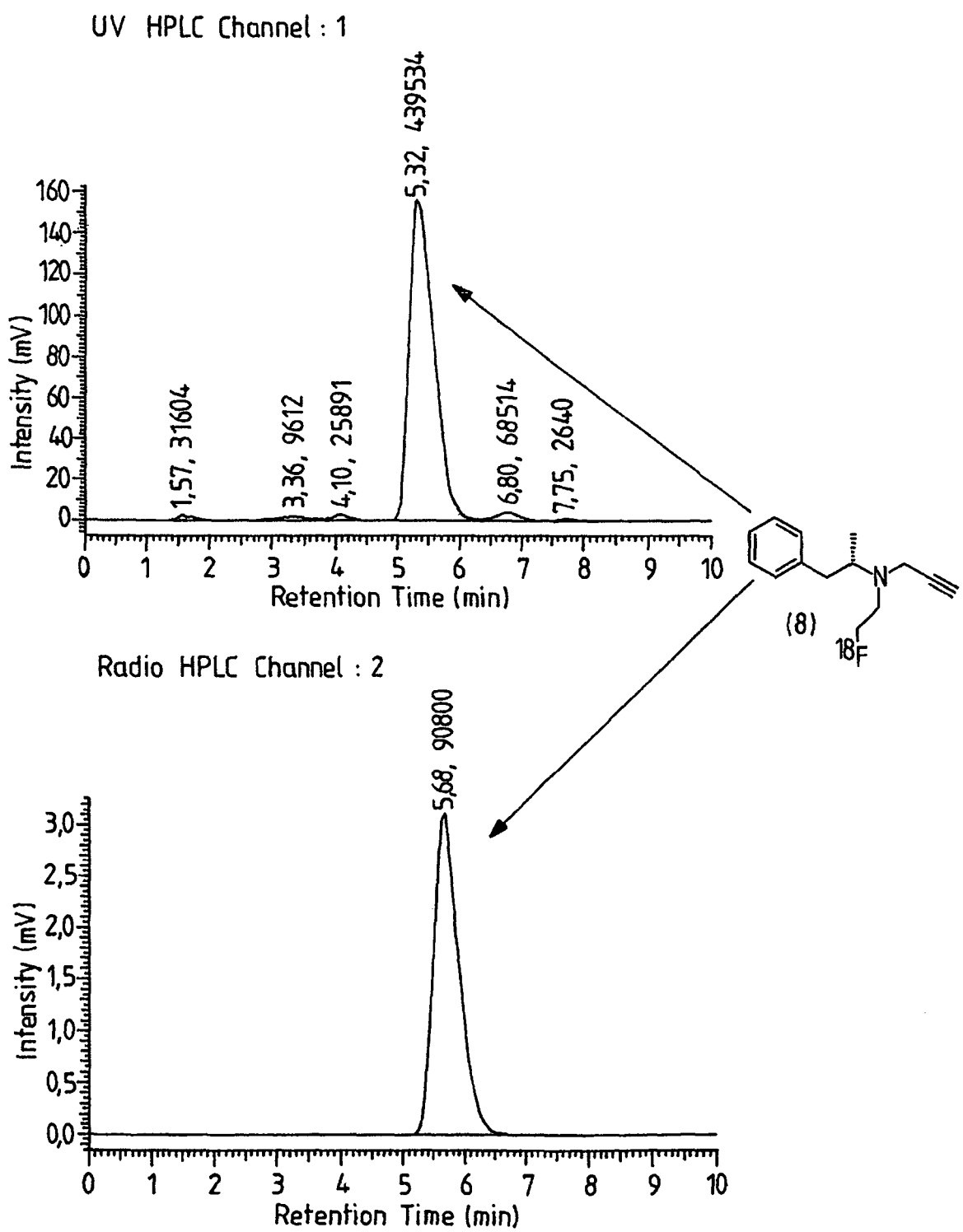
FIG. 13: Analytical chromatogram of compound 8 on reverse phase HPLC on a P-Bondapak C-18 column (300×3.9 mm, 10 µm; waters instruments) and MeCN—H$_3$PO$_4$ (0.01 M) (15:85 v/v) was used as the eluting solvent at a flow rate of 2 mL/min. The eluate was monitored by a UV absorbance detector (λ=214 nm) in series with a radioactivity detector (β-flow; Beckman, Fullerton, Calif.).

The stability and radiochemical yield was analyzed with HPLC and TLC on silica gel. TLC plate was scanned with an AR-2000 Imaging Scanner and analyzed with Winscan 2.2 software. The incorporation yield of the fluorination reaction varied from 40% to 70%. The radiochemical purity was more than 99% for all three radioligands. Radioligands were found to be stable in PBS buffer solution for the duration of experiments. Radiochemical purity was >99% at 3 h after formulation with PBS which was determined by HPLC and TLC. Alternatively, compound 13 and 39 were also separated via an preparative HPLC column and method (comp. FIG. 11): ACE 5-C18-HL 250 mm×10 mm, Advanced Chromatography Technologies; Cat. No.: ACE 321-2510; isocratic, 35% acetonitrile in 0.1% trifluoroacetic acid, flow: 4 ml/min; $t_R$=17.5 min. The collected HPLC fraction was diluted with 40 ml water and immobilized on a Sep-Pak Plus C18 cartridge (Waters), which was washed with 5 ml water and eluted with 1 ml ethanol to deliver compound 13 in a radiochemical purity >99%. The desired product 13 was characterized by co-injection with the non-radioactive F-19 fluoro standard 12 on the analytical HPLC.

D: Alkylation of NH-carbamate with [F-18] Labeled Prosthetic Group

To a suspension of 1 ml dry tetrahydrofuran (THF) and 7.7 mmol sodium hydride—which has been washed with hexane—7 mmol starting material in 1 ml THF is added dropwisely. The reaction mixture is stirred for 20 min. The prepared [F-18]-fluoro-alkyl bromide (100-500 GBq; known from literature) in tetrahydrofuran is dropped into the suspension. The reaction is heated to 50° C. for 20 min. The vigorously reaction mixture is cooled to room temperature. The crude reaction mixture is analyzed using analytical HPLC. The desired F-18 labeled product is confirmed by co-injection with the non-radioactive F-19 fluoro-standard on the analytical HPLC.

E: Fluorination with [F-18] Fluoride Using Tetrabutylammonium Hydroxide And Subsequent Deprotection
compare also: J. Med. Chem. 2007, 50, 1028-1040.

$[^{18}F]$fluoride was transferred to a Vacutainer that had previously been treated with tetrabutylammonium hydroxide (2 micro liter). The $[^{18}O]H_2O$ was removed by azeotropic distillation with acetonitrile (3_times 0.75 mL), $N_2$, and heat (compare Nucl. Med. Biol. 2003, 30, 397-404). Precursor (3.0 micro mol) was added to the vessel and dissolved in DMSO (400 micro liter). The resulting mixture was heated by microwave irradiation (3 times for 20 sec). The crude mixture was passed over a silica pipet column (50 mg) with $CH_3CN$ (3 mL), and the volatile organics were then removed using reduced pressure. The vial containing a crude mixture of $[^{18}F]$product was dissolved in $CH_3CN$ (500 micro L) and was treated with 4N sulfuric acid (0.5 ml). The resulting mixture was heated by microwave irradiation (3 times for 20 sec). The desired product was separated via an preparative HPLC column and method: ACE 5-C18-HL 250 mm×10 mm, Advanced Chromatography Technologies; Cat. No.: ACE 321-2510; isocratic, 35% acetonitrile in 0.1% trifluoroacetic acid, flow: 4 ml/min). The collected HPLC fraction was diluted with 40 ml water and immobilized on a Sep-Pak Plus C18 cartridge (Waters), which was washed with 5 ml water and eluted with 1 ml ethanol to deliver compound 13 in a radiochemical purity >99%. The desired product 13 was characterized by co-injection with the non-radioactive F-19 fluoro standard 12 on the analytical HPLC.

F: Alkylation of NH-carbamate

To a stirred suspension of 20 ml dry DMF and 11 mmol sodium hydride—which has been washed with hexane—10 mmol starting material in 5 ml DMF is added dropwisely at 0° C. The reaction mixture is stirred for 20 min. 15 mmol alkylation agent diluted in 5 ml tetrahydrofuran is added dropwisely to the stirred suspension. The reaction mixture is stirred for 16-10 hours. The reaction mixture is poured onto a vigerously stirred mixture of ice-water and diethyl ether. The organic phase is separated. The aqueous phase is extracted three times with 30 ml diethyl ether. The combined organic phases are washed with brine and dried with magnesium sulfate. The solvent is evaporated and the residue is purified by column chromatography with ethyl acetate-hexane gradient.

G: Alkylation of NH-amine with [F-18] Labeled Prosthetic Group

To a solution 2 mg secondary amine (starting material) and 3 mg potassium carbonate in 0.7 ml dimethyl formamide was added [F-18]fluoro-alkylating agent (ca. 200-1000 MBq) in dimethyl formamide prepared from literature protocol. The reaction mixture is heated to 110° C. for 20 min. The reaction mixture is cooled to room temperature. The desired F-18 labeled product is confirmed by co-injection with the non-radioactive F-19 fluoro-standard on the analytical HPLC. The crude product (ca. 50-400 MBq) is purified by preparative HPLC column. The desired product is obtained (ca. 15-200 MBq) as reconfirmed by co-injection with the non-radioactive F-19 fluoro standard on the analytical HPLC.

H: Alkylation of NH-amine (Secondary Amine) or Phenols

To a stirred solution of 2 mmol starting material and 0.415 g (3 mmol) potassium carbonate in 6 ml dimethyl formamide was added 2.5 mmol alkylating agent. The reaction mixture was heated by microwave to −110° C. for 15 min. The solvent of the reaction mixture is evaporated. Water (8 ml) and diethylether or dichloromethane/isopropanol mixture (1:10-8 ml)

are added. The organic phase is separated. The aqueous phase is extracted three times with 30 ml diethyl ether. The combined organic phases are washed with water (twice ca. 5 ml), brine and dried with magnesium sulfate. The solvent is evaporated and the residue is purified by column chromatography with ethyl acetate-hexane gradient.

I: Conversion of Alcohol to Corresponding O-sulfonate (Version 1)

To a solution of 0.5 mmol starting material and 0.103 g (0.8 mmol) diisopropyl ethyl amine in 1.5 ml dichloromethane was added (0.6 mmol) mesyl chloride or mesyl anhydride in 0.1 ml dichloromethane dropwise at −10° C. The stirred reaction mixture was warmed over a period of 4.5 h to room temperature and diluted with dichloromethane. The organic phase was washed with saturated sodium hydrogen carbonate solution, water and brine. The organic phase was dried with magnesium sulfate. The crude product was purified by silica column chromatography (ethyl acetate-hexane gradient).

K: Conversion of Alcohol to Corresponding O-sulfonate (Version 2)

To a solution of 3 mmol starting material in 5 ml dichloromethane and 5 ml pyridine was added (3.3 mmol) aryl sulfonyl chloride in 3 ml dichloromethane dropwisely at −10° C. The stirred reaction mixture was warmed over a period of 4.5 h to room temperature and diluted with dichloromethane. The organic phase was washed with 0.5N sulfuric acid (three times), saturated sodium hydrogen carbonate solution, water and brine. The organic phase was dried with magnesium sulfate. The crude product was purified by silica column chromatography (ethyl acetate-hexane gradient).

M: Deprotection of Acid Labile Protecting Group (Version 1)

A solution of 5 mmol starting material in wet trifluoro acetic acid-dichloromethane mixture (1:1) was stirred for 4-7 hours. The reaction mixture is evaporated. The residue is solved in dichloromethane and the solution is evaporated again. The last step is repeated three times. The residue is purified by column chromatography (dichloromethane—pentane gradient, amino phase).

N: Deprotection of Acid Labile Protecting Group (Version 2) (According to J. Am. Chem. Soc., 6644, 92, (1970))

To a stirred solution of 0.5 mmol starting material in 1 ml ethanol is added 1 ml of 3N aqueous hydrogen chloride at 0° C. The solution is stirred for 16 h at room temperature. The reaction is treated with NaOH aq. (4N) until pH=9.5. Ethanol is evaporated. Water (10 ml) and dichloromethan-isopropanol (10 ml; 10:1) are added. The organic phase is separated. The aqueous phase is extracted three times with 10 ml dichloromethan-isopropanol (10:1). The combined organic phases are washed with brine and dried with magnesium sulfate. The solvent is evaporated and the residue is purified by column chromatography with ether-pentane gradient or by preparative HPLC methods.

P: Reduction of Acids to Alcohols via Mixed Anhydride

According to Journal of Medicinal Chemistry, 2006, Vol. 49, No. 15, p. 4544, compound 94. A stirred solution of 11 mmol carboxylic acid (startmaterial) and triethylamine (1.9 mL, 14 mmol) in THF (300 mL) was added ethyl chloroformate (13 mL, 14 mmol) at −5° C. The mixture was stirred for 20 min, and then sodium borohydride (1.72 g, 44 mmol) and methanol (32 mL) were added consecutively. The mixture was stirred for 30 min at −5° C., and then saturated NH$_4$Cl was added to quench the reaction. The mixture was extracted with Et2O (ca. 50 ml), and the combined organic layers were washed with brine, dried over Na2SO4, and concentrated. Flash chromatography (hexane/AcOEt 1/1) of the residue gave the desired product.

Q: Reduction of Oxazolidinones Towards N-Methyl Aminoalcohols

To a stirred solution of 5 mmol starting material (oxazolidinone) in 10 ml THF were added 10 mmol lithium aluminium hydride at 0° C. The reaction suspension was stirred for 4 h at room temperature. The vigorously stirred reaction mixture was treated dropwisely with 10 ml of a 1 m NaOH (aq) solution. The reaction mixture was stirred for 30 min and filtered. The filtrate was concentrated and the residue was purified by silica chromatography (ethyl acetate/hexane gradients).

S: Reduction of Esters Towards Alcohols

To a solution of 15 mmol (555 mg) NaBH4 in 15 ml water/THF (1:1) is added 10 mmol ester (starting material), dissolved in 20 ml THF, drop by drop. The reaction micture is stirred for 4 hours. The reaction mixture is poured into stirred mixture of ice-cold water and diethyl ether (200 ml, 1:1). The organic phase is separated. The aqueous phase is extracted three times with 10 ml diethyl ether. The combined organic phases are washed with brine and dried with magnesium sulfate. The solvent is evaporated and the residue is purified by column chromatography with ethyl acetate-hexane gradient.

T: Conversion of Alcohol to Corresponding Triflate

According to Chem. Eur. J. (2007), 13, 115-134:

Pyridine (0.25 ml, 3.13 mmol) and Tf$_2$O (0.32 ml, 1.88 mmol) were successively added to a solution of starting material (1.34 mmol) in CH$_2$Cl$_2$ (50 mL) at −20° C. and the resulting mixture was stirred for 1 h at that temperature. The pale pink solution was transferred into a separation funnel containing aq. KHSO$_4$ (30 mL, 10%) and ice. The aqueous layer was extracted with CH$_2$Cl$_2$, the combined organic phases were dried over Na$_2$SO$_4$, and the solvent was carefully evaporated while keeping the temperature at 0° C. The desired product is filtered through a silica bed using ethyl acetate hexane solvent mixture.

U: Reduction of Mesylate Towards Alkane

Similar to Org. Lett.; 2004; 6(24) pp 4439-4442:

To a solution of starting material (0.5 mmol) in anhydrous ether (20 mL) was added lithium aluminium hydride (65 mg) at 0° C., stirred for 24 h at the same temperature. After addition of 0.263 ml 2M NaOH solution at −10° C. the reaction mixture was stirred for 30 min at room temperature and filtered. The filtrate was concentrated and the residue was used without further purification.

V: Fluorination of Secondary Alcohol (DBU/NfF):

According to Tetrahedron Letters, Vol. 36, No. 15, pp. 2611-2614, 1995:

To a cooled solution of secondary alcohol (2.5 mmol) and DBU (1.12 mL, 7.5 mmol) in toluene (20 mmol), C$_4$F$_9$SO$_2$F (nona-fluoro-butyl-sulfonyl-fluorid) (1.13 g, 3.75 mmol) was added with stirring at 0° C. After 1 h at 0° C., the reaction mixture was evaporated in vacuo and the residue chromatographed in hexane/ethylacetate gradient on a silica column.

For the following examples, NMR spectra were recorded on 400 MHz, 600 MHz ($^1$H), 100 MHz and 151 MHz ($^{13}$C) NMR instruments. $^1$H NMR spectra were referenced internally on CDCl$_3$ ($\delta^1$H 7.26) and $^{13}$C NMR spectra were referenced internally on CDCl$_3$ ($\delta^{13}$C 77.20). Liquid chromatographic analysis (LC) was performed with a Merck-Hitachi gradient pump and a Merck-Hitachi, L-4000 variable wavelength UV-detector. A p-Bondapak C-18 column (300×7.8 mm, 10 μm; waters instruments) was used with a flow of 2 ml/min. LC-MS was performed using a Waters Quattra-Tof Premier micro mass coupled with Waters Acquity HPLC instrument. The ionization mode used was electro spray positive ionization (ESI+). Analytical TLC was carried out on 0.25 mm silica gel plates.

All solvents and chemicals were obtained from commercial sources and used without further purification.

Example 1 a) Synthesis of ((S)-1-Hydroxymethyl-2-phenyl-ethyl)-methyl-carbamic Acid Tert-butyl Ester (1a)

(S)-2-(tert-Butoxycarbonyl-methyl-amino)-3-phenyl-propionic acid (Fluka) is reduced according to general method P to obtain compound 1a in 80% yield (8.8 mmol, 2.34 g).
MS-ESI: 266 ($M^+$+1, 100).
Elementary analysis:

| Calculated: | C 67.90% H 8.74% N 5.28% |
|---|---|
| Determined: | C 67.87% H 8.72% N 5.27% | b) Synthesis of (S)-2-Methylamino-3-phenyl-propan-1-ol (1b)

Compound 1a is deproteted according to general procedure M to obtain compound 1b in 77% yield (630 mg, 3.8 mmol).
MS-ESI: 166 ($M^+$+1, 100).
Elementary analysis:

| Calculated: | C 72.69% H 9.15% N 8.48% |
|---|---|
| Determined: | C 72.66% H 9.13% N 8.47% | c) Synthesis of (S)-2-(Methyl-prop-2-ynyl-amino)-3-phenyl-propan-1-ol (1c)

Compound 1c is synthesized according to general procedure H from starting material 1b using 2.5 mmol of propargyl bromide (298 mg). The desired compound is obtained in 60% yield (243 mg, 1.2 mmol).
MS-ESI: 204 ($M^+$+1, 100).
Elementary analysis:

| Calculated: | C 76.81% H 8.43% N 6.89% |
|---|---|
| Determined: | C 76.77% H 8.42% N 6.88% | d) Synthesis of Methanesulfonic Acid (S)-2-(methyl-prop-2-ynyl-amino)-3-phenyl-propyl Ester (1d)

Compound 1d is synthesized by general procedure I from starting material 1c in 91% yield (126 mg, 0.45 mmol).
MS-ESI: 282 ($M^+$+1, 100).
Elementary analysis:

| Calculated: | C 59.76% H 6.81% N 4.98% |
|---|---|
| Determined: | C 59.78% H 6.82% N 4.99% | e) Synthesis of ((S)-1-Fluoromethyl-2-phenyl-ethyl)-methyl-prop-2-ynyl-amine (1e)

Compound 1e is synthesized by general procedure A from starting material 1d in 48% yield (24 mg, 0.12 mmol).
MS-ESI: 206 ($M^+$+1, 100).
Elementary analysis:

| Calculated: | C 76.07% H 7.86% N 6.82% |
|---|---|
| Determined: | C 76.04% H 7.85% N 6.83% | f) Synthesis of ((S)-[$^{18}$F] 1-Fluoromethyl-2-phenyl-ethyl)-methyl-prop-2-ynyl-amine (1e)

Compound 1f is prepared from compound 1e by general procedure B. The desired product 1e is obtained with 254 MBq starting from 1.12 GBq F-18 fluoride (decay corrected).

g) Synthesis of (2S)-2-(methylamino)-3-phenylpropan-1-ol (1b)

To a solution of N-methyl-L-phenylalanine (Sigma, 10 g, 55.8 mmol) in dry THF (600 mL) was added 3.18 g (83.7 mmol) lithium aluminium hydride at −5° C. The reaction mixture was stirred over night and cooled to −5° C. Additional 2.12 g (55.8 mmol) lithium alanate were added. The reaction mixture was refluxed overnight and cooled then to −5° C. To this mixture was added 21.5 ml NaOH solution (2N) drop by drop. and stirred at room temperature for additional 30 min. The mixture was filtered and the filtercake was washed with diethyl ether (50 mL). The filtrate was dried over $MgSO_4$ and solvent was removed under reduced pressure to obtain the product 1b as light yellow solid.
MS-ESI: 204 ($M^+$+1, 100).
Elementary analysis:

| Calculated: | C 72.69% H 9.15% N 8.48% |
|---|---|
| Determined: | C 72.65% H 9.13% N 8.45% | h) Synthesis of a Mixture of N-[(2S)-1-chloro-3-phenylpropan-2-yl]-N-methylprop-2-yn-1-amine (1 h) and N-(2-chloro-3-phenylpropyl)-N-methylprop-2-yn-1-amine (1i)

To a stirred solution of 1c (100 mg, 0.49 mmol) and triethyl amine (1.0 mmol), in THF (2 ml) was stirred at room temperature for 30 min. To the stirred mixture mesylchloride (0.60 mmol) was added drop wise at −7° C. and the reaction mixture was stirred at room temperature for additional 30 min. Saturated $Na_2CO_3$ solution (1 mL) was added and stirred for 30 more min. The organic layer was partitioned between CH2Cl2 (15 ml) and water (10 ml). The organic phase was separated and washed with saturated $NaHCO_3$ (10 ml) and brine (10 ml) and dried over $MgSO_4$ and filtered. The solvent was removed under reduced pressure to obtain the crude product as light yellow oil. The crude product was purified by silica-gel column chromatography (hexane/ether 3:1) and analyzed by NMR, HPLC and LC-MS. The final product was obtained as mixture of 1h and 1i.

1h:
$^1$H NMR (600 MHz, CHLOROFORM-d) δ ppm 2.21 (t, J=2.38 Hz, 1 H) 2.38 (s, 3 H) 2.73 (d, J=6.97 Hz, 2 H) 2.95 (dd, J=14.31, 8.07 Hz, 1 H) 3.23 (dd, J=14.31, 4.77 Hz, 1 H) 3.43 (dd, J=10.45, 2.38 Hz, 2 H) 4.10-4.18 (m, 1 H) 7.28-7.35 (m, 5 H)
$^{13}$C NMR (151 MHz, CHLOROFORM-d) δ ppm 34.77 (1 C) 38.29 (1 C) 43.58 (1 C) 44.24 (s, 1C) 64.28 (1 C) 73.37 (1 C) 79.24 (1 C) 126.38 (1 C) 128.54 (1 C) 129.24 (1 C) 138.86 (1 C)

1i

¹H NMR (600 MHz, CHLOROFORM-d) δ ppm 2.21 (t, J=2.38 Hz, 1H) 2.38 (s, 3 H) 2.73 (d, J=6.97 Hz, 2 H) 2.95 (dd, J=14.31, 8.07 Hz, 1 H) 3.23 (dd, J=14.31, 4.77 Hz, 1 H) 3.43 (dd, J=10.45, 2.38 Hz, 2 H) 4.10-4.18 (m, 1 H) 7.28-7.35 (m, 5 H)

¹³C NMR (151 MHz, CHLOROFORM-d) δ ppm 42.08 (1 C) 42.33 (1 C) 45.94 (1 C) 60.43 (1 C) 61.52 (1 C) 73.49 (1 C) 77.98 (1 C) 126.76 (1 C) 128.33 (1 C) 129.50 (1 C) 138.94 (1 C)

i) Synthesis of N-[(2S)-1-fluoro-3-phenylpropan-2-yl]-N-methylprop-2-yn-1-amine (1e) and N-(2-fluoro-3-phenylpropyl)-N-methylprop-2-yn-1-amine (1k)

Figure 15:
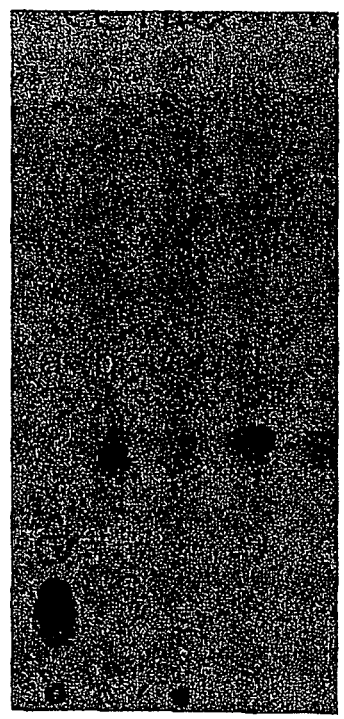
FIG. 15: TLC analysis (silica gel, molybdato phosphoric acid diving bath; ethylacetate hexane: 1:2) of fluorination reaction starting from compound 10 towards compound 12 and 41. (a): starting material (10) (with impurity ("circled")) of the mentioned reaction. (b): column fraction containing mainly compound 41. (c): column fraction containing compound 12 and 41. (d): column fraction containing mainly compound 12. (e): column fraction containing compound 12 and 41.

To the stirred solution of 1c (300 mg, 1.48 mmol) in dichloromethane (5 mL) DAST (2.0 mmol) was added drop wise at −5° C. and the reaction mixture was stirred for additional 20 min at the same temperature. Saturated sodium carbonate (4.0 mL) was added to quench the untreated DAST. The organic layer was partitioned between $CH_2Cl_2$ (25 ml) and water (15 ml). The organic phase was separated and washed with brine (10 ml) and dried over $MgSO_4$ and filtered. The solvent was removed under reduced pressure to obtain the crude product as light yellow oil. The crude product was purified by silica-gel column chromatography (hexane/ether 3:1) to obtain 1e and 1k as isolated products (compare TLC: FIG. 15).

1e:
¹H NMR (600 MHz, CHLOROFORM-d) δ ppm 2.27 (t, 1 H) 2.52 (s, 3H) 2.74 (dd, J=13.39, 10.09 Hz, 1 H) 2.97-3.03 (m, 1 H) 3.03-3.14 (m, 1 H) 3.53 (t, J=2.75 Hz, 2 H) 4.38 (ddd, J=47.32, 10.09, 4.95 Hz, 1 H) 4.51 (ddd, J=48.05, 10.27, 2.57 Hz, 1 H).

¹³C NMR (151 MHz, CHLOROFORM-d) δ ppm 32.91 (d, J=6.13 Hz, 1 C) 38.20 (d, J=1.67 Hz, 1 C) 43.94 (d, J=2.23 Hz, 1 C) 63.83 (d, J=17.54 Hz, 1 C) 72.83 (1 C) 80.15 (s, 1 C) 82.27 (d, J=172.08 Hz, 1 C) 126.31 (1 C) 128.51 (1 C) 129.24 (1 C) 139.01 (1 C).

1k:
¹H NMR (600 MHz, CHLOROFORM-d) δ ppm 2.21 (t, J=2.38 Hz, 1 H) 2.37 (s, 3 H) 2.59-2.72 (m, 2 H) 2.90-3.01 (m, 2 H) 3.41 (dd, J=4.95, 2.38 Hz, 2 H) 4.75-4.89 (m, 1 H) 7.20-7.32 (m, 5H).

¹³C NMR (151 MHz, CHLOROFORM-d) δ ppm 39.66 (d, J=21.44 Hz, 1 C) 42.40 (d, J=1.39 Hz, 1 C) 46.30 (d, J=1.67 Hz, 1 C) 58.53 (d, J=20.88 Hz, 1 C) 73.37 (s, 1 C) 78.22 (s, 1 C) 92.84 (d, J=173.19 Hz, 1 C) 126.63 (1 C) 128.45 (1 C) 129.37 (1 C) 136.85 (d, J=4.46 Hz, 1 C).

j) Synthesis of N-[(2S)-1-($^{18}$F)fluoro-3-phenylpropan-2-yl]-N-methylprop-2-yn-1-amine (1f) and N-[2-($^{18}$F)fluoro-3-phenylpropyl]-N-methylprop-2-yn-1-amine (1m)

The crude products 1f and 1m were obtained according to genaral procedure C. The products 1f and 1m were separated according to general procedure C and investigated separately after HPLC separation (compare HPLC chromatograms FIG. 11 and FIG. 12).

Example 2 a) Synthesis of (4R,5S)-4-Methyl-5-phenyl-3-prop-2-ynyl-oxazolidin-2-one (2a)

Compound 2a is synthesized from (4R,5S)-(+)-4-Methyl-5-phenyl-2-oxazolidinone (Aldrich) according to general procedure F using 15 mmol (1.79 g) propargyl bromide (Aldrich).

Compound 2a is obtained in 76% yield (7.6 mmol, 1.61 g).
MS-ESI: 216 (M⁺+1, 100).
Elementary analysis:

| Calculated: | C 72.54% H 6.09% N 6.51% |
| Determined: | C 72.52% H 6.11% N 6.52% | b) Synthesis of (1S,2R)-2-(Methyl-prop-2-ynyl-amino)-1-phenyl-propan-1-ol (2b)

Compound 2b is synthesized by general procedure Q from starting material 2a in 89% yield (0.91 g, 4.5 mmol).
MS-ESI: 204 (M⁺+1, 100).
Elementary analysis:

| Calculated: | C 76.81% H 8.43% N 6.89% |
| Determined: | C 76.82% H 8.41% N 6.88% | c) Synthesis of methanesulfonic acid (1S,2R)-2-(methyl-prop-2-ynyl-amino)-1-phenyl-propyl ester (2c)

Compound 2c is synthesized by general procedure T from starting material 2b in 78% yield (352 mg, 1.05 mmol).
MS-ESI: 336 (M⁺+1, 100).
Elementary analysis:

| Calculated: | C 50.14% H 4.81% N 4.18% |
| Determined: | C 50.17% H 4.82% N 4.16% | d) Synthesis of ((1R,2R)-[$^{18}$F]-2-Fluoro-1-methyl-2-phenyl-ethyl)-methyl-prop-2-ynyl-amine (2d)

Compound 2d is prepared from compound 2c by general procedure B. The desired product 2d is obtained with 198 MBq starting from 1.09 GBq F-18 fluoride (decay corrected).

e) Synthesis of ((1R,2R)-2-Fluoro-1-methyl-2-phenyl-ethyl)-methyl-prop-2-ynyl-amine (2e)

Compound 2e is synthesized by general procedure V from starting material 2b in 58% yield (297 mg, 1.45 mmol).
MS-ESI: 206 (M⁺+1, 100).
Elementary analysis:

| Calculated: | C 76.07% H 7.86% N 6.82% |
| Determined: | C 76.04% H 7.84% N 6.83% | f) Synthesis of N-[(1R,2R)-1-chloro-1-phenylpropan-2-yl]-N-methylprop-2-yn-1-amine (2f)

To a stirred solution of 2b (120 mg, 0.54 mmol) and triethyl amine (1.0 mmol), in THF (2 ml) was stirred at room temperature for 30 min. To the stirred mixture mesylchloride (0.60 mmol) was added drop wise at −7° C. and the reaction mixture was stirred at room temperature for additional 30 min. Saturated $Na_2CO_3$ solution (1 mL) was added and stirred for 30 more min. The organic layer was partitioned between $CH_2Cl_2$ (15 ml) and water (10 ml). The organic phase was separated and washed with saturated $NaHCO_3$ (10 ml) and brine (10 ml) and dried over MgSO$_4$ and filtered. The solvent was removed under reduced pressure to obtain the crude product as light yellow oil. The crude product was purified by silica-gel column chromatography (hexane/ether 3:1).
MS-ESI: 221 (M+35Cl+1,82).
Elementary analysis:

| Calculated: | C 70.42% H 7.27% Cl 15.99% N 6.32% |
| Determined: | C 70.38% H 7.25% Cl 15.97% N 6.30% | g) Synthesis of N-[(1S,2R)-1-($^{18}$F)fluoro-1-phenyl-propan-2-yl]-N-methylprop-2-yn-1-amine (2 g)

The desired product (2g) was obtained from 2f according to the general procedure C.

Example 3 a) Synthesis of 4-Furan-2-ylmethyl-3-prop-2-ynyl-oxazolidin-2-one (3a)

Compound 3a is synthesized according to general procedure F in 4 mmol scale from starting material 4-furan-2-ylmethyl-oxazolidin-2-one (J. Am. Chem. Soc.; 125; 42; 2003; 12694-12695). The desired compound 3a is obtained in 60% yield (2.4 mmol) using 6 mmol propagyl bromide as alkylating agent.
MS-ESI: 205 (M$^+$+1, 100).
Elementary analysis:

| Calculated: | C 64.38% H 5.40% N 6.83% |
| Determined: | C 64.41% H 5.41% N 6.82% | b) Synthesis of 3-Furan-2-yl-2-(methyl-prop-2-ynyl-amino)-propan-1-ol (3b)

Compound 3b is synthesized by general procedure Q (half scale) from starting material 3a in 70% yield (338 mg, 1.75 mmol).
MS-ESI: 194 (M$^+$+1, 100).
Elementary analysis:

| Calculated: | C 68.37% H 7.82% N 7.25% |
| Determined: | C 68.37% H 7.81% N 7.26% | c) Methanesulfonic acid 3-furan-2-yl-2-(methyl-prop-2-ynyl-amino)-propyl ester (3c)

Compound 3c is synthesized by general procedure I from starting material 3b in 88% yield (120 mg, 0.44 mmol).
MS-ESI: 272 (M$^+$+1, 100).
Elementary analysis:

| Calculated: | C 53.12% H 6.32% N 5.16% |
| Determined: | C 53.15% H 6.34% N 5.18% | d) Synthesis of 1-Fluoromethyl-2-furan-2-yl-ethyl)-methyl-prop-2-ynyl-amine (3d)

Compound 3d is synthesized by general procedure A from starting material 3c in 61% yield (29.9 mg, 0.153 mmol).

MS-ESI: 196 (M$^+$+1, 100).
Elementary analysis:

| Calculated: | C 67.67% H 7.23% N 7.17% |
| Determined: | C 67.67% H 7.23% N 7.18% | e) Synthesis of (1-Fluoromethyl-2-furan-2-yl-ethyl)-methyl-prop-2-ynyl-amine (3e)

Compound 3e is synthesized by general procedure A from starting material 3c with F-18 fluoride 0.96 GBq. The desired compound is obtained (124 MBq).

Example 4 a) Synthesis of (S)-4-Benzyl-3-prop-2-ynyl-oxazolidin-2-one (4a)

Compound 4a is synthesized by general procedure F from starting material (S)-4-Benzyl-oxazolidin-2-one (Aldrich) in 72% yield (1.58 g, 7.2 mmol).
MS-ESI: 216 (M$^+$+1, 100).
Elementary analysis:

| Calculated: | C 72.54% H 6.09% N 6.51% |
| Determined: | C 72.51% H 6.08% N 6.53% | b) (S)-2-(Methyl-prop-2-ynyl-amino)-3-phenyl-propan-1-ol (4b)

Compound 4b is synthesized by general procedure Q from 4a in 68% yield (690 mg, 3.4 mmol).
MS-ESI: 204 (M$^+$+1, 100).
Elementary analysis:

| Calculated: | C 76.81% H 8.43% N 6.89% |
| Determined: | C 76.78% H 8.41% N 6.90% | c) 4-Bromo-benzenesulfonic acid (S)-2-(methyl-prop-2-ynyl-amino)-3-phenyl-propyl ester (4c)

Compound 4c is synthesized by general procedure K from 4b p-bromo-benzene sulfonyl chloride in 47% yield (1.58 g, 1.41 mmol).
MS-ESI: 424 (M$^{+Br\text{-}isotope}$ 80+1, 76).

| Elementary analysis: | C 54.03% H 4.77% N 3.32% |
| Determined: | C 54.03% H 4.77% N 3.32% |

Example 5 a) Synthesis of (S)-4-[4-(2-Methoxymethoxy-ethoxy)-benzyl]-oxazolidin-2-one (5a)

Compound 5a is synthesized by general procedure H from (S)-(−)-4-(4-hydroxybenzyl)-2-oxazolidinone (Tetrahedron; EN; 57; 39; 2001; 8313-8322) and 2-bromo-ethyl-methoxy-methyl-ether (Aldrich) at 10-fold scale in 77% yield (15.4 mmol, 4.33 g).

MS-ESI: 282 (M$^+$+1, 100).
Elementary analysis:

| Calculated: | C 59.78% H 6.81% N 4.98% |
| Determined: | C 59.81% H 6.83% N 4.97% | b) Synthesis of (S)-4-[4-(2-Methoxymethoxy-ethoxy)-benzyl]-3-prop-2-ynyl-oxazolidin-2-one (5b)

Compound 5b is synthesized by general procedure F from compound 5a in 65% yield (6.5 mmol, 2.07 g).
MS-ESI: 320 (M$^+$+1, 100).
Elementary analysis:

| Calculated: | C 63.94% H 6.63% N 4.39% |
| Determined: | C 63.92% H 6.64% N 4.40% | c) Synthesis of (S)-3-[4-(2-Methoxymethoxy-ethoxy)-phenyl]-2-(methyl-prop-2-ynyl-amino)-propan-1-ol (5c)

Compound 5c is synthesized by general procedure Q from compound 5b in 74% yield (3.7 mmol, 1.14 g).
MS-ESI: 308 (M$^+$+1, 100).
Elementary analysis:

| Calculated: | C 66.43% H 8.20% N 4.56% |
| Determined: | C 66.46% H 8.21% N 4.55% | d) Synthesis of {(R)-2-[4-(2-Methoxymethoxy-ethoxy)-phenyl]-1-methyl-ethyl}-methyl-prop-2-ynyl-amine (5d)

Compound 5d is synthesized by general sequential procedure I (at 5-fold scale) and U from compound 5c in 81% yield over two steps (2.02 mmol, 589 mg).
MS-ESI: 292 (M$^+$+1, 100).
Elementary analysis:

| Calculated: | C 70.07% H 8.65% N 4.81% |
| Determined: | C 70.11% H 8.63% N 4.82% | e) Synthesis of 2-{4-[(R)-2-(Methyl-prop-2-ynyl-amino)-propyl]-phenoxy}-ethanol (5e)

Compound 5e is synthesized by general sequential procedure N (at 4-fold scale) from compound 5d in 88% yield (1.76 mmol, 436 mg).
MS-ESI: 248 (M$^+$+1, 100).
Elementary analysis:

| Calculated: | C 72.84% H 8.56% N 5.66% |
| Determined: | C 72.81% H 8.55% N 5.67% | f) Methanesulfonic acid 2-{4-[(R)-2-(methyl-prop-2-ynyl-amino)-propyl]-phenoxy}-ethyl ester (5f)

Compound 5f is synthesized by general sequential procedure I from compound 5e in 93% yield (0.47 mmol, 153 mg).
MS-ESI: 326 (M$^+$+1, 100).
Elementary analysis:

| Calculated: | C 59.05% H 7.12% N 4.30% |
| Determined: | C 59.07% H 7.11% N 4.30% | g) Synthesis of {(R)-2-[4-(2-Fluoro-ethoxy)-phenyl]-1-methyl-ethyl}-methyl-prop-2-ynyl-amine (5g)

Compound 5g is synthesized by general procedure A from compound 5f in 61% yield (0.153 mmol, 38 mg).
MS-ESI: 250 (M$^+$+1, 100).
Elementary analysis:

| Calculated: | C 72.26% H 8.09% N 5.62% |
| Determined: | C 72.22% H 8.07% N 5.60% | h) Synthesis of [F-18]{(R)-2-[4-(2-Fluoro-ethoxy)-phenyl]-1-methyl-ethyl}-methyl-prop-2-ynyl-amine (5h)

Compound 5h is synthesized by general procedure B from compound 5f (isolated 210 MBq from 1.41 GBq).

Example 6 a) Synthesis of ((R)-1-methyl-2-phenyl-ethyl)-prop-2-ynyl-amine (6a)

840 mg (4 mmol) ((R)-1-methyl-2-phenyl-ethyl)-prop-2-ynyl-ammonium hydrochloride (Sigma) is dissolved in 10 ml dichloromethane and 1M aqueous sodium carbonate. The organic phase is separated. The aqueous phase is extracted three times with 10 ml dichloromathane. The combined organic phases are washed with brine and dried with magnesium sulfate. The crude product 6a is used without further purification.

b) (2-Fluoro-ethyl)-((R)-1-methyl-2-phenyl-ethyl)-prop-2-ynyl-amine (6b)

Compound 6b is synthesized by general procedure H from compound 6a in 60% yield (1.2 mmol, 262 mg).
MS-ESI: 220 (M$^+$+1, 100).
Elementary analysis:

| Calculated: | C 76.68% H 8.27% N 6.39% |
| Determined: | C 76.66% H 8.26% N 6.38% | c) [F-18] (2-Fluoro-ethyl)-((R)-1-methyl-2-phenyl-ethyl)-prop-2-ynyl-amine (6c)

Compound 6c is synthesized by general procedure G from compound 6a and [F-18]-2-fluoro-ethyl-bromide (Bioorg.

Med. Chem.; 13; 20; 2005; 5779-5786). The desired product 6c is obtained with 178 MBq starting from 1.98 GBq F-18 fluoride (decay corrected).

d) Synthesis of 2-{[(2R)-1-phenylpropan-2-yl](prop-2-yn-1-yl)amino}ethanol (6d)

A mixture of desmethyldeprenyl (Sigma, 150 mg, 0.72 mmol) and NaOH (60 mg, 1.5 mmol), in MeCN (5 ml) was stirred at room temperature for 30 min. To the stirred mixture 1-bromo ethanol (1.0 mmol) was added and the reaction mixture was refluxed for overnight. The reaction mixture was allowed to cool to room temperature and solvent was evaporated under reduced pressure. The residue was partitioned between $CH_2Cl_2$ (20 ml) and water (10 ml). The organic phase was separated and washed with saturated $NaHCO_3$ (10 ml) and brine (10 ml). The organic layer was dried over $MgSO_4$ and filtered. The solvent was removed under reduced pressure to obtain the crude product as a light yellow liquid. The crude product was purified by silica-gel column chromatography (hexane/ether 8:2).
MS-ESI: 218 ($M^+$+1, 100).
Elementary analysis:

| Calculated: | C 77.38% H 8.81% N 6.45% O 7.36% |
|---|---|
| Determined: | C 77.35% H 8.79% N 6.43% O 7.35% | e) Synthesis of N-(2-chloroethyl)-N-[(2R)-1-phenyl-propan-2-yl]prop-2-yn-1-amine (6e)

A mixture of 2 (150 mg, 0.69 mmol) and triethyl amine (1.5 mmol), in THF (3 ml) was stirred at room temperature for 30 min. To the stirred mixture mesylchloride (1.4 mmol) was added drop wise at −7° C. and the reaction mixture was stirred at room temperature for additional 30 min. Saturated $Na_2CO_3$ solution (2 mL) was added and stirred for 30 more min. The organic layer was partitioned between CH2Cl2 (20 ml) and water (10 ml). The organic phase was separated and washed with saturated $NaHCO_3$ (10 ml) and brine (10 ml) and dried over $MgSO_4$ and filtered. The solvent was removed under reduced pressure to obtain the crude product as light yellow oil. The crude product was purified by silica-gel column chromatography (hexane/et her 3:1).
MS-ESI: 235 ($M^{+Cl35}$, 100).
Elementary analysis:

| Calculated: | C 71.33% H 7.70% N 5.94% |
|---|---|
| Determined: | C 71.30% H 7.68% N 5.92% | f) Synthesis of N-(2-fluoroethyl)-N-[(2R)-1-phenyl-propan-2-yl]prop-2-yn-1-amine (6b)

To a solution of N-[(2R)-1-phenylpropan-2-yl]prop-2-yn-1-aminium chloride (Sigma 100 mg, 0.578 mmol) in dry DMF (2 mL) was added sodium hydride (48.0 mg, 2 mmol). The reaction mixture was stirred at room temperature for 30 min, after which 1-bromo-2-fluoro ethane (0.85 mg, 0.603 mmol) was added. The reaction mixture was stirred over night, diluted with water (10 mL) and extracted with $CH_2Cl_2$ (3×15 mL). The organic phase was separated and washed with saturated $NaHCO_3$ (15 ml) and brine (15 ml) and dried over $MgSO_4$ and filtered. The solvent was removed under reduced pressure to obtain the crude product as light yellow oil. The crude product was purified by silica-gel column chromatography (hexane/ether 80:20) and analyzed by NMR, HPLC and LC-MS.
MS-ESI: 220 ($M^+$+1, 100).
Elementary analysis:

| Calculated: | C 76.68% H 8.27% N 6.39% |
|---|---|
| Determined: | C 76.65% H 8.25% N 6.36% | g) Synthesis of N-[2-($^{18}$F)fluoroethyl]-N-[(2R)-1-phenylpropan-2-yl]prop-2-yn-1-amine (6c)

The desired product 6c was obtained from 6e according to the general procedure C.

Example 7 a) Synthesis of (1R,2R)-2-[methyl(prop-2-yn-1-yl)amino]-1-phenylpropan-1-ol (7a)

A mixture of (1R,2R)pseudoehedrine 150 mg, 0.72 mmol) and NaOH (60 mg, 1.5 mmol), in MeCN (5 ml) was stirred at room temperature for 30 min. To the stirred mixture prpargyl bromide (1.0 mmol) was added and the reaction mixture was refluxed for overnight. The reaction mixture was allowed to cool to room temperature and solvent was evaporated under reduced pressure. The residue was partitioned between $CH_2Cl_2$ (20 ml) and water (10 ml). The organic phase was separated and washed with saturated $NaHCO_3$ (10 ml) and brine (10 ml). The organic layer was dried over $MgSO_4$ and filtered. The solvent was removed under reduced pressure to obtain the crude product as a light yellow liquid. The crude product 7a was purified by silica-gel column chromatography (hexane/ether 8:2).
MS-ESI: 204 ($M^+$+1, 100).
Elementary analysis:

| Calculated: | C 76.81% H 8.43% N 6.89% |
|---|---|
| Determined: | C 76.78% H 8.42% N 6.88% | b) Synthesis of N-[(1S,2R)-1-fluoro-1-phenylpropan-2-yl]-N-methylprop-2-yn-1-amine (7b)

To the stirred solution of 7a (150 mg, 0.74 mmol) in dichloromethane (3 mL) DAST (1.0 mmol) was added drop wise at −5° C. and the reaction mixture was stirred for additional 20 min at the same temperature. Saturated sodium carbonate (2.0 mL) was added to quench the untreated DAST. The organic layer was partitioned between $CH_2Cl_2$ (15 ml) and water (10 ml). The organic phase was separated and washed with brine (10 ml) and dried over $MgSO_4$ and filtered. The solvent was removed under reduced pressure to obtain the crude product as light yellow oil. The crude product was purified by silica-gel column chromatography (hexane/ether 4:1)
MS-ESI: 206 ($M^+$+1, 100).
Elementary analysis:

| Calculated: | C 76.07% H 7.86% N 6.82% |
|---|---|
| Determined: | C 76.02% H 7.85% N 6.81% | c) Synthesis of N-[(1S,2R)-1-chloro-1-phenylpropan-2-yl]-N-methylprop-2-yn-1-amine (7c)

To a stirred solution of 7a (120 mg, 0.54 mmol) in THF (2 ml) triethyl amine (1.0 mmol) was added. The mixture was stirred at room temperature for 30 min. To the stirred mixture mesylchloride (0.60 mmol) was added drop wise at −7° C. and the reaction mixture was stirred at room temperature for additional 30 min. Saturated $Na_2CO_3$ solution (1 mL) was added and stirred for 30 more min. The organic layer was partitioned between $CH_2Cl_2$ (15 ml) and water (10 ml). The organic phase was separated and washed with saturated $NaHCO_3$ (10 ml) and brine (10 ml) and dried over $MgSO_4$ and filtered. The solvent was removed under reduced pressure to obtain the crude product as light yellow oil. The crude product 7c was purified by silica-gel column chromatography (hexane/ether 3:1).

MS-ESI: 221 ($M^+35Cl+1$, 70).

Elementary analysis:

| Calculated: | C 70.42% H 7.27% Cl 15.99% N 6.32% |
| Determined: | C 70.39% H 7.25% Cl 15.97% N 6.30% |

Example 8 a) Synthesis of (3aS,8aR)-3,3a,8,8a-tetrahydroindeno[1,2-d][1,2,3]oxathiazole 2, 2-dioxide (8a)

To a stirred solution of 5g (33 mmol) commercially available (1S,2R)-1-amino-2,3-dihydro-1H-inden-2-ol in 200 ml dichloromethane and 9.3 ml (67 mmol) triethyl amine was added 3.25 ml (40 mmol) sulforylchloride ($SO_2Cl_2$) in 80 ml dichloromethane at −65° C. The reaction mixture was stirred for 3 h and warmed slowly to room temperature and stirred at this temperature for 18 hours. The precipitate was filtered and the filtrate was washed three times with water and then with brine, dried over magnesium sulphate and concentrated. The residue was diluted in little dichloromethane and recrystallizes in hexane. The product was purified by columns chromatography (ethyl acetate hexane 0:100→100:0) to obtain 2.2 g of the desired product 8a.

MS-ESI: 212 ($M^++1$)

Elementary analysis:

| Calculated: | C 51.17% H 4.29% N 6.63% |
| Determined: | C 57.20% H 4.30% N 6.61% | b) Synthesis of (3aS,8aR)-3-(prop-2-yn-1-yl)-3,3a,8,8a-tetrahydroindeno[1,2-d][1,2,3]oxathiazole 2,2-dioxide (8b)

To a stirred solution of 2.2 g (10.4 mmol) 8a in 120 ml dimethylformamide was added 1.35 ml (22.8 mmol) prop-2-yn-1-ol and 6 g (22.8 mmol) triphenylphosphin and 4.42 ml (22.8 mmol) dipropan-2-yl (E)-diazene-1,2-dicarboxylate. The reaction mixture was stirred for 2 h and concentrated. The residue was purified by two subsequent column chromatographies (ethyl acetate hexane1:20→2:1) to obtain 970 mg (37%) of the desired product 8b.

MS-ESI: 250 ($M^++1$)

Elementary analysis:

| Calculated: | C 57.82% H 4.45% N 5.62% |
| Determined: | C 57.85% H 4.46% N 5.61% | c) Synthesis of [(1S,2S)-2-fluoro-2,3-dihydro-1H-inden-1-yl]prop-2-yn-1-ylsulfamic acid (8c)

To a stirred solution of 100 mg (0.4 mmol) 8b in 2 ml dry THF was added 139 mg (0.44 mmol) tetrabutylammonium fluoride. The reaction mixture was stirred for 90 min and concentrated. The residue was purified by preparative HPLC. The desired product 8c was obtained in 10% yield containing minor amounts of TBAF.

d) Synthesis of (1S,2S)-2-fluoro-N-(prop-2-yn-1-yl)-2,3-dihydro-1H-inden-1-amine (8d)

To a stirred solution of 100 mg (0.4 mmol) 8b in 2 ml dry THF was added 139 mg (0.44 mmol) tetrabutylammonium fluoride at 0° C. The reaction mixture was stirred for 90 min and concentrated. 2 ml 3N sulphuric acid was added and the solution was heated in microwave oven for 10 min. The solution was poured into 20 ml ice-cold and vigorously stirred 0.35 N sodium hydroxide solution. The aqueous phase was extracted with dichloromethane-isopropyl alcohol mixture (10:1) and the organic phase was dried over magnesium sulphate and concentrated. The residue The residue was purified by preparative HPLC to obtain the compound 8d as 14 mg amount batch e) Synthesis of (1S,2S)-2-($^{18}F$)fluoro-N-(prop-2-yn-1-yl)-2,3-dihydro-1H-inden-1-amine (8e)

The desired product 8e was obtained according to the general procedure E

The features of the present invention disclosed in the specification, the claims and/or in the accompanying drawings, may, both separately, and in any combination thereof, be material for realizing the invention in various forms thereof.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 07021042.2, filed Oct. 26, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula Ia

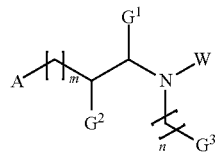

Ia wherein
W is —CH$_2$—C≡CH;
A is substituted or unsubstituted aryl, substituted or unsubstituted heteroaryl, G$^4$-(C$_2$-C$_4$)alkynyl-, G$^4$-(C$_1$-C$_4$)alkoxy-, (G$^4$-(C$_1$-C$_4$)alkyl)aryl-, or G$^4$-(C$_1$-C$_4$)alkoxy)aryl-,
G$^1$, G$^2$, G$^3$ and G$^4$ are, independently and individually, at each occurrence, hydrogen, (C$_1$-C$_4$)alkyl, L, or —(C$_1$-C$_6$)alkyl-L,
with the proviso that exactly one of G$^1$-G$^4$ is L or —(C$_1$-C$_6$)alkyl-L,
L is a leaving group, or L is F,
n is an integer from 0 to 6, and
m is an integer from 1 to 4,
or a pharmaceutically acceptable salt, ester, amide, or complex thereof.

2. The compound according to claim 1, wherein A is substituted or unsubstituted phenyl, substituted or unsubstituted furanyl, G$^4$-(C$_3$-C$_4$)alkynyl-, G$^4$-(C$_1$-C$_3$)alkoxy-, (G$^4$-(C$_1$-C$_3$)alkyl)phenyl-, or (G$^4$-(C$_1$-C$_3$)alkoxy)phenyl-.

3. The compound according to claim 2, wherein A is substituted or unsubstituted phenyl, substituted or unsubstituted furanyl, (G$^4$-(C$_1$-C$_3$)alkyl)phenyl-, (G$^4$-(C$_1$-C$_3$)alkoxy)phenyl-, hydroxy-phenyl, halo-phenyl, methoxy-phenyl, dimethoxy-phenyl, trifluormethyl-phenyl, or ((C$_1$-C$_4$)alkyl)-phenyl.

4. The compound according to claim 3, wherein A is substituted or unsubstituted phenyl, (G$^4$-(C$_1$-C$_3$)alkoxy)phenyl-, hydroxyl-phenyl, fluorophenyl, methoxyphenyl, or methylphenyl.

5. The compound according to claim 1, wherein G$^1$, G$^2$, G$^3$ and G$^4$ are independently and individually, at each occurrence, hydrogen, (C$_1$-C$_4$)alkyl, L, or —(C$_1$-C$_4$)alkyl-L, with the proviso that exactly one of G$^1$-G$^4$ is L or —(C$_1$-C$_4$)alkyl-L.

6. The compound according to claim 5, wherein G$^1$, G$^2$, G$^3$ and G$^4$ are independently and individually, at each occurrence, hydrogen, methyl, L, or —(C$_1$-C$_2$)alkyl-L, with the proviso that exactly one of G$^1$-G$^4$ is L or —(C$_1$-C$_2$)alkyl-L.

7. The compound according to claim 6, wherein G$^1$, G$^2$, G$^3$ and G$^4$ are independently and individually, at each occurrence, hydrogen, methyl, L, or -methyl-L, with the proviso that exactly one of G$^1$-G$^4$ is L or -methyl-L.

8. The compound according to claim 1, wherein L is halo, mesyloxy, tosyloxy, trifluormethylsulfonyloxy, nona-fluorobutylsulfonyloxy, (4-bromo-phenyl)sulfonyloxy, (4-nitro-phenyl)sulfonyloxy, (2-nitro-phenyl)sulfonyloxy, (4-isopropyl-phenyl)sulfonyloxy, (2,4,6-tri-isopropyl-phenyl) sulfonyloxy, (2,4,6-trimethyl-phenyl)sulfonyloxy, (4-tertbutyl-phenyl)sulfonyloxy, or (4-methoxy-phenyl)sulfonyloxy.

9. The compound according to claim 8, wherein L is chloro, bromo, mesyloxy, tosyloxy, trifluormethylsulfonyloxy, (4-bromo-phenyl)sulfonyloxy, (4-nitro-phenyl)sulfonyloxy, (4-isopropyl-phenyl)sulfonyloxy, or (2,4,6-tri-isopropyl-phenyl) sulfonyloxy.

10. The compound according to claim 1 which is

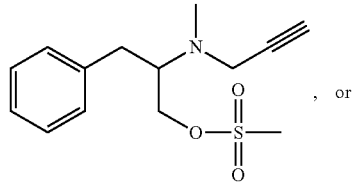

Methanesulfonic acid 2-(methyl-prop-2-ynyl-amino)-3-phenyl-propyl ester

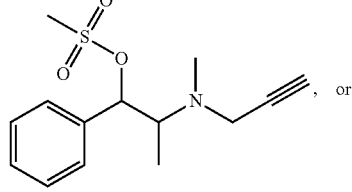

Methanesulfonic acid 2-(methyl-prop-2-ynyl-amino)-1-phenyl-propyl ester

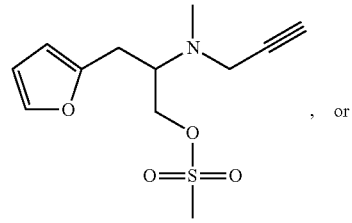

Methanesulfonic acid 3-furan-2-yl-2-(methyl-prop-2-ynyl-amino)-propyl-ester

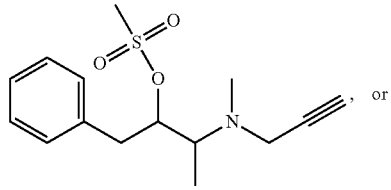

Methanesulfonic acid 1-benzyl-2-(methyl-prop-2-ynyl-amino)-propyl ester

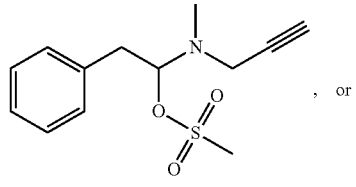

Methanesulfonic acid 1-(methyl-prop-2-ynyl-amino)-2-phenyl-ethyl ester

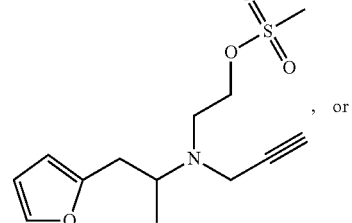

Methanesulfonic acid 2-[(2-furan-2-yl-1-methyl-ethyl)-prop-2-ynyl-amino]-ethyl ester -continued

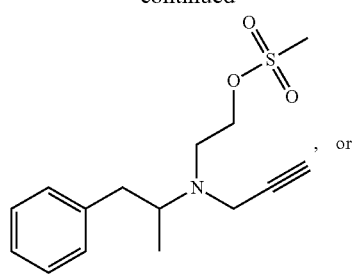

Methanesulfonic acid 2-[(1-methyl-2-phenyl-ethyl)-prop-2-ynyl-amino]-ethyl ester

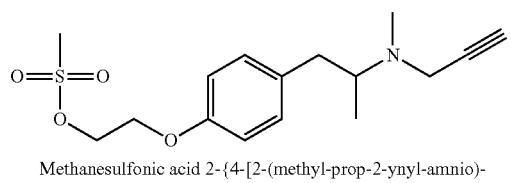

Methanesulfonic acid 2-{4-[2-(methyl-prop-2-ynyl-amnio)-propyl]-phenoxy}-ethyl ester

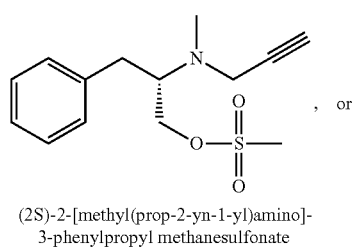

(2S)-2-[methyl(prop-2-yn-1-yl)amino]-3-phenylpropyl methanesulfonate

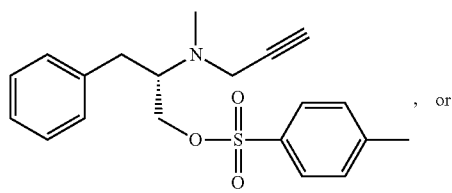

(2S)-2-[methyl(prop-2-yn-1-yl)amino]-3-phenylpropyl 4-methylbenzenesulfonate

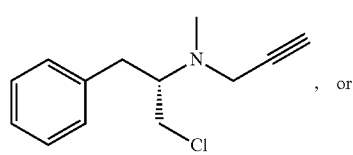

N-[(2S)-1-chloro-3-phenylpropan-2-yl]-N-methylprop-2-yn-1-amine

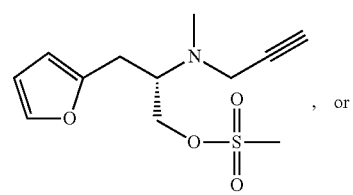

(2S)-3-(furan-2-yl)-2-[methyl(prop-2-yn-1-yl)amino]propyl methanesulfonate

-continued

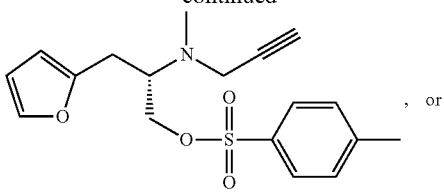

(2S)-3-(furan-2-yl)-2-[methyl(prop-2-yn-1-yl)amino]propyl 4-methylbenzenesulfonate

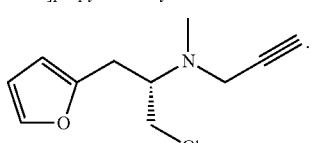

N-[(2S)-1-chloro-3-(furan-2-yl)propan-2-yl]-N-methylprop-2-yn-1-amine

11. The compound according to claim 1, wherein L is not F.

12. The compound according to claim 1, wherein L is $^{18}$F.

13. The compound according to claim 1, wherein L is $^{19}$F.

14. A composition comprising a compound according to claim 1 and a pharmaceutically acceptable carrier or diluent.

15. A composition comprising a compound according to claim 12 and a pharmaceutically acceptable carrier or diluent.

16. A composition comprising a compound according to claim 13 and a pharmaceutically acceptable carrier or diluent.

17. A composition comprising a compound according to claim 11 and a pharmaceutically acceptable carrier or diluent.

18. A kit comprising a sealed vial containing a predetermined quantity of a compound according to claim 11.

19. A method for detecting the presence of monoamine oxidase in a patient's body, comprising: introducing into said patient's body a detectable amount of a compound according to claim 12 and detecting said compound by positron emission tomography (PET).

20. A method of treatment of a disease of the central nervous system comprising the step of introducing into a patient a suitable quantity of a compound according to claim 1.

21. A method of treatment of a disease of the central nervous system comprising the step of introducing into a patient a suitable quantity of a compound according to claim 12.

22. A method of treatment of a disease of the central nervous system comprising the step of introducing into a patient a suitable quantity of a compound according to claim 13.

23. The compound according to claim 13, wherein said compound contains exactly one $^{19}$F-atom and the $^{19}$F-atom is attached to an sp$^3$-hybridized carbon atom.

24. The compound according to claim 1, wherein n is 1-3.

25. The compound according to claim 1, wherein n is 1-2.

26. The compound according to claim 1, wherein m is 1 to 2.

27. The method according to claim 19, wherein said method is for imaging a disease of the central nervous system in said patient.

28. The compound according to claim 12, wherein said compound is selected from the following compounds:

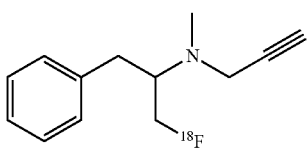

[F-18]-(1-Fluoromethyl-2-phenyl-
ethyl)-methyl-prop-2-ynyl-amine

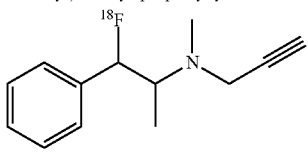

[F-18]-(2-Fluoro-1-methyl-2-phenyl-
ethyl)-methyl-prop-2-ynyl-amine

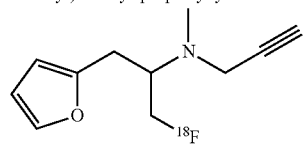

[F-18]-(1-Fluoromethyl-2-furan-2-yl-
ethyl)-methyl-prop-2-ynyl-amine

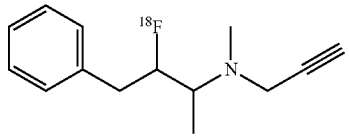

[F-18]-(2-Fluoro-1-methyl-3-phenyl-
propyl)-methyl-prop-2-ynyl-amine

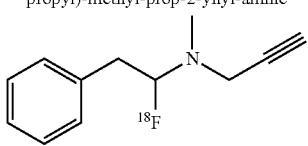

[F-18]-(1-Fluoro-2-phenyl-ethyl)-
methyl-prop-2-ynyl-amine

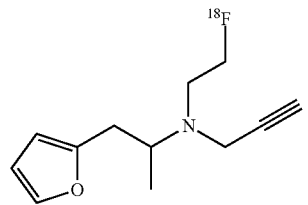

[F-18]-(2-Fluoro-ethyl)-(2-furan-2-yl-1-
methyl-ethyl)-prop-2-ynyl-amine

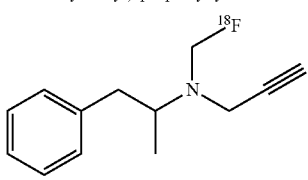

[F-18]-Fluoromethyl-(1-methyl-2-
phenyl-ethyl)-prop-2-ynyl-amine

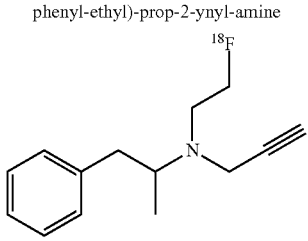

[F-18]-(2-Fluoro-ethyl)-(1-methyl-2-
phenyl-ethyl)-prop-2-ynyl-amine

-continued

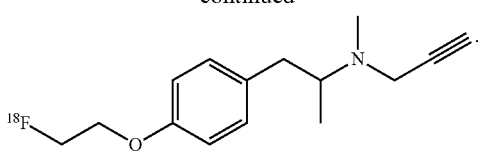

[F-18]-{2-[4-(2-Fluoro-ethoxy)-phenyl]-1-
methyl-ethyl}-methyl-prop-2-ynyl-amine

29. The compound according to claim 13, wherein said compound is selected from the following compounds:

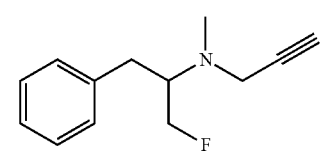

(1-Fluoromethyl-2-phenyl-ethyl)-
methyl-prop-2-ynyl-amine

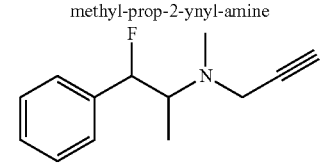

(2-Fluoro-1-methyl-2-phenyl-ethyl)-
methyl-prop-2-ynyl-amine

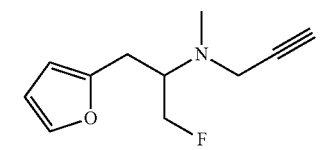

(1-Fluoromethyl-2-furan-2-yl-ethyl)-
methyl-prop-2-ynyl-amine

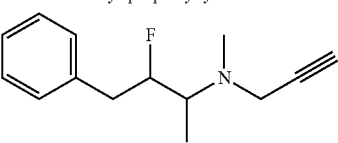

(2-Fluoro-1-methyl-3-phenyl-propyl)-
methyl-prop-2-ynyl-amine

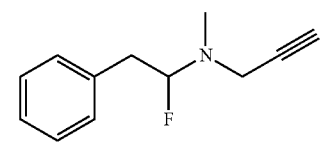

(1-Fluoro-2-phenyl-ethyl)-
methyl-prop-2-ynyl-amine

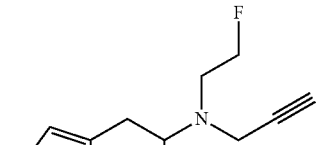

(2-Fluoro-ethyl)-(2-furan-2-yl-
1-methyl-ethyl)-prop-2-ynyl-amine

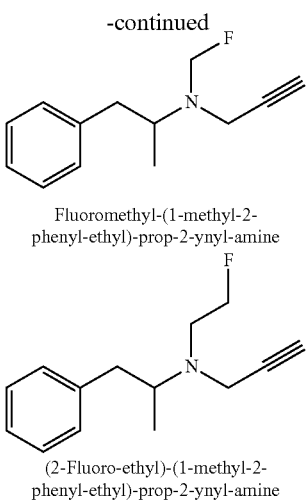

Fluoromethyl-(1-methyl-2-phenyl-ethyl)-prop-2-ynyl-amine (2-Fluoro-ethyl)-(1-methyl-2-phenyl-ethyl)-prop-2-ynyl-amine

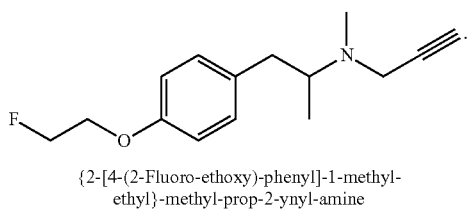 [SMILES: C#CCN(C)C(C)Cc1ccc(OCCF)cc1]

{2-[4-(2-Fluoro-ethoxy)-phenyl]-1-methyl-ethyl}-methyl-prop-2-ynyl-amine

30. A method of synthesizing a compound according to claim 12, comprising reacting one or more compounds of formula Ia wherein L is a leaving group with an F-fluorinating agent in which F is $^{18}$F.

31. The method according to claim 30, wherein L is halo, mesyloxy, tosyloxy, trifluormethylsulfonyloxy, nona-fluorobutylsulfonyloxy, (4-bromo-phenyl)sulfonyloxy, (4-nitrophenyl) sulfonyloxy, (2-nitro-phenyl)sulfonyloxy, (4-isopropyl-phenyl)sulfonyloxy, (2,4,6-tri-isopropyl-phenyl) sulfonyloxy, (2,4,6-trimethyl-phenyl)sulfonyloxy, (4-tertbutyl-phenyl)sulfonyloxy, or (4-methoxy-phenyl)sulfonyloxy.

32. The method according to claim 30, wherein L is chloro, bromo, or iodo.

33. The method according to claim 30, wherein said one or more compounds of formula Ia is or includes a compound wherein $G^2$ is L, and L is chloro, bromo, or iodo.

34. The method according to claim 33, wherein the compound synthesized is one wherein $G^1$ is —($C_1$-$C_6$)alkyl-L.

35. The method according to claim 33, wherein the compound synthesized is one wherein $G^1$ is -methyl-L.

36. The method according to claim 30, wherein said F-fluorinating agent is 4, 7, 13, 16, 21, 24-hexaoxa-1,10-diazabicyclo[8.8.8]-hexacosane K F, KF, HF, KH $F_2$, CsF, NaF or a tetraalkylammonium salt, wherein F is $^{18}$F.

37. A method of synthesizing a compound according to claim 13, comprising reacting one or more compounds of formula Ia wherein L is a leaving group with an F-fluorinating agent in which F is $^{19}$F.

38. The method according to claim 37, wherein L is halo, mesyloxy, tosyloxy, trifluormethylsulfonyloxy, nona-fluorobutylsulfonyloxy, (4-bromo-phenyl)sulfonyloxy, (4-nitrophenyl)sulfonyloxy, (2-nitro-phenyl)sulfonyloxy, (4-isopropyl-phenyl)sulfonyloxy, (2,4,6-tri-isopropyl-phenyl) sulfonyloxy, (2,4,6-trimethyl-phenyl)sulfonyloxy, (4-tertbutyl-phenyl)sulfonyloxy, or (4-methoxy-phenyl)sulfonyloxy.

39. The method according to claim 37, wherein L is chloro, bromo, or iodo.

40. The method according to claim 37, wherein said one or more compounds of formula Ia is or includes a compound wherein $G^2$ is L, and L is chloro, bromo, or iodo.

41. The method according to claim 40, wherein the compound synthesized is one wherein $G^1$ is —($C_1$-$C_6$)alkyl-L.

42. The method according to claim 40, wherein the compound synthesized is one wherein $G^1$ is -methyl-L.

43. The method according to claim 37, wherein said F-fluorinating agent is 4, 7, 13, 16, 21, 24-hexaoxa-1,10-diazabicyclo[8.8.8]-hexacosane K F, KF, HF, KH $F_2$, CsF, NaF or a tetraalkylammonium salt, wherein F is $^{19}$F.

44. The method according to claim 30, wherein a mixture of the following compounds 42 and 43

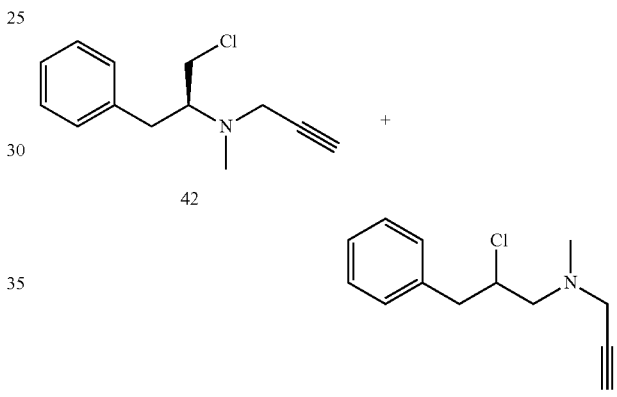

is reacted with a $^{18}$F-fluorinating agent to obtain a mixture of the following compounds 13 and 39

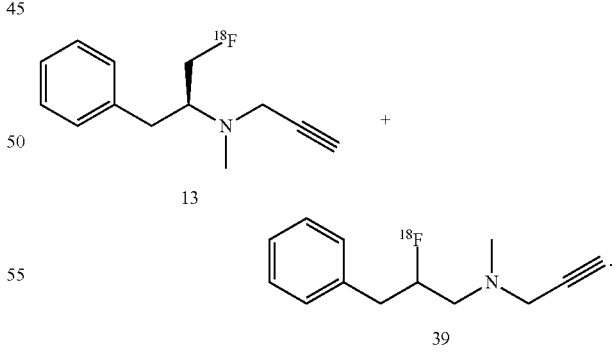

* * * * *